(12) United States Patent
Zheng et al.

(10) Patent No.: US 11,074,991 B2
(45) Date of Patent: Jul. 27, 2021

(54) METHODS FOR MULTIPLEX CHROMATIN INTERACTION ANALYSIS BY DROPLET SEQUENCING WITH SINGLE MOLECULE PRECISION

(71) Applicant: The Jackson Laboratory, Bar Harbor, ME (US)

(72) Inventors: Meizhen Zheng, Farmington, CT (US); Yijun Ruan, Farmington, CT (US); Chia-Lin Wei, West Hartford, CT (US); Zhongyuan Tian, Farmington, CT (US)

(73) Assignee: The Jackson Laboratory, Bar Harbor, ME (US)

( * ) Notice: Subject to any disclaimer, the term of this patent is extended or adjusted under 35 U.S.C. 154(b) by 156 days.

(21) Appl. No.: 16/233,860

(22) Filed: Dec. 27, 2018

(65) Prior Publication Data

US 2019/0214106 A1    Jul. 11, 2019

Related U.S. Application Data

(60) Provisional application No. 62/629,400, filed on Feb. 12, 2018, provisional application No. 62/610,716, filed on Dec. 27, 2017.

(51) Int. Cl.
| | |
|---|---|
| C12P 19/34 | (2006.01) |
| G16B 15/00 | (2019.01) |
| C12Q 1/6876 | (2018.01) |
| G16B 45/00 | (2019.01) |
| G16B 40/30 | (2019.01) |
| C12Q 1/6869 | (2018.01) |
| G16B 30/00 | (2019.01) |

(52) U.S. Cl.
CPC .......... *G16B 15/00* (2019.02); *C12Q 1/6869* (2013.01); *C12Q 1/6876* (2013.01); *G16B 40/30* (2019.02); *G16B 45/00* (2019.02); *C12Q 2600/16* (2013.01); *G16B 30/00* (2019.02)

(58) Field of Classification Search
USPC ............ 435/6.1, 6.11, 6.12, 91.1, 91.2, 183; 436/94, 501; 536/23.1, 24.3, 24.33
See application file for complete search history.

(56) References Cited

PUBLICATIONS

Chromosome Conformation Capture from from Wikipedia. Printed on Oct. 23, 2020.*
Beagrie et al., "Complex multi-enhancer contacts captured by Genome Architecture Mapping (GAM)." Nature. Mar. 23, 2017; 543(7646): 519-524.
Bintu, B. et al., "Super-resolution chromatin tracing reveals domains and cooperative interactions in single cells." Science 362, doi:10.1126/science.aau1783 (2018).
Bond-Matthews, et al., Transcription from each of the *Drosophila* act5C leader exons is driven by a separate functional promoter. Gene 62, 289-300 (1988).
Caen et al., "Microfluidics as a strategic player to decipher single-cell omics?" Trends in Biotechnolgy 35, 713-727, doi:10.1016/j.tibtech.2017.5.004. (2017).

(Continued)

*Primary Examiner* — Frank W Lu
(74) *Attorney, Agent, or Firm* — Pierce Atwood LLP

(57) ABSTRACT

The invention, in part, relates to ChIA-Drop methods, which comprise methods of drop-based sequencing.

16 Claims, 27 Drawing Sheets
(24 of 27 Drawing Sheet(s) Filed in Color)
Specification includes a Sequence Listing.

(56) References Cited

PUBLICATIONS

Cho et al., "RNA Polymerase II cluster dynamics predict mRNA output in living cells." eLife 5, doi: 10.7554/eLife.13617 (2016).
Cisse, et al., "Real-time dynamics of RNA polymerase II clustering in live human cells." Science 341, 664-667, doi:10.1126/science.1239053 (2013).
Cook et al., "A Model for all Genomes: The Role of Transcription Factories." J. Mol. Biol. (2010) 395, 1-10.
Crane, et al., "Condensin-driven remodelling of X chromosome topology during dosage compensation." Nature 523, 240-244, doi: 10.1038/nature14450 (2015).
Cremer et al., "Chromosome Territories." 2010 Cold Spring Harbor Laboratory Press; doi: 10.1101/cshperspect. a003889.
Cubenas-Potts, et l."Architectural proteins, transcription, and the three dimensional organization of the genome." FEBS letters 589, 2923-2930, 45 doi: 10.1016/j .febslet.2015.05.025 (2015).
Dixon et al., "Topological Domains in Mammalian Genomes Identified by Analysis of Chromatin Interactions." Nature. ; 485(7398): 376-380. doi:10.1038/nature11082.
Duff, M. 0. et al. "Genome-wide identification of zero nucleotide recursive splicing in Drosophila." Nature 521, 376-379, doi: 10.1038/nature14475 (2015).
Fullwood et al., "An Oestrogen Receptor α-bound Human Chromatin Interactome." Nature. Nov. 5, 2009; 462 (7269): 58-64. doi:10.1038/nature08497.
Hendrix, et al., "Promoter elements associated with RNA Pol II stalling in the Drosophila embryo." Proc. Natl. Acad. Sci., 105, 7762-7767 (2008).
Ji et al., "3D chromosome regulatory landscape of human pluripotent cells." Cell Stem Cell 18, 262-275, doi:10.1016/j.cell.2017.11.008 (02017).
Kang, et al., "Multiplexed droplet single-cell RNA-sequencing using natural genetic variation." Nature biotechnology 36, 89-94, doi: 10.1038/nbt.4042 (2018).
Kharchenko, et al. "Comprehensive analysis of the chromatin landscape in Drosophila melanogaster." Nature 471, 480-485, doi: 10.1038/nature09725 (2011).
Lajoie, et al., "The Hitchhiker's guide to Hi-C analysis: practical guidelines." Methods 72, 65-75, doi: 10.1016/j.ymeth.2014.10.031 (2015).
Lanzuolo, et al., "Polycomb response elements mediate the formation of chromosome higher-order structures in the bithorax complex." Nature cell biology 9, 1167-1174, doi:I0.1038/ncbl637 (2007).
Li et al., "Extensive promoter-centered chromatin interactions provide a topological basis for transcription regulation." Cell 148, 84-98, doi:10.1016/j.cell.2011.12.014 (2012).
Li, H. et al., "Fast and accurate short read alignment with Burrows-Wheeler transform." Bioinformatics, vol. 25 No. 14 2009, pp. 1754-1760.
Li, H. et al., "The Sequence Alignment/Map format and SAMtools." Bioinformatics, vol. 25 No. 16 2009, pp. 2078-2079.
Li, X. et al., "Long-read ChIA-PET for base-pair-resolution mapping of haplotype-specific chromatin interactions." Nature protocols 12, 899-915, doi: 10.1038/nprot.2017.012 (2017).
Lieberman-Aiden et al., "Comprehensive mapping of long range interactions reveals folding principles of the human genome. " Science. Oct. 9, 2009; 326(5950): 289-293, doi: 10.1126/science.1.
Meaburn, et al., "T. Cell biology: chromosome territories." Nature 445, 379-781, doi:I0.1038/445379a (2007).
Nagano et al., "Single cell Hi-C reveals cell-to-cell variability in chromosome structure." Nature. Oct. 3, 2013; 502(7469): . doi:10.1038/nature12593.

Quinlan et al., "BEDTools: a flexible suite of utilities for comparing genomic features." Bioinformatics, vol. 26 No. 6 2010, pp. 841-842.
Quinodoz et al., "Higher-Order inter-chromosomal hubs shape 3D genome organization in the Nucleus." Cell 174, 744-757, e724, doi:10.1016/j.cell.2018.05.024 (2018).
Ramani et al., "Massively multiplex single-cell Hi-C." Nat Methods. Mar. 2017; 14(3): 263-266.
Ramirez, F. et al. High-Affinity Sites Form an Interaction Network to Facilitate Spreading of the MSL Complex across the X Chromosome in Drosophila. Molecular cell 60, 146-162, doi: 10.1016/j.molcel.2015.08.024 (2015).
Rowley, M. J. et al. "Evolutionarily Conserved Principles Predict 3D Chromatin Organization." Molecular cell 67, 837-852 e837, doi: 10.1016/j.molcel.2017.07.022 (2017).
Sexton et al., "Three-dimensional folding and functional organization principles of the Drosophila genome." Cell 148, 458-472, doi:10.1016/j.cell.2012.01.010 (2012).
Shannon et al., "A mathematical theory of communication." ACM SIGMOBILE Mobile Computing and Communications Review 5, 3-55 (2001).
Stevens et al., "3D structure of individual mammalian genomes studied by single cell Hi-C." Nature. Apr. 6, 2017; 544(7648): 59-64.
Szabo et al., "TADs are 3D structural units of higher-order chromosome organization in Drosophila." Science advances 4, eaar8082, doi: 10. I 126/sciadv.aar8082 (2018).
Tang et al., "CTCF-mediated human 3D genome architecture reveals chromatin topology for transcription." Cell 163, 1611-1627, doi:10.1016/j.cell.2015.11.024 (2015).
Teves, S. S. & Henikoff, S. "Heat shock reduces stalled RNA polymerase II and nucleosome turnover genome-wide." Genes & development 25, 2387-2397, doi: 10.1101/gad.178079.111 10.1101/gad.177675.111 (2011).
Ulianov, et al., "Active chromatin and transcription play a key role in chromosome partitioning into topologically associating domains." Genome research 26, 70-84, doi: 10. I 101/gr.196006.115 (2016).
Van Bemmel, J. G. et al. "The insulator protein SU(HW) fine-tunes nuclear lamina interactions of the Drosophila genome." PloS one 5, e15013, doi: 10.1371/journal.pone.0015013 (2010).
Van Der Maaten et al., "Visualizing Data using t-SNE." Journal of Machine Learning Research 9 (2008) 2579-2605.
Weintraub et al., "YY1 is a structural regulator of enhancer-promoter loops." Cell 171, 1573-1588 e1528, doi:10.1016/j.cell.2017.11.008 (2017).
Yang et al., "HiCRep: assessing the reproducibility of Hi-C data using a stratum-adjusted correlation coefficient." Genome Research 27:1939-1949, (2017).
Yang, J., et al., "The BEAF-32 insulator coordinates genome organization and function during the evolution of Drosophila species." Genome research 22, 2199-2207, doi:IO. I 101/gr.142125.112 (2012).
Zhao et al., "Arabidopsis thaliana AHL family modulates hypocotyl growth redundantly by interacting with each other via the PPC/DUF296 domain." Proc. Natl. Acad. Sci. USA 110, E4688-4697, doi:10.073/pnas.1219277110 (2013).
Zhao et al., "Union Exon Based Approach for RNA-Seq Gene Quantification: To Be or Not to Be?" Nov. 11, 2015 https://doi.org/10.1371/journal.pone.0141910.
Zheng, et al., "Haplotyping germline and cancer genomes with high-throughput linked-read sequencing." Nature biotechnology 34, 303-311, doi: 10.1038/nbt.3432 (2016).

* cited by examiner

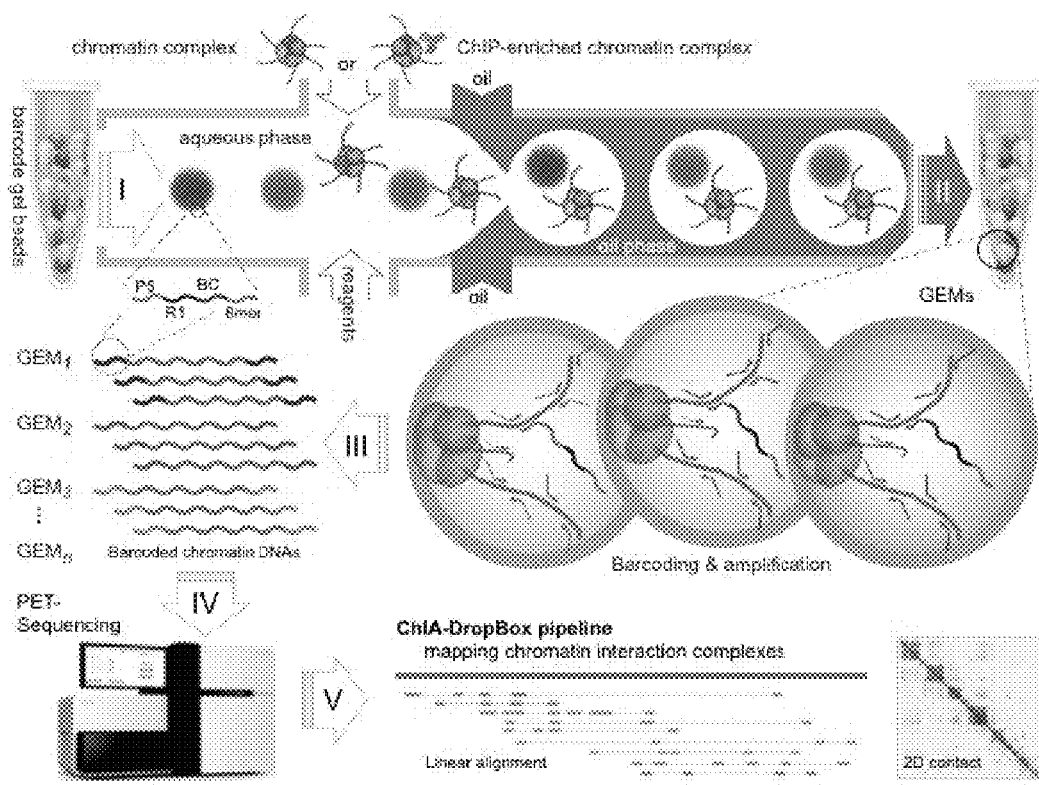
Fig. 1A
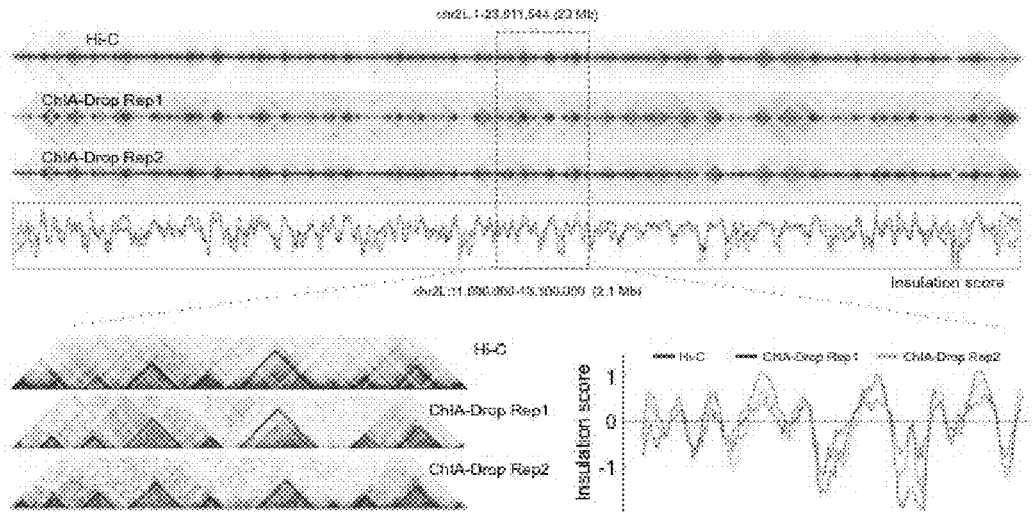
Fig. 1B
Fig. 1C

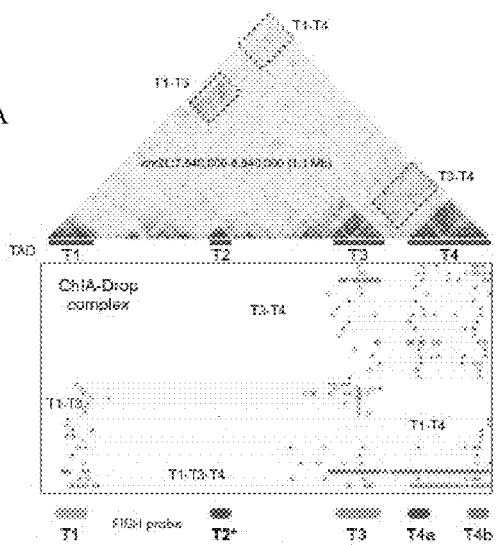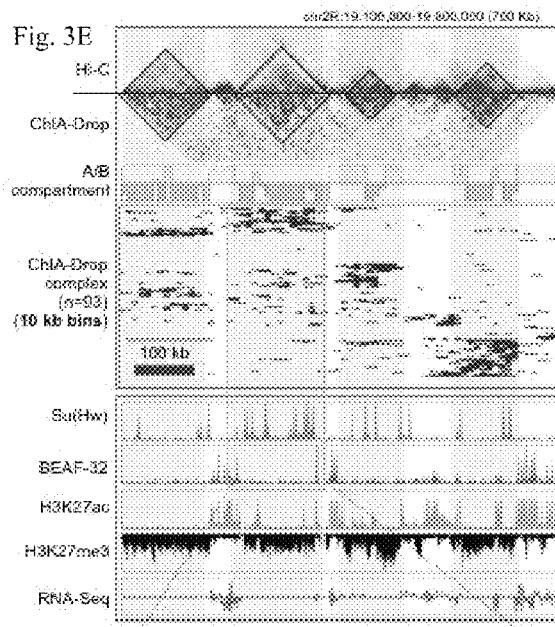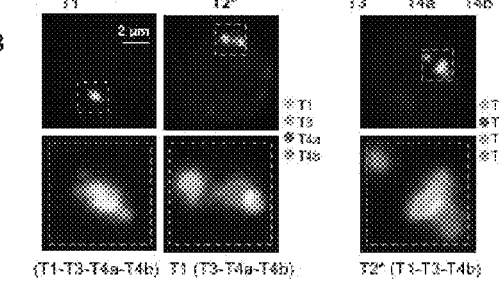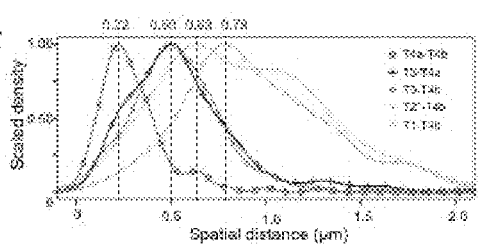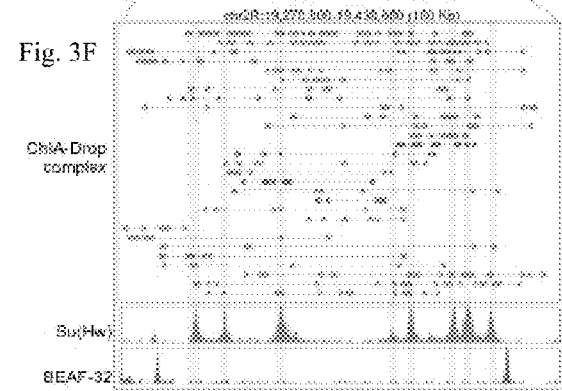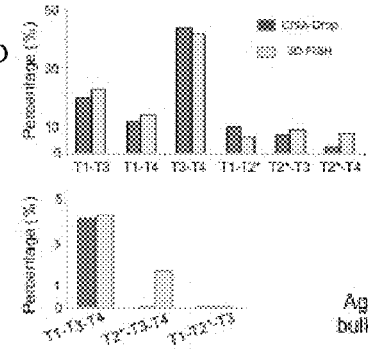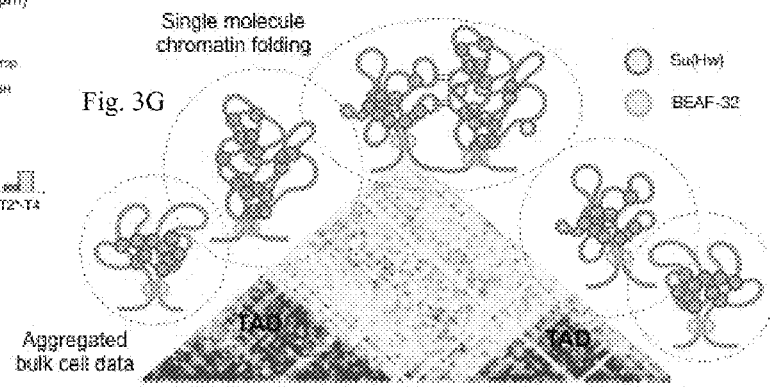

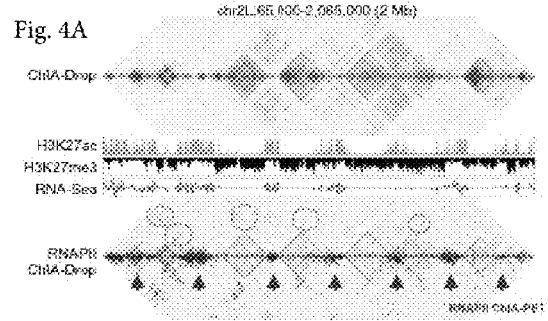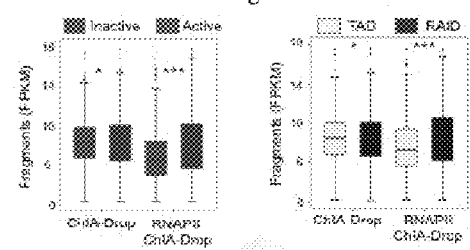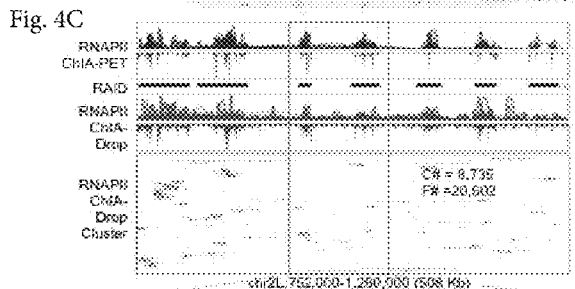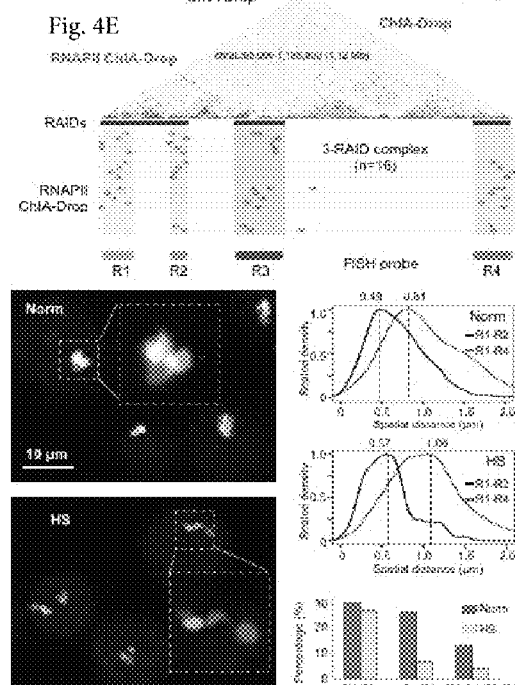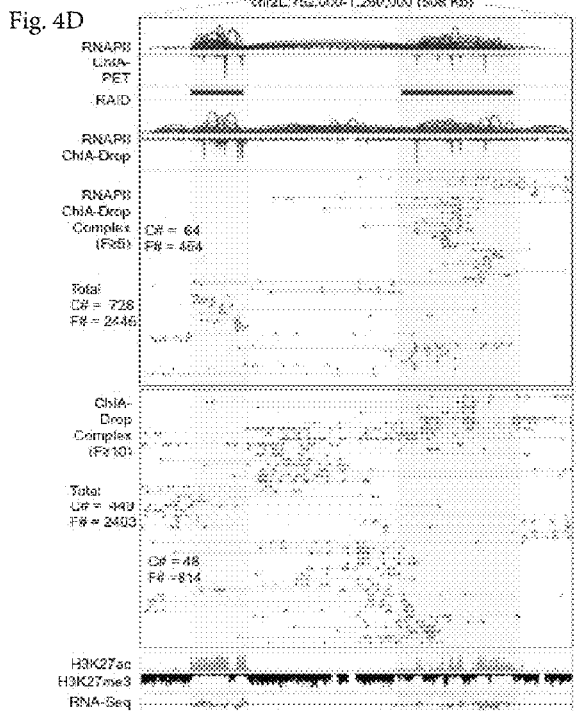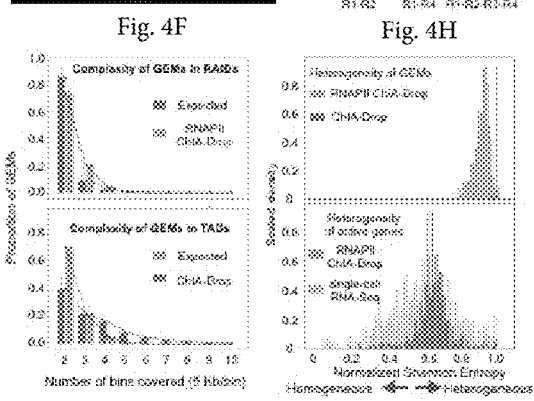
Fig. 4A  Fig. 4B  Fig. 4C  Fig. 4D  Fig. 4E  Fig. 4F  Fig. 4G  Fig. 4H  Fig. 4I  Fig. 4J Fig. 6A
Fig. 6D
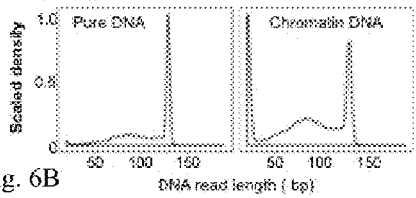
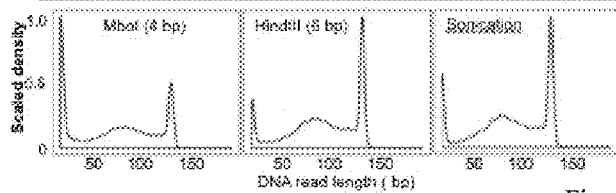
Fig. 6B
Fig. 6E
Fig. 6C
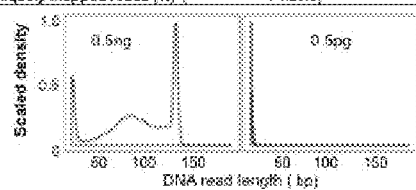
Fig. 6F
Fig. 6G

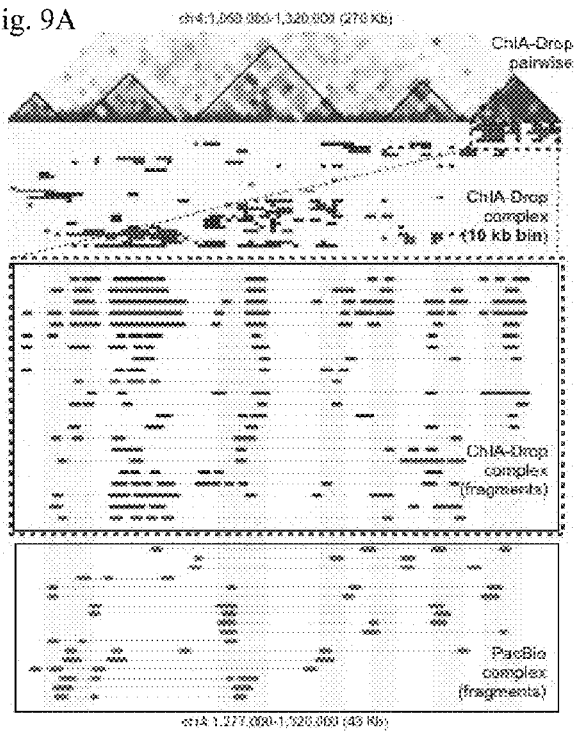
Fig. 9A
Fig. 9B
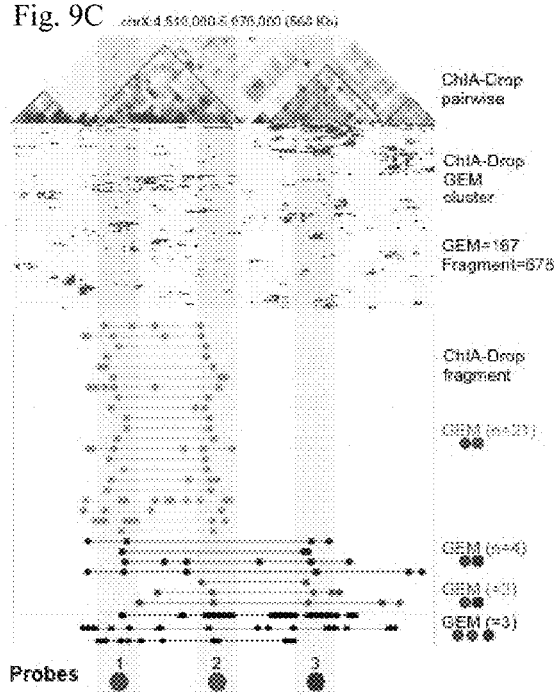
Fig. 9C
Fig. 9D
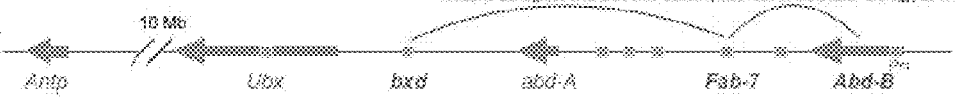
Fig. 9E
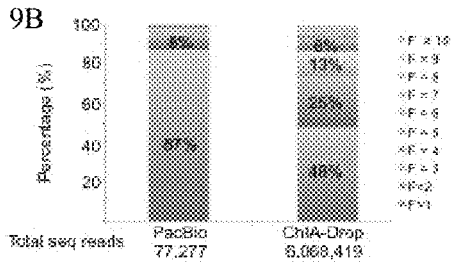
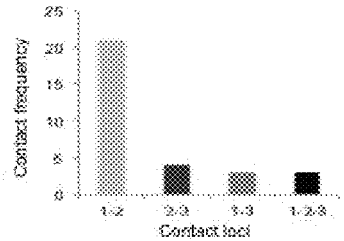
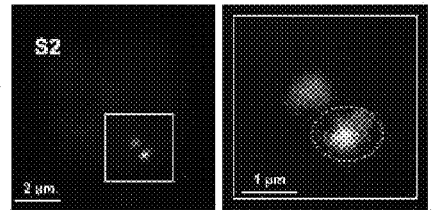
Fig. 9F    Fig. 9G
Fig. 9H    Fig. 9I    Fig. 9J

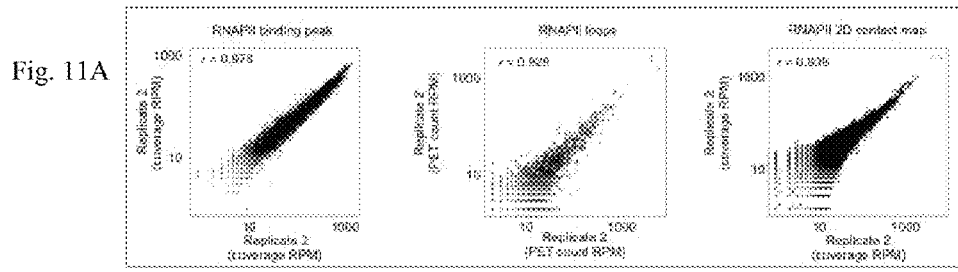
Fig. 11A
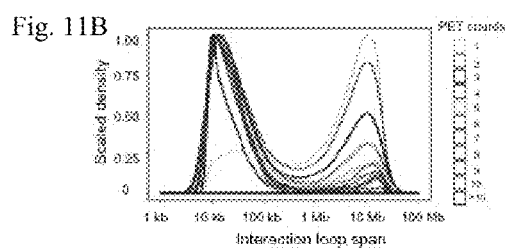
Fig. 11B
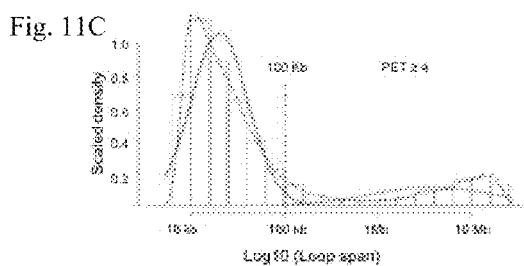
Fig. 11C
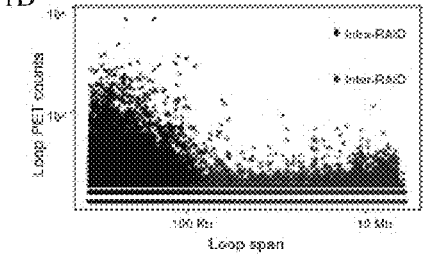
Fig. 11D
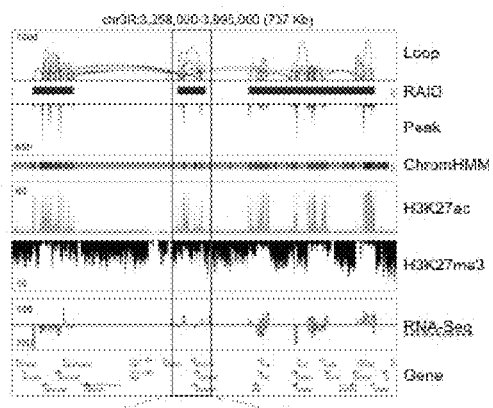
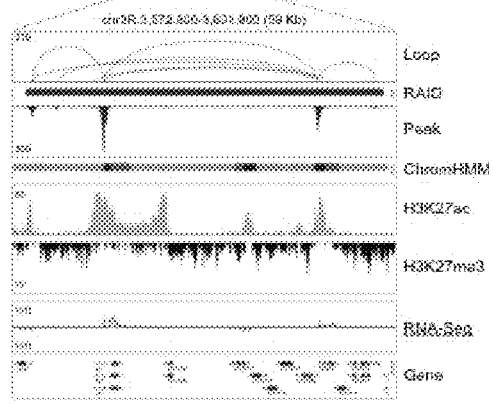
Fig. 11E
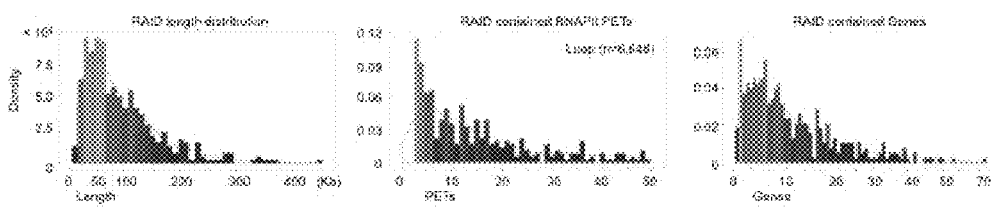
Fig. 11F

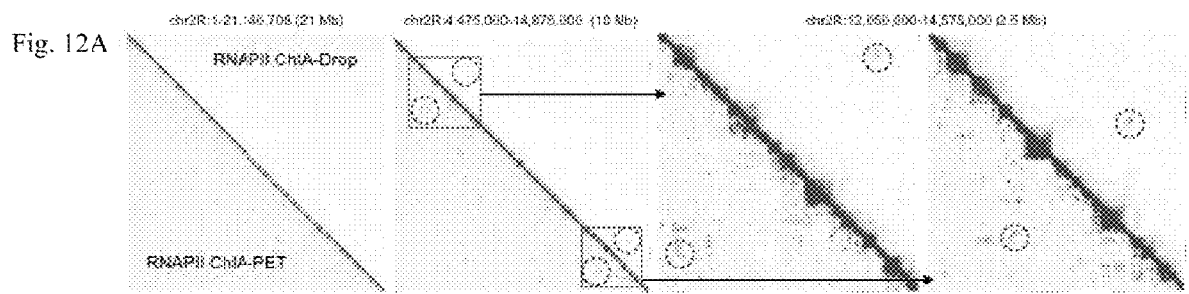
Fig. 12A
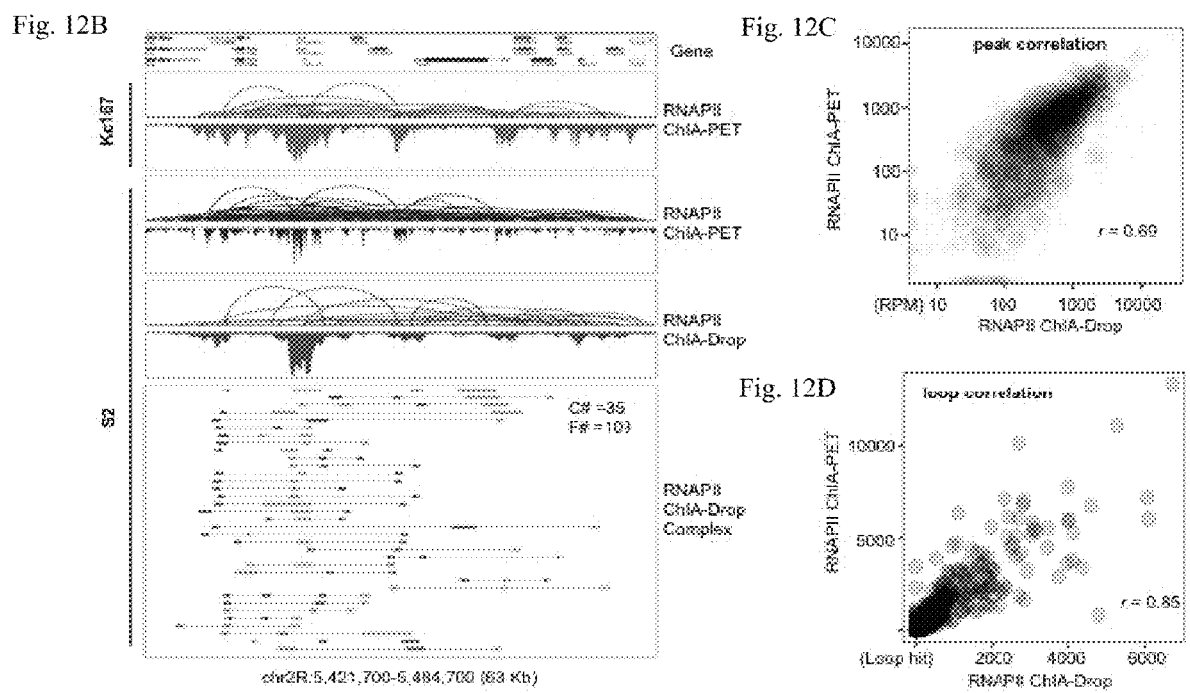
Fig. 12B
Fig. 12C
Fig. 12D
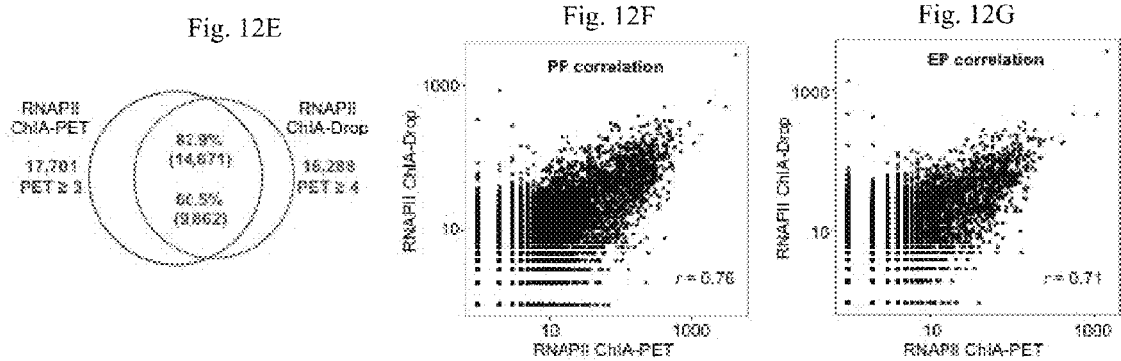
Fig. 12E
Fig. 12F
Fig. 12G Fig. 14A
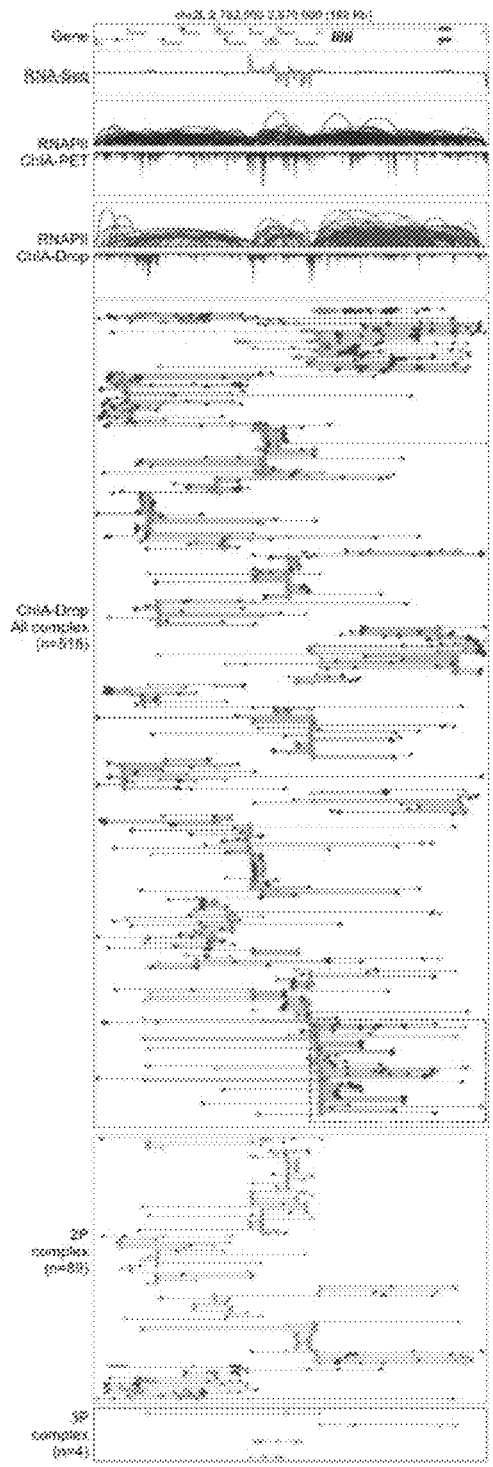
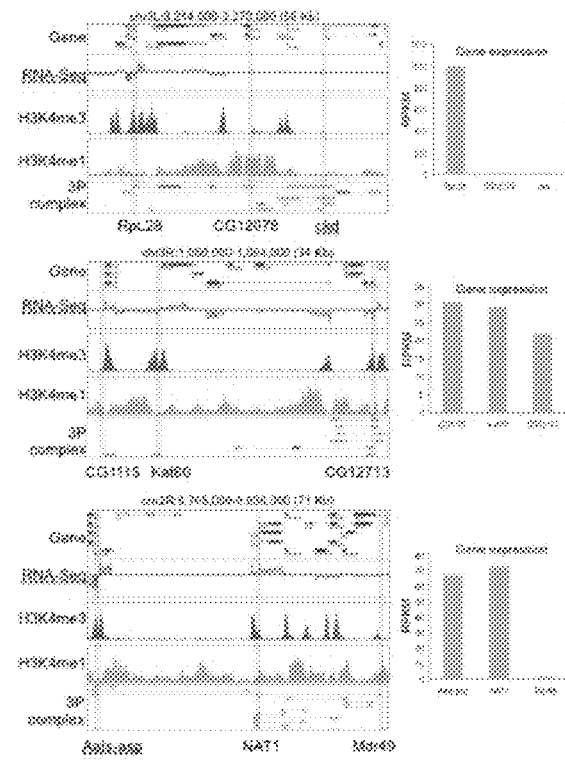
Fig. 14B
Fig. 14C
Fig. 14D
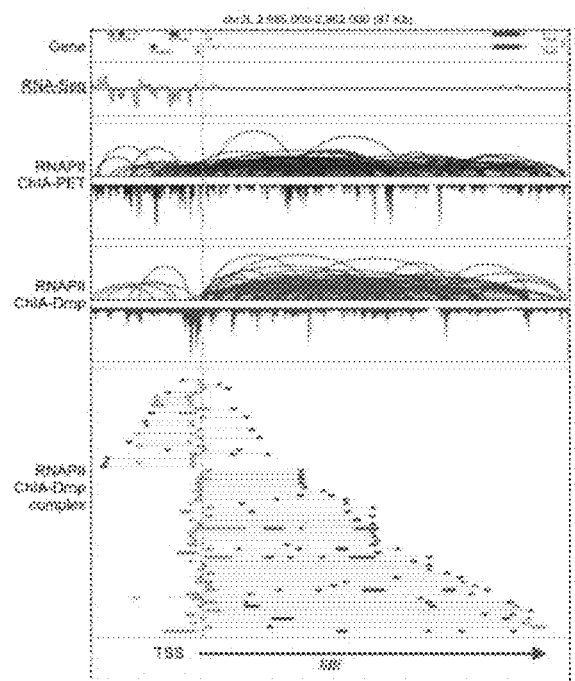
Fig. 14E

| RAID | 1 | 2 | 3 | 4 | 5 | 6 | 7 | 8 | 9 | 10 | # of bins covered | Unique count |
|---|---|---|---|---|---|---|---|---|---|---|---|---|
| GEM1 |  | 1 |  |  | 1 |  |  | 1 |  | 1 | 4 | 1 |
| GEM2 |  | 1 |  |  | 1 |  |  | 1 |  |  | 3 | 1 |
| GEM3 |  | 1 |  |  | 1 |  | 1 |  |  |  | 3 | 1 |
| GEM4 |  | 1 |  |  |  |  | 1 |  |  |  | 2 | 2 |
| GEM5 |  | 1 |  |  |  |  | 1 |  |  |  | 2 | 2 |
| GEM6 |  | 1 |  |  |  | 1 |  |  |  |  | 2 | 2 |
| GEM7 |  | 1 |  |  |  | 1 |  |  |  |  | 2 | 2 |
| GEM8 |  | 1 |  | 1 |  |  |  |  |  |  | 2 | 6 |
| GEM9 |  | 1 |  | 1 |  |  |  |  |  |  | 2 | 6 |
| GEM10 |  | 1 |  | 1 |  |  |  |  |  |  | 2 | 6 |
| GEM11 |  | 1 |  | 1 |  |  |  |  |  |  | 2 | 6 |
| GEM12 |  | 1 |  | 1 |  |  |  |  |  |  | 2 | 6 |
| GEM13 |  | 1 |  | 1 |  |  |  |  |  |  | 2 | 6 |
| GEM14 |  | 1 | 1 |  |  |  |  |  |  |  | 2 | 2 |
| GEM15 |  | 1 | 1 |  |  |  |  |  |  |  | 2 | 2 |
| GEM16 | 1 | 1 |  |  |  |  |  |  |  |  | 2 | 1 |

5 kb

METHODS FOR MULTIPLEX CHROMATIN INTERACTION ANALYSIS BY DROPLET SEQUENCING WITH SINGLE MOLECULE PRECISION

RELATED APPLICATIONS

This application claims the benefit under 35 U.S.C. § 119(e) of U.S. Provisional application Ser. No. 62/610,716 filed Dec. 27, 2017 and U.S. Provisional application Ser. No. 62/629,400 filed Feb. 12, 2018, the disclosure of each of which is incorporated by reference herein in its entirety.

SEQUENCE LISTING

The instant application contains a Sequence Listing which has been submitted electronically in ASCII format and is hereby incorporated by reference in its entirety. The ASCII copy, created on Mar. 26, 2019, is named W7192083.txt and is 64 KB in size.

GOVERNMENT INTEREST

This invention was made with government support under NIDDK U54DK107967 awarded by the National Institutes of Health and NHGRI UM1HG009409 awarded by the National Institutes of Health. The government has certain rights in the invention.

FIELD OF THE INVENTION

The invention, in some aspects, relates to methods of chromatin interaction analysis using droplet-based sequencing (ChIA-Drop).

BACKGROUND OF THE INVENTION

Emerging 3D genome mapping efforts suggest complex chromosomal folding structures. However, the true multiplex nature of chromatin interactions has not yet been fully explored. Genomes of higher organisms are extensively folded into chromosomal territories within three-dimensional (3D) nuclear space (1). Advanced long-range chromatin interaction mapping methods have been developed that combine nuclear proximity ligation and high throughput sequencing (Hi-C) (2), plus chromatin immunoprecipitation (ChIA-PET) (3). These approaches revealed frequent chromatin contacts within topological-associated domains (TADs) (4, 5) and identified chromatin loops mediated by specific protein factors such as CTCF/cohesin, at TAD boundaries, and transcription factors (TFs), between gene promoters and enhancers, as a general transcriptional regulatory mechanism (3,6-8). More specifically, studies based on RNAPII ChIA-PET provided evidence that multiple gene-coding loci and regulatory non-coding elements could be clustered together to form complex chromatin looping structures, thereby suggesting a topological framework for co-transcriptional regulation (6, 9). However, Hi-C and ChIA-PET rely on proximity ligation to detect pairwise chromatin contacts from millions of cells. Therefore, their 3D genome mapping data reflect aggregate views of pairwise contacts averaged over millions of copies of chromatin molecules, and thus cannot reveal the detailed composition of multiplex chromatin interactions in each chromosome at single-molecule resolution. Although single-cell Hi-C (10-12) could potentially overcome this issue, its ability to do so may be limited by data sparsity inherent to all single-cell genomic assays. A new direction is to develop single molecule approaches to directly detect multiplex chromatin interactions from either single cell (13) or bulk cells (14). Recent advances in microfluidics have opened new opportunities for droplet-based genomic analysis (15), including single-cell RNA sequencing and single molecule high-molecular-weight genomic DNA sequencing (17), yet this approach has not been adapted to chromatin interaction analysis.

SUMMARY OF THE INVENTION

According to an aspect of the invention, methods of determining a chromatin interaction at a single molecule level is provided, the methods include steps of: a) contacting a population of chromatin complexes with a plurality of barcode substrates, each individual substrate comprising multiple copies of a unique DNA barcode of nucleotides to form a population of barcoded chromatin complexes; b) partitioning the population of barcoded chromatin complexes into droplets such that each droplet contains not more than one barcoded chromatin complex, each barcoded chromatin complex comprising chromatin DNA ligated to multiple copies of the unique barcode; c) amplifying the chromatin DNA; d) releasing the chromatin DNA from the chromatin complex; e) sequencing the chromatin DNA to generate a plurality of DNA sequence reads; and f) mapping the plurality of sequence reads to a referenced genome to produce a genomic location of the sequence reads to generate a 3D genomic connectivity map, wherein the connectivity map is indicative the physical interaction between nucleic acids in the chromatin complex at a single molecule level. In some embodiments, the DNA barcode comprises ten or more nucleotides. In some embodiments, the DNA barcode comprise 8, 9, 10, 11, 12, or more nucleotides. In certain embodiments, the chromatin complexes comprise chromatin DNA and chromatin protein and are obtained by providing a crosslinked, permeabilized nucleus and digesting the crosslinked, permeabilized nucleus to provide a population of chromatin complexes. In some embodiments, the crosslinked, permeabilized nucleus is prepared by crosslinking a cell with a crosslinking reagent to form a crosslinked cell comprising a crosslinked nucleus, lysing the crosslinked cell, isolating the crosslinked nucleus from the lysed cell, and permeabilizing the isolated crosslinked nucleus with a permeabilizing reagent. In some embodiments, the crosslinking reagent is formaldehyde. In certain embodiments, the formaldehyde is 1% (w/v) formaldehyde. In some embodiments, the permeabilizing reagent is SDS. In certain embodiments, the SDS is 0.5% SDS. In certain embodiments, the cross-linked permeabilized nucleus is fragmented by sonication prior to the digesting step. In some embodiments, the digesting step is performed using a restriction enzyme digestion. In some embodiments, the restriction enzyme is a 4 bp cutter or a 6 bp cutter. In certain embodiments, the 4 bp cutter is MboI. In some embodiments, the 6 bp cutter is Hind III. In some embodiments, the digestion provides DNA fragments of 300-6000 bp in the chromatin complex. In certain embodiments, prior to contacting the population of chromatin complexes with the plurality of barcode substrates the population of chromatin complexes is enriched for a chromatin protein. In some embodiments, the enrichment comprises incubating the population of chromatin complexes with a monoclonal antibody specific for the chromatin protein to form chromatin complexes which are bound to the monoclonal antibody, isolating the chromatin complexes bound to the monoclonal antibody, and removing the monoclonal antibody to form a population of chromatin complexes each complex comprising the chromatin protein. In some embodiments, the chromatin protein is RNAPII, RARA, ER, or CTCF. In certain embodiments, prior to contacting the population of chromatin complexes with the plurality of barcoded substrates, population of chromatin complexes is adjusted in solution to a solution concentration of 0.5 ng DNA/µl. In some embodiments, the plurality of barcoded substrates is a plurality of gel beads in emulsion (GEMs). In certain embodiments, each GEM contains multiple copies of a DNA construct comprising a PCR priming site, a sequence reading site, a barcode, and a random priming nucleotide sequence. In some embodiments, the barcode is a 15 nt to 25 nt barcode or a 16 nt to 20 nt barcode. In some embodiments, the random priming nucleotide sequence is a random 8-mer. In certain embodiments, the amplifying step is performed by isothermal incubation at about 30° C. for about 8-16 hours. In some embodiments, after the releasing step the chromatin DNA is subjected to one or more of end repair, A-tailing, and adapter ligation prior to sequencing. In some embodiments, the sequencing is 150 bp sequencing and each sequence contains the barcode.

According to another aspect of the invention, methods of mapping chromatin complexes are provided, the methods including, determining the chromatin DNA sequences as set forth in any embodiment of one of the aforementioned aspects of the invention and analyzing the sequences using a ChIA-DropBox pipeline method.

According to another aspect of the invention, methods of ChIA-DropBox pipeline sequence analysis are provided, the methods including reading the sequence data generated using any embodiment of one of the aforementioned aspects of the invention; identifying the barcode based on the reading; calling of GEMS based on the barcode identification; identifying significant chromatin complexes; and visualizing the data obtained in identification.

The present invention is not intended to be limited to a system or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE DRAWINGS

This patent application contains at least one drawing executed in color. Copies of this patent application publication with color drawing(s) will be provided by the Office upon request and payment of the necessary fee.

FIG. 1A-C provides results of certain embodiments of ChIA-Drop for multiplex chromatin interaction analysis. FIG. 1A is a schematic diagram of the ChIA-Drop method. (I) indicates input of fragmented chromatin samples or ChIP-enriched chromatin samples are loaded to the microfluidics device (10x Genomics' Chromium instrument) to produce millions of Gel beads in Emulsion (GEM). Each GEM droplet is optimized to partition one gel bead with ideally one chromatin complex along with reagents. Each gel bead contains millions of copies of barcode DNA primer. "P5", PCR priming site; "R1", sequencing priming site; "BC", 16-nt barcode; "8-mer", random 8-nt for random priming to chromatin DNA templates. (II) shows that in each GEM, chromatin DNA templates are annealed with random 8-mer for linear DNA amplification and barcoding. (III) shows that barcoded DNA amplicons from all droplets are pooled for (IV) indicates DNA sequencing and (V) provides mapping/visualization via ChIA-DropBox pipeline in linear browser view and 2D contact map. The linear multi-fragment and 2D contact views presented here were derived from the data presented in this study. FIG. 1B shows comparison of 2D contact map views for conventional Hi-C data and for replicates of ChIA-Drop data ("Rep1" and "Rep2") converted to pairwise format (chr2L is shown). Below that, the insulation scores calculated from each dataset are shown (red: Hi-C; blue: ChIA-Drop Rep 1; green: ChIA-Drop Rep2). Spearman correlation coefficients using insulation score in chr2L are 0.84 (ChIA-Drop Rep1 vs. Rep2), 0.60 (ChIA-Drop Rep1 vs. Hi-C), and 0.72 (ChIA-Drop Rep2 vs. Hi-C). FIG. 1C provides a zoomed-in view (2.1 Mb) of FIG. 1B including several TADs. Left: 2D contact views of Hi-C data and two replicates of ChIA-Drop data. TADs are annotated with black lines, identified by insulation boundaries. Right: the insulation scores of three datasets for the same zoomed-in region. Spearman correlation coefficients using insulation score in chr2L: 11 Mb-13.1 Mb are 0.87 (ChIA-Drop Rep1 vs. Rep2), 0.77 (ChIA-Drop Rep1 vs. Hi-C), and 0.84 (ChIA-Drop Rep2 vs. Hi-C).

FIG. 2A shows decomposition of ChIA-Drop data based on the number of fragments (denoted F) in each chromatin complex. First, a 2D contact map of Hi-C data is shown for a 1 Mb segment in chr2R. Then, 2D contact maps for the same region are shown of ChIA-Drop data decomposed by fragment number (then converted to pairwise contacts): a few fragments (F=2-5, F=6-9), more fragments (F=10-14, F≥15), and all fragments (F=all). FIG. 2B shows an empirical cumulative distribution function (ECDF) of the contact distance of ChIA-Drop interactions converted to pairwise. Separate curves are plotted for ChIA-Drop data by the fragment number of the complexes: ranging from low fragment number in yellow to high fragment number in red. The blue solid curve is for ChIA-Drop data that passed the significance calling step in ChIA-DropBox. As a reference, the black dotted curve indicates Hi-C data. FIG. 2C provides ChIA-Drop data in a 10 Mb segment of chr2R. The top panel displays 2D contact maps of Hi-C data and that of ChIA-Drop data converted to pairwise format. The bottom panel shows "linear multi-fragment views" of chromatin complexes containing 10 or more fragments (F≥10). Each row is a chromatin complex and the columns are 50 Kb bins. A bin is colored in red if the chromatin complex contained a fragment within that bin. The rows are then arranged by hierarchical clustering to display the relationships between complexes. FIG. 2D provides a zoomed-in browser view (1.5 Mb) of FIG. 2C, showing that ChIA-Drop complex clusters associate with TADs. From top to bottom, ChIA-Drop 2D pairwise contact map showing a region with a number of TADs and boundary regions; eigenvector-called AB (orange/gray, respectively) compartments from ChIA-Drop data; cluster view of the chromatin complexes in this region with binning at 10 Kb resolution; fragment view of the chromatin complexes in this region. Each set of the assorted color bars connected by a straight line depicts a ChIA-Drop chromatin complex. A further zoomed-in fragment view (490 Kb), highlighting the inter-TAD chromatin complexes, was shown at the bottom. FIG. 2E shows distribution plots for the number of fragments per chromatin complex involved in TADs or in gap regions. FIG. 2F provides a pie chart for the percentages of chromatin complexes that overlap in a single TAD ("1-TAD") or multiple TADs ("2-TAD" and so forth).

FIG. 3A-G provides data from embodiments of ChIA-Drop multiplex chromatin interactions. FIG. 3A shows ChIA-Drop-defined chromatin topological structures for validation with 3D FISH. Top, is a pairwise heat map of ChIA-Drop data showing 4 TADs and 3 gap regions. Inter-TAD contacts are indicated with the dashed boxes (T1-T3, T1-T4, T3-T4). Bottom, fragment view of ChIA-Drop complexes with fragments mapped in multiple TADs. FIG. 3B shows a 3D FISH probe design and representative images of 4-color FISH experiments using STED 3X/DLS confocal microscopy. Fluorescent DNA probes were made for each of the 4 TAD regions. In addition, two probes (T4a and T4b) were made to serve as an intra-TAD reference and the T2* probe as a control site for a TAD with no inter-TAD contacts. Two sets of FISH experiments were performed independently, using either the test probe combination (T1-T3-T4a-T4b in 404 nuclei) or the control probe combination (T1-T2*-T3-T4b in 221 nuclei). The left side of FIG. 3B shows 4 test probes colocalized together (T1-T3-T4a-T4b); middle, the T1 probe separated from the other 3 colocalized test probes (T3-T4a-T4b); right, the control T2* probe far away from the 3 test probes that were colocalized together. FIG. 3C shows distributions of spatial distances (μm) between pairs of probes, measured using the Imaris image analysis software. The modes of the distance distributions for each pair of probes are indicated: T4a-T4b, mode Mo=0.22 (nuclei, n=221); T3-T4a, Mo=0.5 (nuclei, n=221); T3-T4b, Mo=0.5 (nuclei, n=404); T2*-T4b, Mo=0.63 (nuclei, n=404); T1-T4b, Mo=0.78 (nuclei, n=404). FIG. 3D shows a bar chart of the percentages of ChIA-Drop complexes with fragments overlapping combinations of TADs, and the corresponding colocalization percentages from DNA FISH validation experiments. Top, ChIA-Drop complex percentages and FISH colocalization percentages for 2-TAD combinations. Bottom, ChIA-Drop complex percentages and FISH colocalization percentages for 3-TAD combinations. For FISH, the number of nuclei analyzed was 150 and the spatial-distance cutoff for colocalization was 0.28 μm. FIG. 3E shows a browser view (700 kb) of ChIA-Drop complexes, alongside epigenomic data tracks. From top to bottom: Hi-C and ChIA-Drop 2D contact maps showing a region with four TADs; eigenvector-called AB compartments from ChIA-Drop data; multi-fragment cluster view of the ChIA-Drop complexes in this region with binning at 10 kb resolution; ChIP-Seq binding profiles for Su(Hw) and BEAF-32; epigenomic tracks indicative of active chromatin (RNA-seq and H3K27ac ChIP-seq signals) or of repressive chromatin (H3K27me3 ChIP-seq signal). FIG. 3F shows a zoom-in fragment view of FIG. 3E. Top, detailed alignment of individual complexes (n=29) and fragments (n=328) in assorted colors. Bottom, Su(Hw) and BEAF-32 ChIP-seq binding profiles. FIG. 3G shows a model of chromatin folding within and between TADs at the single-molecule level. Architectural proteins, such as BEAF-32 (purple circle), help define TAD boundaries. Inside each domain, chromatin is extensively folded in a highly heterogeneous manner, possibly facilitated by architectural proteins, such as Su(Hw). Nearby chromatin domains could also have inter-domain contacts either randomly or specifically (depicted with red bars).

FIG. 4A-J provides data from embodiments of chromatin complexes from RNAPII ChIA-Drop involving multiple promoter and non-promoter elements. FIG. 4A shows a comparison of 2D contact maps for ChIA-Drop data and RNAPII ChIA-Drop data in a 2 Mb segment in chr2L. TADs defined by ChIA-Drop data are outlined in both 2D contact maps. Tracks of histone marks (H3K27ac/me3) and RNA-Seq depict the epigenomic landscape of active and inactive regions. The signal enrichment in RNAPII ChIA-Drop (red pixels) is consistent with the signal enrichment from RNAPII ChIA-PET data (blue dots and arrows). Inter-domain contacts in RNAPII ChIA-Drop data are highlighted by blue circles. FIG. 4B shows a boxplot of normalized chromatin fragment coverage in chromatin domains. Left panel, in inactive domains (dark gray) and in active domains (dark green) from ChIA-Drop data or RNAPII-enriched ChIA-Drop data. The active/inactive domains were called by segmenting signals for histone marks and RNA-seq. Two-sided Wilcoxon Rank-Sum test p-value: * p=3.4×10-13. NS, not significant. Right panel, in TADs (silver) and in RAIDs (blue) from ChIA-Drop or RNAPII ChIA-Drop. Two-sided Wilcoxon Rank-Sum test p-value: * p=9.1× 10-6. NS, not significant. Boxes depict median and interquartile range. FIG. 4C shows browser views (the same 2 Mb segment of chr2L as in panel a) of RNAPII ChIA-PET and ChIA-Drop data. From top to bottom: RNAPII ChIA-PET in loops, binding coverage, and RAIDs (blue); RNAPII ChIA-Drop loops and binding coverage; RNAPII ChIA-Drop linear fragment cluster view (brown). FIG. 4D shows a zoomed-in view of a 508 Kb genomic segment from (c). From top to bottom: RNAPII ChIA-PET loops and peaks in two RAIDs (blue); RNAPII ChIA-Drop loops and peaks; RNAPII ChIA-Drop multiplex (F≥5) complexes (n=64) and fragments (n=454) are shown in assorted colors (total 726 complexes and 2446 fragments in this region not shown due to space limit); ChIA-Drop multiplex (F≥10) complexes (n=48) and fragments (n=814) are shown in assorted colors (total 449 complexes and 2403 fragments in this region not shown due to space limit); epigenomic tracks for active (H3K27ac ChIP-Seq and RNA-Seq) and inactive (H3K27me3 ChIP-Seq) domains. FIG. 4E shows ChIA-Drop and RNAPII ChIA-Drop-defined chromatin topological structures for validation with 3D FISH. Top, pairwise heat map of ChIA-Drop data showing multiple TADs and RNAPII-associated interaction domains (RAIDs). Interaction loops from RNAPII ChIA-Drop are indicated in green. Bottom, fragment view of RNAPII ChIA-Drop complexes with fragments mapped in multiple RAIDs. FIG. 4F includes two panels showing 3D FISH probe design and representative images of 4-color FISH experiments. Fluorescent DNA probes R1, R2, R3 and R4 were made corresponding to the RAID regions in FIG. 4E. The 4-color probes were used for FISH experiments in S2 cells with or without heat shock (HS)-treatment. FIG. 4F upper panel, the 4 probes were colocalized together in the untreated (normal) cells. FIG. 4F, lower panel, the 4 probes were scattered in heat shock-treated cells. The scale bar indicates 10 μm. The dashed box indicates a region highlighted for a zoomed in view in the inset. FIG. 4G shows spatial distances (μm) of probe pairs in normal S2 cells (n=213) and heat shock-treated cells (n=150), analyzed using the Imaris image analysis software. FIG. 4G, upper panel, distributions of spatial distances in the normal, untreated cells (n=213). The modes of spatial distance distributions for each of the probe pairs are indicated: R1-R2, mode Mo=0.48; R1-R4, Mo=0.81. FIG. 4G, lower panel, curves of spatial distances in the heat shock-treated cells (n=150). The modes of spatial distance distributions for each of the probe pairs are indicated: R1-R2, Mo=0.57; R1-R4, Mo=1.06. The spatial distances of R1-R2 and R1-R4 observed in HS-treated cells were notably larger than in untreated normal cells. FIG. 4H shows a bar chart of percentages of nuclei with FISH probe colocalization in normal (n=213) and in HS cells (n=150). FIG. 4I shows a complexity histogram of chromatin complexes. FIG. 4I, top:

RAIDs are binned at 5 Kb resolution and the number of bins covered by each chromatin complex in RNAPII ChIA-Drop data is counted. Individual distributions across each RAID are averaged, with the heights indicating the means and the error bars indicating one standard deviation. The gray bar shows an expected random distribution based on a binomial model. FIG. 4I, bottom, as above, but using ChIA-Drop data in TADs. Chromatin complexes from RNAPII ChIA-Drop in RAIDs show lower complexity than expected (more constrained), while chromatin complexes from ChIA-Drop in TADs show higher complexity than expected. FIG. 4J shows the heterogeneity of chromatin complexes within genomic domains. FIG. 4J, upper panel, within each domain (RAIDs for RNAPII-enriched ChIA-Drop data and TADs for ChIA-Drop data), the heterogeneity of chromatin complexes over the same bins as in (panel i) is computed by the normalized Shannon entropy. A value of 1 indicates that all the chromatin complexes within the domain are different, and a value of 0 indicates all the chromatin complexes within the domain are the same (statistic=0.95, p-value<2.2e-16; two-sided K-S test). FIG. 4J, lower panel, the heterogeneity within RAIDs is computed for chromatin complexes from RNAPII-enriched ChIA-Drop specifically involving active gene promoters. The heterogeneity of active genes within RAIDs was also computed for single-cell RNA-seq data (statistic=0.27, p-value=2.4e-13; two-sided K-S test).

FIG. 5A shows a bar chart showing the number of chromatin complexes that involve one promoter (1P), two promoters (2P), three promoters (3P), or four or more promoters (≥4P). FIG. 5B shows a browser view of a segment in chr2R (377 Kb) with a number of active and inactive genes, including the active gene luna. FIG. 5B, from top to bottom: RNA-Seq track shows the expression level of genes by strand (plus strand: green and upward; minus strand: blue and downward); RNAPII ChIA-PET loops and binding coverage (blue); RNAPII ChIA-Drop loops and binding coverage; RNAPII ChIA-Drop promoter-linked chromatin complexes (n=592) are depicted in a linear multi-fragment view with bright green dots for promoter-involving fragments, and dark green dots for non-promoter fragments; Two promoter (2P) involved complexes (n=98); Three promoter (3P) involved complexes (n=10). Fragments in the same complex are connected by gray horizontal lines. FIG. 5C shows among the chromatin complexes involving three promoters (3P), different subgroups were identified based on expression levels of the three genes. FIG. 5C, top, each chromatin complex is displayed as a dot, arranged by similarity (via dimensionality reduction). Colors denote the clusters. FIG. 5C, bottom, boxplots display distributions of epigenomic features. For each chromatin complex, the three genes are sorted in increasing order, such that the three columns in each set of boxplots correspond to these three sorted genes across complexes. Clusters I and II are imbalanced transcription (one or two dominant promoter(s) and one or two enhancer-like promoter(s)), and clusters III and IV are co-transcription. In the RNA-Seq boxplot (y-axis is "expression RPKM" value), only the 3Ps in cluster III do not have significant difference (Kruskal-Wallis test p-value=0.043, marked as *), p-values of other clusters are all <2.2e-16 (marked as ****). The other y-axis units are "cell count" for scRNA-Seq, "max coverage" for RNAPII and H3K4me3 ChIA-Seq data, and "ratio" for H3K4me1/me3. FIG. 5D shows an aggregation plot of RNAPII ChIA-Drop data showing the average chromatin contact profile over all active genes (plus-strand genes in the upper panel in green, and minus-strand genes in the lower panel in gray). First, RNAPII ChIA-Drop data is converted to pairwise loops. Then, promoter-involving loops are averaged over genes (aligned by percentile binning). Genome-wide, the promoter-involving loops show a directionality bias toward the gene body, and extend along the entire gene body. FIG. 5E shows a 2D contact map of RNAPII ChIA-PET data at the luna gene locus showcases a clear chromatin contact "stripe" from the promoter into the gene body, consistent with the genome-wide average in FIG. 5D. FIG. 5F shows promoter-involving chromatin complexes from RNAPII ChIA-Drop data are displayed in linear multi-fragment view. There were 72 luna promoter-linked chromatin complexes that extend into the gene body. Inset: A one-sided extrusion model for chromatin looping structures during gene transcription. At the pre-initiation stage, a protein cluster of RNAPII and co-factors are loaded at the promoter site. When transcription starts, the DNA template is pulled through the RNAPII machinery. As transcription extends, the extruded chromatin loops begin folding, with possible specific and random contacts proximal to RNAPII protein cluster. Yellow circles, RNAPII; P, promoter at TSS; gray line, chromatin DNA; dotted arrow, moving direction; red octagon, TES; blue line, transcribed product.

FIG. 6A-G provides data from embodiments of ChIA-Drop method optimization. The efficiency of the microfluidics system for chromatin DNA barcoding and amplification was characterized by MiSeq sequencing data. Each test generated 2-4 million sequencing reads. The numbers of captured GEM barcodes, the percentages of uniquely mapped reads, and the read length distribution are presented for data quality assessment. FIG. 6A shows pure DNA versus chromatin DNA. Both pure DNA and chromatin DNA templates were prepared from the same chromatin sample. The chromatin sample was prepared by in situ HindIII digestion followed by sonication for nuclear lysis. The chromatin DNA used for test was still in crosslinked state, and some DNA positions were bound by protein component. The pure DNA was purified from the chromatin fragment after de-crosslinking. The length of the DNA templates were about 3,000 bp. Most of the pure DNA sequencing reads were in maximum length (130 bp), of which 96% were mappable. The chromatin DNA yield 59% mappable reads. FIG. 6B shows a distance density comparison of pure DNA and chromatin DNA. The relative probability densities of the log 10 of fragment-to-fragment distances in a GEM are plotted, categorized by the fragment number per GEM (F #), color code blue-green-red for fragment F=2, F=3, up to F=11. Both pure DNA (FIG. 6B, left) and chromatin DNA (FIG. 6B, right) data are plotted on the same scale. To be noted, the low-fragment-containing GEMs showed the similar distributions as the pure DNA, whereas the chromatin DNA with high-fragment-containing GEMs displayed different patterns. FIG. 6C shows a 2D heatmap comparison of pure DNA (HindIII, 6-bp cutter), chromatin DNA (MboI, 4-bp cutter and HindIII). The pure DNA data show random interactions and lack chromatin topological structures; the MboI chromatin DNA data exhibit little structures, and HindIII chromatin DNA data show rich chromatin contact structures. FIG. 6D shows chromatin fragment length by different fragmentation methods. Chromatin sample digested by 4 bp-cutter (MboI, ~300 bp) or 6 bp-cutter (HindIII, ~3000 bp), or sheared by sonication (~6000 bp) were prepared accordingly. The longer chromatin fragments (3,000-6,000 bp) generated more mappable DNA sequencing reads (≥50 bp) than the shorter fragments. FIG. 6E shows summary statistics of GEMs from chromatin libraries prepared by MboI and HindIII digestion. The read statistics between the two libraries are comparable under the same loading amount, but the fragment histograms of GEMs are different. The HindIII data generated more uniquely mappable reads and more high-fragment-containing GEMs than the MboI data, contributing to the chromatin structures shown in FIG. 6C. FIG. 6F shows chromatin sample loading by different input quantity. Input chromatin DNA of 0.5 ng performed well. When input was too low (i.e., 0.5 pg), the majority of the sequencing reads were only 19-20 bp (barcode primer sequence), indicating that most droplets lack chromatin materials. FIG. 6G shows an interspecies chromatin experiment. Chromatin samples of *Drosophila* S2 and human GM12878 cells were mixed in equal number of cells or in equal quantity of chromatin DNA. Barcoded sequencing reads were mapped to each reference genome. Reads with the same GEMbarcode were grouped as a GEM. GEMs with fly-only, human-only, or mixed reads were identified. The ratio of mixed GEMs over the total GEMs is an approximate likelihood of a mixed chromatin complex in a droplet. When tested with equally mixed numbers of cells, the number of GEMs with chromatin fragments of human origin is 20-fold more than GEMs of *Drosophila* origin (181,956/9,149=19.89), which reflect the ratio of human to *Drosophila* genome lengths (hg 3,000 Mb/dm 175 Mb=17.14). Notably, in the test with equal chromatin mass, the GEMs with mixed origins of fragments were only 5.1%, indicating a small proportion of droplets with mixed chromatin samples.

FIG. 7A shows whole chromosome (chr2R) view of 2D contacts for two ChIA-Drop replicates (Rep1 and Rep2). The reproducibility of the two replicates in this region was quantitatively assessed by insulation score (Spearman correlation coefficient=0.83) and HiCRep (scc=0.85). FIG. 7B shows genome-wide reproducibility assessment of ChIA-Drop and RNAPII ChIA-Drop. To best assess the data quality and reproducibility, a comprehensive comparison was conducted between 4 datasets (ChIA-Drop, Hi-C, RNAPII ChIA-Drop, and RNAPII ChIA-PET), each with two replicates for reproducibility analysis using HiCRep. Each row and column represents the 8 datasets of interest, and the entry indicates the correlation coefficient ('sec' output from HiCRep) between the corresponding row and column. The entries are color-coded by their values, with darker colors for higher values. FIG. 7C shows a scatter plot of insulation scores between ChIA-Drop replicates. The insulation scores are computed genome-wide for both replicates of ChIA-Drop and the values are plotted, with Spearman correlation coefficient=0.83. FIG. 7D shows a browser view of AB compartment and TAD of ChIA-Drop and Hi-C data. For a given 1.2 Mb window, ChIA-Drop and Hi-C data heatmaps are presented along with their TADs (triangle) and A (light orange)/B (grey) compartments by eigenvectors, and histone ChIP-seq tracks. Both ChIA-Drop and Hi-C data exhibit similar patterns. FIG. 7E shows epigenomic patterns in A and B compartments. Each of the A and B compartments is binned to 300 bins and are extended by 100 bins on both ends. The average RPM values of H3K27ac and H3K27me3 ChIP-seq signals are plotted. FIG. 7F shows partitioning of *Drosophila* genome by TAD and Gap for ChIA-Drop and Hi-C data. ChIA-Drop and Hi-C data were hit to previous called TADs 22 and they were highly enriched at TADs and overlapping (>90%). H3K27ac and H3K27me3 ChIP-seq signal densities are plotted separately for TAD and Gap regions called with Hi-C data 22. H3K27me1 signals (active marks) were more enriched in Gaps, and H3K27me3 (repressive mark) were concentrated in TADs. TADs also called by insulation score for both the ChIA-Drop and Hi-C data with identical parameters, see detail in Examples 2 and 3. FIG. 7G shows TAD size distribution. From Hi-C and two replicates of ChIA-Drop data, TADs are called via insulation scores. The resulting densities of TAD sizes (lengths) are plotted, with a peak at 142 Kb for all three datasets.

FIG. 8A shows a 2D contact map of two replicates of ChIA-Drop data. A 10 Mb region is shown for two replicates in contact heatmaps. HiCRep correlation coefficient, scc=0.79. FIG. 8B shows decomposition by fragment number. Both replicates in panel (a) are further decomposed into small complexes with 2-5 fragments (F=2-5/GEM) and large complexes with more than 5 fragments (F>5/GEM). The patterns are consistent between replicates: large complexes contribute more to the TAD structures than small complexes. HiCRep correlation coefficient between replicates of large complexes scc=0.79; of small complexes scc=0.70. FIG. 8C shows distribution of contact distances by fragment size. The empirical cumulative distribution function (ECDF) of log 10 of contact distances support the observed pattern that small complexes have larger contact distances than large complexes, where the color bar scales from blue, green to red for fragments in ascending order. F #: Fragment number per complex.

FIG. 9A-J provides data from embodiments of ChIA-Drop validation by PacBio long-read sequencing and 4-color DNA FISH. FIG. 9A shows a comparison of ChIA-Drop and PacBio detected multiple chromatin complexes. In a given 270 Kb window, a linear fragment view of ChIA-Drop data shows clusters associated with TAD structures. A zoomed-in view displays the overlapping chromatin fragments from ChIA-Drop and PacBio complexes, with matching regions highlighted in light blue. Both complex data exhibit high level of heterogeneity. FIG. 9B shows a comparison of distributions of fragment number in chromatin complexes in PacBio and ChIA-Drop data. Both methods captured multiplex chromatin complexes at a single-molecule resolution. Under the same cost, PacBio sequencing generated less number of reads than ChIA-Drop sequencing using Miseq. With more reads, ChIA-Drop data show higher multiplexity in chromatin contacts than PacBio data. FIG. 9C shows ChIA-Drop data of chromatin contacts with multiple fragments were shown in pairwise 2D contact map, complex cluster, and fragment views in this region. The same region was studied by Szabo and colleagues (25) using 3D super-resolution DNA-FISH (3D-SIM), with three probes (1 'green', 2 'red', 3 'blue') designed to test intra-TAD contacts (probe 1-2) and inter-TAD contacts (probe 1-3, 2-3, and 1-2-3). ChIA-Drop detected all combinations possible pairwise and 3-way contacts, and the number of GEMs are shown. FIG. 9D shows ChIA-Drop contact frequencies between the 3 loci are plotted. The highest contacts were between the intra-TAD loci 1 'green' and 2 'red'. The 3 other combinations of inter-TAD were low at the same level. The intra-TAD and inter-TAD contact frequencies matched with the physical distances of the three loci as measured by 3D-SIM. More specifically, individual GEMs contained fragments that overlap the 3 probed loci were detected, validating ChIA-Drop for detecting multiplex chromatin contacts. FIG. 9E shows a diagram of Hox genes cluster BX-C (bithorax complex, comprises three Hox genes, Ubx, abd-A, and Abd-B). The pairwise chromatin contacts between Fab-7/Abd-B and Fab-7/abd-A were shown by 2-color FISH in S2 cells but not in S3 cells (Bantignies and Cavalli, 2014). The three loci, bxd, Fab-7 and the Abd-B promoter (Pm), were used to make fluorescent DNA probes as shown. Fab-7 and bxd are separated by approximately 130 kb, Fab-7 and Abd-B Pm by approximately 70 kb. Gene Antp in another Hox gene cluster ANT-C (Antennapedia complex) approximately 10 Mb away from BX-C was also included for a fluorescent probe to provide a nuclear position point in FISH experiment. An arrow indicates gene orientation, square with orange color indicates promoter regulatory elements (PRE), and the colored circle dots represent DNA probes with corresponding colors. FIG. 9F shows four-color FISH in Drosophila S2 cells (nuclei, n=179). The three loci (Abd-B, Fab-7, and bxd) were colocalized, and the probe for Antp locus provided spatial nuclear position. The scale bar is either 2 μm or 1 μm as indicated. Right side is zoom-in view of the left side. FIG. 9G shows four-color FISH in Drosophila S3 cells (nuclei, n=76). The three loci (Abd-B, Fab-7, and bxd) were notably not colocalized, revealing topological structure of this Hox gene cluster. Same as in S2 cell, the probe for Antp locus provided spatial nuclear position. FIG. 9H shows curves of spatial distances (μm) between pairs of probes measured by Imaris image analysis software. The modes of the distances of Abd-B to Fab-7 is 0.24 μm in S2 cells (n=179) and 0.3 μm in S3 cells (n=76), respectively. The modes of the distances of Fab-7 to bxd is 0.28 μm in S2 cells, and 0.41 μm in S3 cells, respectively. The modes of the distances of Fab-7 to Antp, are larger than 1.81 μm in both cells. FIG. 9I shows histograms of the ChIA-Drop-identified chromatin contacts at the Hox gene locus between Abd-B to Fab-7, Fab-7 to bxd, and Abd-B to Fab-7 to bxd together simultaneously. FIG. 9J shows histograms of proportions of nuclei that were detected colocalization at loci between Abd-B to Fab-7, Fab-7 to bxd, and Abd-B to Fab-7 to bxd together simultaneously. When spatial distance cutoff at 0.24 μm, the detected nuclei with colocalization in S2 cells (n=179) shows more than S3 cells (n=76).

FIG. 10A shows a comparison of 2D contact maps between ChIA-Drop and RNAPII ChIA-Drop replicates (Rep1 and Rep2) in a 1.8 Mb segments in chr 3L. TADs called by ChIA-Drop are shown in 2D contact maps. Tracks of histone marks H3K27ac, H3K27me3 and RNA-Seq depict the active and inactive regions. Complex Cluster of RNAPII ChIA-Drop data shows at the bottom. Notably, contact signals in RNAPII ChIA-Drop data were enriched in active regions but reduced in inactive regions. FIG. 10B shows distribution of contact distances by GEM complexity of fragment numbers. The empirical cumulative distribution function (ECDF) of log 10 of contact distances support the observed pattern that small complexes have larger contact distances than large complexes. Color scales for each curve were from the spectrum of blue to green to red for fragment numbers 2 to 20 to 50 in ascending order. F #: Fragment number per complex. FIG. 10C shows a basic browser view in a 37 Kb window (chr2R:5,423,000-5,460,000) to display the loops and peaks from two replicates of RNAPII ChIA-Drop data as pairwise mapping. Multiple ChIA-Drop fragments (n=79) of chromatin complexes (n=26) were shown in the bottom panel. FIG. 10D shows a scatter plot showing the peak correlation between two replicates inside RAID regions. Spearman correlation coefficient r=0.92. FIG. 10E shows a Venn diagram showing the loop anchor overlapping between two replicates inside RAID regions. Loop numbers with PET counts cutoff were indicated.

FIG. 11A-F provides data from embodiments of RNAPII ChIA-PET data characterization. FIG. 11A shows correlation of RNAPII ChIA-PET data between replicates. Scatterplot shows two replicates of RNAPII ChIA-PET data, peak coverage (RPM, left), loops frequency (RPM, middle), and 2D contact map (100 kb/bin, RPM, right). Pearson correlation coefficient r is computed. FIG. 11B shows loop span distribution by PET counts. The interaction loop spans are recorded separately by the PET counts and their distributions are plotted. Those with high PET counts tend to have shorter loop spans than those with low PET counts. Color code indicates PET counts. FIG. 11C shows mixture model for loop span. The population of loops is separated into mid-range interaction (red) and long-range interaction (green) classes through the Gaussian mixture model. Dotted line shows the marginal distribution of the $\log^{10}$ (loop span) for loops with ≥4 PET counts, and 100 Kb is a cutoff threshold. FIG. 11D shows relationship between loop size and PET counts with respect to RAIDs. Loops are categorized to be intra-RAID if both anchors are in the same RAID and inter-RAID if they span two different RAIDs. The log of loop size and log of PET counts are plotted, with colors indicating the two categories. FIG. 11E shows a browser view. A 737 Kb region is presented along with RAIDs, epigenomic-defined states (color codes indict 9 chromatin state), and various ChIP-seq and RNA-seq signal tracks. Daisy-chain like loops tend to be clustered inside a RAID, but long-range inter-RAID loops also exist. FIG. 11F shows characteristics of RAIDs. The lengths, number of PETs in loops (n indicates loop number), and number of genes in RAIDs are all plotted as histograms and density lines.

FIG. 12A-G provides data from embodiments of RNAPII ChIA-PET and ChIA-Drop comparison. FIG. 12A shows 2D contact maps comparison. The 2D contact maps of RNAPII ChIA-PET (lower left) and RNAPII ChIA-Drop (upper right) are displayed at multiple resolutions (whole chromosome 2R, a 10 Mb segment, and a 2.5 Mb domain). Dotted circles highlight the long-range loops identified by both methods. FIG. 12B shows loops, peaks and fragment visualization. In a 63 Kb window in chr2R, the RNAPII ChIA-PET loops and peaks are similar for Kc167 and S2 cell lines. Moreover, the RNAPII ChIA-Drop data in loop and peaks view are in high concordance with the RNAPII ChIA-PET loops in S2 cells. Individual complexes with multiplex fragments show further details of RNAPII ChIA-Drop data. C #: complex number; F #: fragment number. FIG. 12C shows peak correlation. Taking all peaks called by RNAPII ChIA-PET and RNAPII ChIA-Drop inside RAIDs, the signal density in RPM are plotted in log 10 scale. Pearson correlation coefficient r=0.69. FIG. 12D shows loop count correlation. The number of loops in corresponding 476 RAIDs identified in RNAPII ChIA-Drop and RNAPII ChIA-PET data were counted for each RAID. The loop counts of each RAID were plotted. The Pearson correlation coefficient r=0.85. FIG. 12E shows loop anchor correlation. Venn diagram showed that 82.9% of the RNAPII ChIA-PET loops with PET ≥3 within RAIDs overlapped with 60.5% of the RNAPII ChIA-Drop loops with PET ≥4 inside RAIDs. FIG. 12F shows promoter-to-promoter correlation. For each gene promoter, the number of interactions with another promoter were counted in both RNAPII ChIA-PET and RNAPII ChIA-Drop data. The scatterplot is in $\log^{10}$ scale. The Pearson correlation coefficient r=0.76. FIG. 12G shows promoter-to-enhancer correlation. Each gene promoter is evaluated for its interactions with enhancers (i.e., 'non-TSS') and the counts are correlated (Pearson correlation coefficient=0.71).

FIG. 13A shows a browser visualization. RNAPII ChIA-Drop complexes are converted to ChIA-PET-like loops (green) (see Example 2) and are visualized along with RNAPII ChIA-PET loops (blue). At the loop level, both datasets are comparable. However, the linear alignment view displays highly heterogeneous interactions in ChIA-Drop complexes, with most binding to only one promoter and small portion connecting multiple promoters. FIG. 13B shows single cell RNA-seq (scRNA-Seq) and bulk cell RNA-Seq correlation. Using the RPKM of single cell RNA-seq cell and bulk RNA-Seq expression level for genes in S2, the two sets of numbers are plotted in log 10 scale (Spearman correlation coefficient=0.72). FIG. 13C shows single cell RNA-seq (scRNA-Seq) and bulk cell RNA-Seq visualization. The bulk RNA-seq expression level and the scRNA-seq expressed level (accumulated) show similar profile. FIG. 13D shows bias towards active genes in RNAPII ChIA-Drop. The number of chromatin complexes (GEM) overlapping with active and inactive gene promoters inside RAIDs are recorded and are normalized by the number of unique isoforms (see Methods in Examples). The boxplot shows a preference towards active genes, with green lines as medians and whiskers at ±1.5 inter quartile range. *: p<2.2e-16; two-tailed Mann-Whitney U test. FIG. 13E shows bias towards active genes in RNAPII ChIA-PET. Instead of the GEM counts in ChIA-Drop (FIG. 13D), the coverage in ChIA-PET are recorded and normalized accordingly. The skew towards active genes are yet again observed, with blue lines as medians and whiskers at ±1.5 inter quartile range. *: p<2.2e-16; two-tailed Mann-Whitney U test.

FIG. 14A-E provides data from embodiments of examples of RNAPII ChIA-Drop data. FIG. 14A shows promoter-centric view of RNAPII ChIA-Drop complexes at the 188 kb region with 28 genes including lilli, a large gene with 65 Kb. This region contains 518 promoter-linked complexes including one-promoter complexes (1P complexes, n=425), two-promoter complexes (2P complexes, n=89), and three-promoter complexes (3P complexes n=4). 2P and 3P complexes are shown in the lower panel. FIG. 14B shows 3-gene complex with one dominant gene. RNAPII ChIA-drop connected promoters of 3 genes RpL28, CG12078, and ckd. Based on the RNA-seq and histone marks, only RpL28 displays active behaviors. The expression level (in RPKM) of the three genes are shown as a bar chart. FIG. 14C shows 3-gene complex with three dominant genes. All three genes, CG1115, Kat60, and CG12713 simultaneously captured are active (expression level on the right). FIG. 14D shows 3-gene complex with two dominant genes. Only Aats-asp and NAT1 are active, with Mdr49 potentially playing the role of an enhancer (expression level on the right). FIG. 14E shows an example of intra-genic RNAPII ChIA-Drop data. At the lilli locus, processive promoter-linked multiplex chromatin contacts covering the entire gene body are shown. The number of fragments in a complex reflects potential looping complexity for the one-sided extrusion model in transcription.

FIG. 15A shows a browser view of luna gene. Processive promoter-linked multiplex chromatin contacts covering the entire luna gene body are shown. Only a few chromatin contacts appear in the upstream of the luna gene, indicating the specific chromatin interactions in the direction of gene transcription. FIG. 15B shows a browser view of shn gene. Similar to luna, the shn locus displays processive promoter-linked multiplex chromatin contacts. Also, 2D contact maps of RNAPII ChIA-PET show chromatin contact "stripe" pattern supporting the RNAPII ChIA-Drop data. FIG. 15C shows processive promoter-linked multiplex chromatin contacts at the mam locus. FIG. 15D shows processive promoter-linked multiplex chromatin contacts at the locus of Nipped-A and d4 genes in the opposite transcription direction.

FIG. 16A shows the pipeline for mapping, analyzing, and visualizing ChIA-Drop data. FIG. 16B is a flowchart of the read alignment, GEMcode identification, and GEM calling steps in ChIA-DropBox. FIG. 16C is a flowchart that illustrates that a strategy for ChIA-Drop has two levels: i) domain-based distance test to identify significant complexes contributing to the intra-TAD (domain) interactions; ii) frequency-based binomial test to assess inter-TAD contacts by using TAD as a unit and observing frequent interactions among TADs.

FIG. 17A provides a flowchart of process for calling significant chromatin complexes in an embodiment of ChIA-Drop method. FIG. 17B provides a diagram illustrating identification of multiplex complexes potentially included in one droplet to which significance (p-values) is assigned to each putative complex (PC). FIG. 17C is a diagram showing an example of a frequency-based binomial test (for inter-TAD interactions).

FIG. 18A shows an embodiment of a means for GEM classifications. S for Singleton of one chromosome: MS for mixed singletons of multiple chromosomes; C for complex of chromosome; CS for C with singleton; MC for mixed complexes of multiple chromosomes; and MCS for MC with singletons. FIG. 18B is pair of graphs illustrating in an embodiment of ChIA-Drop data that following significant calling, there is a shift in the density curve and that the fragment to fragment distances are much shorter for significant complexes than that in the original putative complexes (PCs). FIG. 18C shows five contact maps of processed chr2R: 3 Mb-4.8 Mb with 5 kb resolution using balanced normalization. FIG. 18D are two histograms of PC counts in the "significant" (left histogram) and "insignificant (right histogram) categories showing that in general, frequent interactions (high PC counts) are called significant and infrequent interactions (low PC counts) are called insignificant.

FIG. 19A shows heatmap results and FIG. 19B shows loop views.

FIG. 23A illustrates TAD hypothetical example and FIG. 23B illustrates RAID hypothetical example.

FIG. 25A shows a flowchart of a domain-based algorithm developed to consider the genomic distances among the fragments within a given putative complex (PC). FIG. 25B is a flowchart of steps in an entropy filter to computationally correct for the droplet contamination, wherein an undesired phenomenon of a droplet contain more than one chromatin complex is identified.

FIG. 26 shows a flowchart for visualization of the ChIA Drop data.

BRIEF DESCRIPTION OF THE SEQUENCES

Figure 2A:
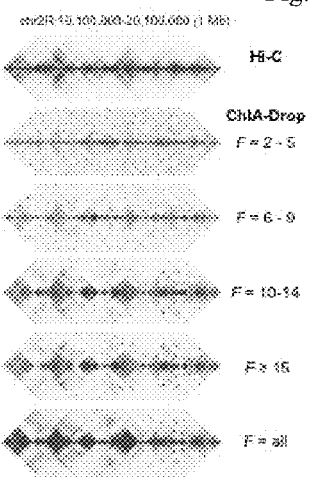
FIG. 2A-F provides data from embodiments of ChIA-Drop identified multiplex chromatin interactions.

SEQ ID NO: 1 is a GEMcode ID tag sequence: tacttgttcttgtatc.

DETAILED DESCRIPTION

The invention in part, includes a droplet-based and barcode-linked sequencing strategy for multiplex chromatin interaction analysis (ChIA-Drop) with single-molecule precision. In ChIA-Drop, crosslinked and fragmented chromatin sample is directly applied to a microfluidics system, and each chromatin complex is compartmentalized in a Gel-bead-in-Emulsion (GEM) droplet that contains unique DNA oligonucleotides and reagents for linear amplification and barcoding of chromatin DNA templates. The barcoded amplicons with GEM-specific indices can then be pooled for standard high-throughput sequencing, and the sequencing reads with identical barcodes are assigned to the same GEM of origin, implying that they are derived from the same chromatin complex. Mapping of the DNA sequencing reads to the reference genome identifies which remote genomic loci were in close spatial proximity. Based on these mapped loci, multiplex chromatin interactions can be detected (FIG. 1A).

The invention in part, includes a droplet-based and barcode-linked sequencing strategy for multiplex chromatin interaction analysis (ChIA-Drop) with single-molecule precision. In ChIA-Drop, crosslinked and fragmented chromatin sample is directly applied to a microfluidics system, and each chromatin complex is compartmentalized in a Gel-bead-in-Emulsion (GEM) droplet that contains unique DNA oligonucleotides and reagents for linear amplification and barcoding of chromatin DNA templates. The barcoded amplicons with GEM-specific indices can then be pooled for standard high-throughput sequencing, and the sequencing reads with identical barcodes are assigned to the same GEM of origin, implying that they are derived from the same chromatin complex. Mapping of the DNA sequencing reads to the reference genome identifies which remote genomic loci were in close spatial proximity. Based on these mapped loci, multiplex chromatin interactions can be detected (FIG. 1A).

In certain aspects of the invention methods of determining a chromatin interaction at a single molecule level are provided. As used herein the term "determining" used in relation to a chromatin interaction means identifying chromatin interactions at the single-molecule level. The ability to identify such interactions at the level of single molecules provides an advantage over prior pairwise, composite methods such as Hi-C and ChIA-PET methods. Methods of the invention have been used to confirm the presence of simultaneous multiplex chromatin interactions on the same chromatin string, and that the chromatin complexes within the same topological domains are highly heterogeneous, indicating a high level of variation in chromatin contacts at the single molecule level in cells. In addition, methods of the invention comprising RNAPII-enriched ChIA-Drop methods can be used to assess involvement of regulatory elements including gene promoters and enhances on single chromosomes.

Certain embodiments of methods of the invention include contacting a population of chromatin complexes with a plurality of barcode substrates, wherein each individual substrate includes multiple copies of a unique DNA barcode of nucleotides. The contact of the chromatin complexes with the barcode substrates results in a population of barcoded chromatin complexes.

Chromatin Preparation

In some embodiments of the invention, a sample used in a ChIA-Drop method is obtained from a crosslinked, permeabilized cell nucleus, which is digested to provide a population of chromatin complexes. A chromatin complex is comprised of chromatin DNA and chromatin protein. Methods of crosslinking a cell nucleus are known in the art, and in certain embodiments of the invention, a ChIA-Drop method includes use of live cells, such as tissue culture cells or cell isolated from freshly dissected tissues. In certain embodiments, the cell nucleus of the live cell is cross-linked using a fixative such as one or more of formaldehyde- and EGS (Ethylene glycol bis[succinimidylsuccinate]). Other similar crosslinking reagents suitable for crosslinking protein-DNA, protein-RNA and/or protein-protein (e.g., those having two or more reactive chemical groups suitable for reacting with the amide and/or thiol groups) may also be used. If EGS is used, a spacer region between the two NETS-esters may be a 12-atom spacer, although longer or shorter spacers (e.g., 6, 7, 8, 9, 10, 11, 12, 13, 14, 15, 16, 17, 18, 19, 20 atom spacers) may be used as well. If formaldehyde or EGS (typically about 1-2 mM, or 1.5 mM) are used, EGS may be added first followed by (about 1%) formaldehyde. Reaction may be quenched by glycine. Alternatively, about 1% formaldehyde or about 1% glutaraldehyde may be used. In a non-limiting example, about $1-2\times10^8$ live tissue culture cells or isolated cells are collected and cross-linked with EGS with shaking for 40 min., then contacted with formaldehyde (final concentration of about 1%) for 10 minutes at room temperature. In some aspects of the invention, the formaldehyde is greater than 0.5% (w/v) formaldehyde. In certain embodiments the formaldehyde is about 1% (w/v) formaldehyde.

An alternative cross-linking means that may be used in certain embodiments of the invention comprises UV cross-linking. In a non-limiting example, tissue culture cells may be UV-crosslinked at about 150 $mJ/cm^2$ at 254 nm, a non-limiting example of which is a UV crosslinker, such as STRATALINKER® UV crosslinker. Additional art-known means of cross-linking may also be suitable for use in an embodiment of the invention. Cross-linking methods are described, see for example: Li, X, et al., *Nat. Protoc.* 2017 May: 12(55):899-915; US Patent Pub. 2016/0177380; and Belton, J. et al. *Methods,* 2012 November: 58(3), the content of each of which is incorporated herein by reference in its entirety by reference.

Following cross-linking of the nucleus, the cross-linked nucleus is permeabilized using a methods such as contact with SDS or other suitable agent. In some embodiments, a proteinase inhibitor and/or RNase inhibitor may be added to the sample to prevent non-specific proteinase or RNase digestion. Cell lysis is then carried out using a suitable lysis buffer, a non-limiting example of which includes SDS. For example, a lysis buffer may comprise: 50 mM HEPES, 1 mM EDTA, 0.15 M NaCl, 1% SDS, 1% Triton X-100, and 0.1% sodium deoxycholate. Other suitable lysis buffers may also be used and are known in the art. See for example: Li, X, et al., *Nat. Protoc.* 2017 May: 12(55):899-915; US Patent Pub. 2016/0177380; and Belton, J. et al. *Methods*, 2012 November: 58(3), the content of each of which is incorporated herein by reference in its entirety by reference.

In some embodiments of the invention, chromatin fragments are generated by physical shearing, such as sonication, hydroshearing, or repeated drawing through a hypodermic syringe needle. Sonication means may be used to break up chromatin fibers. In some embodiments of the invention chromatin fragments may be generated using restriction enzyme digestion, or partial or limited endo- and/or exo-nuclease digestion. Various different commercially available instruments are suitable for sonication. For example, the 5220 Focused-ultrasonicator from Covaris, Inc. utilizes the Adaptive Focused Acoustics™ (AFA) technology for DNA, RNA, and chromatin shearing, and the BIORUPTOR® UCD-200 (Life Technologies Corp.) may also be used. After shearing, the chromatin may be diluted (for example, at least 2×, 3×, 4×, 5×, 6×, 7×, 8×, 9×, or 10 times) to lower the SDS concentration (for example, to about 0.1-0.5%). The extract may be cleared by centrifugation (a non-limiting example of which is at 14,000 rpm for 10 minutes at 4° C.). The resulting extract can be stored at −80° C. until use.

Following the sonication process the resulting material may be digested using one or more restriction enzymes. In some aspects of the invention the restriction enzyme is a 4 bp cutting enzyme such as, but not limited to: MboI. In certain aspects of the invention the restriction enzyme is a 6 bp cutting enzyme such as, but not limited to: Hind III. Additional art-known restriction enzymes may also be used in embodiments of the invention, for example, other 4 bp or 6 bp cutters, or other length cutters such as a 5 bp or 7 bp cutter, etc. One skilled in the art will be able to identify and use suitable alternative restriction enzymes in methods of the invention. In certain aspects of the invention, the digestion provides DNA fragments of 300-6000 bp in the chromatin complex.

Chromatin Sample Preparation for ChIA-Drop

A non-limiting example of a method of preparing a chromatin sample for use in a ChIA-Drop method of the invention is as follows, a process that is similar to sample preparation for Hi-C2, except the ChIA-Drop method does not include proximity ligation. In the example method: ~10 million cells were crosslinked for 10 min in 1% formaldehyde at room temperature. The crosslinked cells were quenched for 5 min in 0.125 M Glycine, and were then washed twice with DPBS twice. The crosslinked cells can be stored at −80° C. for later use or processed immediately with procedures for cell/nuclei lysis. For cell/nuclei lysis, crosslinked cells were suspended in 500 µl of cell lysis buffer (10 mM Tris-HCl pH 7.0, 10 mM Tris-HCl pH 8.0, 10 mM NaCl, 0.2% NP40, 1× Protease Inhibitor cocktail, Roche) and incubated at 4° C. for 30 min with rotation. The nuclei are isolated by centrifugation at 4° C. for 5 min at 2,500 relative centrifugal force. The nuclei pellet can be suspended in 100 µl of 0.5% SDS and incubated for 5 minutes at 62° C. to permeabilize the nuclear membrane. Following permeabilization, 285 µl of nuclease-free water and 25 µl of 20% triton X-100 can be added for and the mixture incubated for 15 min at 37° C. to neutralize SDS.

The permeabilized nuclei were then processed using in situ chromatin digestion. When digested by a 4 bp cutter MboI, 60 µl of NEB Buffer 2 is added to the permeabilized nuclei and mixed well. 55 µl of nuclease-free water and 75 µl of MboI (5 U/µl) can be added to the mixture. In embodiments in which a 6 bp cutter digestion HindIII is performed, 80 µl of nuclease-free water and 50 µl of HindIII (20 U/µl) can be added to set up the reactions. The reactions that included either the 4 bp cutter or 6 bp cutter are incubated overnight at 37° C. with constant agitation. The nuclei with digested chromatin materials are then sheared by sonication with 1× Protease Inhibitor cocktail to release the chromatin fragments. The DNA size range of the chromatin fragments generally was in the range of about 300-6000 bp, depending on restriction digestion. The final fragmented chromatin sample was then utilized for ChIA-Drop library construction.

Enriched Chromatin Population

In certain aspects of the invention, a population of chromatin complexes is an enriched population. In some aspects of the invention the chromatin complex population is enriched for a chromatin protein by incubating the population of chromatin complexes with a monoclonal antibody specific for the chromatin protein in order to form chromatin complexes bound to the monoclonal antibody. Different chromatin proteins may be of interest for enrichment, for example, though not intended to be limiting, the chromatin protein that is enriched is RNAPII, Retinoic acid receptor alpha (RARA), ER, or transcriptional repressor protein CTCF, also known as 11-zinc finger protein or CCCTC-binding factor. Other chromatin proteins may be of interest for enrichment and methods and monoclonal antibodies, or functional fragments thereof that are suitable for use in enrichment can be used in embodiments of the invention for chromatin protein enrichment. Following the binding of a monoclonal antibody of interest to the chromatin complexes, the bound chromatin complexes bound are isolated and the monoclonal antibody is removed, which results in a population of chromatin complexes in which each complex comprises the chromatin protein. As a non-limiting example of an enrichment process: 2 µg of a monoclonal antibody of interest that is specific for a chromatin component is bound to a substrate (for example protein G sepharose). The antibody-coated beads are incubated with the chromatin extract and the beads are washed. The resulting protein-DNA complexes are eluted from the beads with elution buffer and the eluent is then dialyzed to remove SDS.

Chromatin Sample Preparation for RNAPII ChIA-Drop

A non-limiting example of a method of preparing a chromatin sample for use in a RNAPII enriched ChIA-Drop method of the invention is as follows, a process that is similar to sample preparation for Hi-C2, except the method of the invention does not include proximity ligation. In the example, ~10 million cells are dual-crosslinked with 1.5 mM EGS for 40 min followed by 1% formaldehyde reaction for 20 min, and then quenched with 0.125 M Glycine (Promega) for 10 min, and washed twice with DPBS. After cell and nuclei lysis, the crosslinked chromatin material is fragmented by sonication to the size range of 6 kb. The fragmented chromatin sample is incubated overnight with 20 µl of anti-RNAPII monoclonal antibody bound on Dynabeads™ Protein G beads at 4° C. with rotation. RNAPII-enriched chromatin is released from Protein G beads by incubating for 30 min with EB Buffer containing 1% SDS at 37° C. with constant agitation. The elution supernatant is passed through Ultra Centrifugal Filter to remove remaining SDS. The chromatin preparation now is ready for ChIA-Drop library construction, or to be stored at 4° C. for later use. It will be understood that the above solutions and procedure is included as an example and that numerous other art-known buffers and procedures are suitable for use in enrichment methods of the invention.

ChIA-Drop Library Construction and Sequencing

Fragmented chromatin sample from regular of enriched chromatin samples prepared as indicated elsewhere herein, can be mixed with BSA to prevent chromatin aggregation. An aliquot of the chromatin sample is used to estimate the quantity of chromatin DNA by performing de-crosslinking and DNA purification (named as pure DNA), and the chromatin sample is then adjusted to a concentration of 0.5 ng/µl. GemCode Technology (10X Genomics, Pleasant, Calif.) is used for partitioning of individual chromatin complexes or pure DNA into droplets for chromatin DNA barcoding and amplification. For this procedure, the chromatin sample was mixed with Sample Master Mix from Chromium Genome v2 Library Kit & Gel Bead Kit (10X Genomics, San Francisco, Calif.), and input 0.5 ng chromatin mix was loaded into the Chromium Genome Chip (10X Genomics), which was placed in Chromium Controller to generate Gel bead in Emulsion (GEMs) droplets each containing unique barcoded DNA primers, chromatin DNA fragments, and enzymatic reagents. In certain embodiments of the invention, a GEM droplet each contains multiple copies of a DNA construct comprising a PCR priming site, a sequence reading site, a barcode, and a random priming nucleotide sequence. In some aspects of the invention the barcode is a 15 nt to 25 nt barcode or the barcode is a 16 nt to 20 nt barcode. In some embodiments of the invention the DNA barcode comprises ten or more nucleotides and in certain embodiments of the invention, the DNA barcode may include up to 8, 9, 10, 11, 12, or more nucleotides. In some embodiments of the invention, the random priming nucleotide sequence is a random 8-mer. In some embodiments of the invention the GemCode Technology manufacturer's instructions are used to assist in selection of one or more of: barcoded DNA primers, sequence reading site, one or more barcodes, and random priming nucleotide sequence. It will be understood that such elements can be selected using art-known methods and for use in methods of the invention. In some embodiments of the invention GemCode Technology manufacturer's instructions are used in procedures for DNA barcoding and sequencing aspects of the invention.

In certain embodiments of the invention the prepared GEMs can be incubated overnight in 30° C. isothermal incubation for amplification and barcoding of the chromatin DNA templates. In certain embodiments of the invention the amplifying step is performed by isothermal incubation at about 30° C. that is between about 6 and 20 hours in length, including all time ranges between 6 and 20. In some embodiments the length of the isothermal incubation is between 8 and 16 hours. Additional methods for example for amplification, are known in the art and may be suitable for use in methods of the invention. After the isothermal incubation, the barcoded DNA amplicons may be released from all GEMs. Purified DNA fragments are subjected to end repair, A-tailing, adaptor ligation and Sample Index PCR using reagents from Chromium Multiplex Kit (10X Genomics) following the manufacturer's instructions. The PCR products can be size-selected in the range of 600 bp, and the final ChIA-Drop library can then be analyzed by sequencing (2×150 bp) using MiSeq (Illumina) methods. The R1 reads that include GEMcode and genomic sequences can then be used for further analysis. In some embodiments of the invention, the sequencing is 150 bp sequencing and each sequence contains the barcode.

The above-described methods can be used to partition the population of barcoded chromatin complexes into droplets such that each droplet contains not more than one barcoded chromatin complex. Using methods of the invention, each barcoded chromatin complex comprises chromatin DNA that is ligated to multiple copies of the unique barcode. The chromatin DNA is then amplified and then released from the chromatin complex. The resulting chromatin DNA is then sequenced, which generates a plurality of DNA sequence reads. In some aspects of the invention the plurality of sequence reads are mapped to a referenced genome, which produces a genomic location of the sequence reads and can be used to generate a 3D genomic connectivity map. The resulting connectivity map can be used to assess the physical interaction between nucleic acids in the chromatin complex at a single molecule level.

Processing ChIA-Drop Data

Certain embodiments of the invention utilized the R statistical package (r-project.org/) for statistical analyses. Certain terminology used herein includes the term "gene promoter" which as used herein means a region that is ±250 bps of the Transcription Start Site (TSS) of a gene including all isoforms. As used herein a gene is indicated as "active" if its RNA-Seq expression level RPKM ≥1 and "inactive" if its RPKM ≤1. As used herein a promoter of an active gene is referred to as "active promoter" and that of an inactive gene is referred to as "inactive promoter". As included herein, all regions outside of gene promoter regions are "non-promoter" (or "enhancer") regions. Certain terms used herein including: "Topologically Associating Domain" and "RNAPII Associated Interaction Domain" are abbreviated as "TAD" and "RAID", respectively.

ChIA-DropBox Data-Processing Pipeline

As used herein a data processing pipeline, referred to as ChIA-DropBox, was developed and is comprehensive data-processing pipeline that can be used to convert ChIA-Drop raw reads into meaningful chromatin interaction data. Thus, in some aspects of the invention methods such as the ChIP-DropBox procedure may be used to analyze and map the sequenced chromatin DNA from which a plurality of DNA sequence reads have been generated.

As a first step in ChIP-Dropbox, reads are aligned to the reference genome (dm3) using the 10X Genomics longranger wgs pipeline (v2.1.5, see: //support.10xgenomics.com/genome-exome/software/pipelines/latest/using/wgs), from which GEMcodes are identified with pysam module (v0.7.5) in python (v2.7.13). Uniquely mapped reads with MAPQ ≥30 and read length ≥50 bp are extended by 500 bps from its 3' end, and those with the same GEMcode overlapping within 3 kb distance are merged using pybedtools (v0.7.10). Multiplexed intra-chromosomal GEMs are retained as potential chromatin complexes, and their statistical significances are estimated by comparing fragment distances to a null distribution of randomly rewired GEMs (see Examples section for more details). The ChIA-DropBox process also permits visualization of ChIA-Drop data in various types/formats: 1) 2D heatmap via Juicer tools (v1.7.5) and Juicebox (v1.9.0; v1.1.2); 2) pairwise loops; and 3) linear fragment alignments. Full details of ChIA-DropBox and ChIP-DropBox analysis that can be used in methods of the invention are provided in Examples 2 and 3, respectively. Additional processing methods were developed that can be utilized in embodiments of methods of the invention. Examples 1-3 provide details of methods that can be used for analysis of data obtained using the ChIA-Drop method. For example, Example 2 discloses a domain-based algorithm to consider the genomic distances among the fragments within a given putative complex (PC). Example 3 discloses an entropy filtering algorithm that can be used to computationally correct for the droplet contamination, for example when a droplet contains more than one chromatin complex. Additional procedures and methods for analysis and application of ChIA-Drop data that are encompassed by the invention are set forth in the Examples section.

EXAMPLES

Example 1

Methods
Cell Culture

Drosophila Schneider 2 (S2) cells (derived from a primary culture of late stage 20-24 hours old Drosophila melanogaster embryos) were cultured in Express Five® SFM (ThermoFisher Scientific) with 1:100 L-Glutamine (ThermoFisher Scientific) at 27° C. Drosophila S3 cells (derived from a primary culture of late embryonic stage) were cultured in Schneider's Drosophila Medium (Thermo Fisher Scientific, cat #21720024) with 12.5% HyClone™ Fetal Bovine Serum (U.S., Characterized, heat inactivated, Fisher Scientific, cat #SH3007103HI) at 27° C. Human GM12878 cells (a B-lymphoblastoid cell line produced from the blood of a female donor with northern and western European ancestry by EBV transformation) were maintained in RPMI 1640 supplied with 15% fetal bovine serum at 37° C. and ambient 5% $CO_2$ as described by the Coriell Institute of Medical Research. Cells at exponential growth phase were harvested for chromatin preparation.

Chromatin Sample Preparation for ChIA-Drop

The overall chromatin sample preparation for ChIA-Drop is very similar to sample preparation for Hi-C2, except no proximity ligation. In brief, 10 million cells were crosslinked with 1% formaldehyde at room temperature for 10 min, and quenched with 0.125 M Glycine (Promega) for 5 min, then washed with DPBS twice. The crosslinked cells can be stored at −80° C. for later use or immediately proceed for cell/nuclei lysis. The crosslinked cells were suspended in 500 µl of cell lysis buffer (10 mM Tris-HCl pH 7.0, 10 mM Tris-HCl pH 8.0, 10 mM NaCl, 0.2% NP40, 1× Protease Inhibitor cocktail, Roche) and incubated at 4° C. for 30 min with rotation. Then, the nuclei were isolated by centrifugation at 4° C. for 5 min at 2,500 relative centrifugal force. The nuclei pellet was suspended in 100 µl of 0.5% SDS and incubated at 62° C. for 5 min to permeabilize the nuclear membrane. After that, 285 µl of nuclease-free water and 25 µl of 20% triton X-100 were added for further incubation at 37° C. for 15 min to neutralize SDS. The permeabilized nuclei were then ready for in situ chromatin digestion. For digestion by 4 bp cutter MboI (cat #R0147L, NEB), 60 µl of NEB Buffer 2 was added and mixed well, then 55 µl of nuclease-free water and 75 µl of MboI (5 U/µl) were added, whereas for 6 bp cutter digestion HindIII (cat #R0104L, NEB), 80 µl of nuclease-free water and 50 µl of HindIII (20 U/µl) were added to set up the reactions. The incubations were taking place at 37° C. overnight with constant agitation. The nuclei with digested chromatin materials were sheared by sonication with 1× Protease Inhibitor cocktail to release the chromatin fragments. The DNA size range of the chromatin fragments usually was 300-6000 bp, depending on restriction digestion. The final fragmented chromatin sample was then preceded for ChIA-Drop library construction. If not immediately used, the chromatin sample should be stored at 4° C., and no longer than a week.

Chromatin Sample Preparation for RNAPII ChIA-Drop

The overall chromatin sample preparation for RNAPII enriched ChIA-Drop follows the ChIA-PET protocol30, except no proximity ligation. In brief, 10 million cells were dual-crosslinked with 1.5 mM EGS for 40 min followed by 1% formaldehyde reaction for 20 min, and then quenched with 0.125 M Glycine (Promega) for 10 min, and washed twice with DPBS. The crosslinked cells can be frozen and stored at −80° C. for later use. After cell and nuclei lysis, the crosslinked chromatin material was fragmented by sonication to the size range of 6 kb. The fragmented chromatin sample was incubated with 20 µl of anti-RNAPII monoclonal antibody (8WG16, cat #920102, Biolegend, San Diego, Calif.) bound on Dynabeads™ Protein G beads (cat #10009D, ThermoFisher Scientific) at 4° C. overnight with rotation. RNAPII-enriched chromatin was released from Protein G beads by incubating with EB Buffer containing 1% SDS at 37° C. for 30 min with constant agitation. The elution supernatant was passed through Ultra Centrifugal Filter (cat #UFC510024, Millipore) to remove the remaining SDS. The chromatin preparation now is ready for ChIA-Drop library construction, or stored at 4° C. for later use.

ChIA-Drop Library Construction and Sequencing

Fragmented chromatin sample was mixed with 50 µg/ml of BSA (cat #B9000S, NEB) to prevent chromatin aggregation. An aliquot of chromatin sample was taken to estimate the quantity of chromatin DNA by performing decrosslinking and DNA purification (named as pure DNA), and the chromatin sample was adjusted to the concentration of 0.5 ng/µl. GemCode Technology (10X Genomics, Pleasant, Calif.) was applied for partitioning of individual chromatin complexes or pure DNA into droplets for chromatin DNA barcoding and amplification. In brief, the chromatin sample was mixed with Sample Master Mix from Chromium Genome v2 Library Kit & Gel Bead Kit (cat #PN-120258), and input 0.5 ng chromatin mix was loaded into the Chromium Genome Chip (cat #PN-120257), which was placed in Chromium Controller to generate Gel bead in Emulsion (GEMs) droplets each containing unique barcoded DNA primers, chromatin DNA fragments, and enzymatic reagents. The GEMs were subjected to a 30° C. isothermal incubation for overnight for amplification and barcoding of the chromatin DNA templates. After that, the barcoded DNA amplicons were released from all GEMs. Purified DNA fragments were subjected for end repair, A-tailing, adaptor ligation and Sample Index PCR using reagents from Chromium Multiplex Kit (cat #PN-120262) following the manufacturer's instructions. The PCR products were size-selected in the range of 600 bp, and the final ChIA-Drop library was analyzed by sequencing (2×150 bp) using MiSeq (Illumina, San Diego, Calif.). The R1 reads that include GEMcode and genomic sequences were used for further analysis in this study.

RNAPII ChIA-PET Library Preparation and Sequencing

The RNAPII ChIA-PET libraries were performed as previously described (30). Briefly, dual-crosslinked Drosophila S2 cells were lysed followed by sonication to fragment the chromatin material. The fragmented chromatin sample was subjected for ChIP enrichment by anti-RNAPII monoclonal antibody. The RNAPII-enriched chromatin material was then subjected for ChIA-PET library construction, followed by paired-end-tag sequencing (2×150 bp) using Illumina MiSeq instruments. An improved ChIA-PET protocol, called in situ ChIA-PET, was also applied to generate RNAPII ChIA-PET libraries for S2 cells. Essentially, it applies an in situ restriction digestion of the chromatin fragment same as the in situ Hi-C protocol. The rest was performed using the standard ChIA-PET protocol (30).

Multiple Chromatin Contacts Detected by PacBio Long Read Sequencing

To validate that ChIA-Drop detects multiple chromatin interactions, long-read PacBio sequencing was performed on purified proximity-ligated chromatin DNA. The ligated chromatin DNA was prepared as Hi-C method and subjected for de-crosslinking and DNA purification, then for adapter ligation and sequencing using PacBio platform.

Single-Cell RNA-Seq

Fresh S2 cells were suspended at 1×106 cells per ml in 1×DPBS contained 0.04% BSA, then loaded on a GemCode Single-Cell instrument to generate single-cell GEMs using GemCode Single-Cell 3' Gel Bead and Library Kit (10X Genomics), the cDNA library was subjected for Illumina Hiseq4000 sequencing.

DNA-FISH Validation of ChIA-Drop Data

DNA fluorescence in situ hybridization (DNA-FISH) with 4 colors for three validation loci was performed with arbor biosciences probes (see Table 1 below) as previously described with a modification.

TABLE 1

Biosciences Probes

| Locus | Probe ID | Coordinate | Span | Fluorescent |
|---|---|---|---|---|
| 1 | Abd-B | Chr3R: 12778000-12800000 | 22 Kb | Atto-488 |
| 1 | Fab-7 | Chr3R: 12710000-12730000 | 20 Kb | Atto-647N |
| 1 | bxd | Chr3R: 12565000-12615000 | 50 Kb | Atto-550 |
| 1 | Antp | Chr3R: 2720000-2830000 | 110 Kb | Atto-594 |
| 2 | C1 | Chr2L: 7890000-7965000 | 75 Kb | ATTO-594 |
| 2 | C2 | Chr2L: 8250000-8300000 | 50 Kb | ATTO-647N |
| 2 | C3 | Chr2L: 8550000-8670000 | 120 Kb | Atto-488 |
| 2 | C4 | Chr2L: 8740000-8790000 | 50 Kb | ATTO-647N |
| 2 | C5 | Chr2L: 8890000-8940000 | 50 Kb | Atto-550 |
| 3 | R1 | Chr2L: 65000-145000 | 80 Kb | ATTO-549 |
| 3 | R2 | Chr2L: 250000-300000 | 50 Kb | ATTO-647N |
| 3 | R3 | Chr2L: 440000-580000 | 140 Kb | Atto-488 |
| 3 | R4 | Chr2L: 1085000-1185000 | 100 Kb | Atto-550 |

A cell suspension of $1.5 \times 10^6$/ml cells from *Drosophila* S2 or S3 were adhered to the coverslips coated with Poly-L-Lysine (Sigma, cat #P4707) for 30 min at 27° C., and heat shock (HS) treated S2 cells were then incubated at 37° C. for 20 min. The coverslips were fixed using 4% PFA (BosterBio, AR1068) for 10 min at room temperature, and cells were permeabilized with freshly made 0.5% Triton X-100 in DPBS for 5 min at room temperature, and then incubated with 100 μg/ml RNase A (Sigma, cat #R4875) for 1 hour. The coverslips were incubated in 20% Glycerol (Fisher Scientific, cat #3290-32) in 1×DPBS for 30 min and frozen in liquid nitrogen for approximately 30 s, and then thawed. Once the frozen layer disappears, the coverslips are put back to Glycerol, and the process is repeated twice. Subsequently, the coverslips are incubated in 0.1M HCl for 5 min followed by rinse three times in 2×SSC (Thermo Fisher Scientific, cat #AM9763) for 1 min, and incubated in 50% of Formamide with 2×SSC for at least 30 min at room temperature. Pre-denature DNA probes for 10 min at 80° C. and put them on ice until usage. The coverslips were taken out and drain off the excess of liquid, then turned cell-side down onto a 10 μl mixture of the pre-denature DNA probes in Hybridization Buffer (Empire Genomics), then the coverslips were covered and sealed with rubber cement to air-dry for at least 5 min at the room temperature. The coverslips and probe mixture were denatured for 3 min at 78° C., then incubated at 42° C. overnight in a dark and humidified chamber. The next day, the rubber cement is peeled off, and the coverslips are transferred to a 24-well plate and are washed three times with 2×SSC at 42° C. for 5 min, followed by three times wash with 0.1×SSC at 45° C. for 5 min; finally, they are rinsed twice in 1×DPBS. The coverslips were mounted by ProLong® Diamond Antifade Mountant with DAPI (ThermoFisher Scientific, P36966). Images were acquired by a Leica STED 3X/DLS confocal microscope with 100× objective and 1× or 8× Zoom factor using LasAF Software. The pinhole was set at 1 Airy unit. Images were obtained at 1,024×1,024 pixels with a scan speed of 600 Hz, frame average with 3. For each acquisition, about 12 Z-slices were taken, and all the images were acquired under the same parameter. The Z-stacks were projected with sum intensity projection and are displayed as represented images (FIG. 3-4, FIG. 9).

Computational Methods and Statistical Analysis

All statistical analyses in this study were performed using the R statistical package (www.r-project.org/).

Definitions and Abbreviations

Throughout this paper, the terminologies are defined as follows. A gene promoter region is ±250 bps of the Transcription Start Site (TSS) (40) including all isoforms, and a gene is labeled as 'active' if its RNA-Seq expression level RPKM ≥1 and 'inactive' if its RPKM <1. Promoter of an active gene is referred to as 'active promoter' and that of an inactive gene is 'inactive promoter'. All regions outside of the gene promoter regions are 'non-promoter' (or 'enhancer') regions. Common abbreviations are: Topologically Associating Domain (TAD), RNAPII Associated Interaction Domain (RAID).

ChIA-DropBox Data-Processing Pipeline

ChIA-DropBox is a comprehensive data-processing pipeline for converting ChIA-Drop raw reads into meaningful chromatin interaction data. First, reads are aligned to the reference genome (dm3) using the 10X Genomics longranger wgs pipeline (v2.1.5, https://support.10xgenomics.com/genome-exome/software/pipelines/latest/using/wgs), from which GEMcodes are identified with pysam module (v0.7.5) in python (v2.7.13). Uniquely mapped reads with MAPQ ≥30 and read length ≥50 bp are extended by 500 bps from its 3' end, and those with the same GEMcode overlapping within 3 kb distance were merged using pybedtools (v0.7.10). Finally, multiplexed intra-chromosomal GEMs are retained as potential chromatin complexes, and their statistical significances are estimated by comparing fragment distances to a null distribution of randomly rewired GEMs.

ChIA-DropBox also enables visualization of ChIA-Drop data in various types: 1) 2D heatmap via Juicer tools (v1.7.5) and Juicebox (v1.9.0; v1.1.2), 2) pairwise loops, 3) linear fragment alignments. Full details of ChIA-DropBox are provided in Example 2.

RNAPII ChIA-PET Data Analysis

RNAPII ChIA-PET data and in situ RNAPII ChIA-PET data derived from *Drosophila* S2 cells were processed following the established ChIA-PET pipeline30 (details in Example 3).

Calculation of Insulation Scores to Identify Topologically Associating Domains (TADs)

The insulation score was calculated (https://github.com/dekkerlab/crane-nature-2015) to call TADs23 (see Example 3).

Reproducibility Analysis of ChIA-Drop Data Using HiCRep

ChIA-Drop reproducibility was assessed with HiCRep (v1.2.0)41, which computes the stratum-adjusted correlation coefficient (scc) between two heatmaps (see Example 3).

Identification of RNAPII-Associated Interaction Domains (RAIDs)

Total 476 RAIDs were defined as described in Example 3.

Identification of Transcriptionally Active and Inactive Domains

Transcriptionally active and inactive domains are defined from the expression and two histone marks, by smoothing, segmenting (signal, changepoint packages in R), and concatenating (bedtools42 v2.26.0) and results in 708 active regions. Details are in Example 3.

Chromatin Fragments in ChIA-Drop Data Related to TADs

To relate the ChIA-Drop data to TADs defined by Hi-C data, multiplex chromatin complexes with fragments 6 or more (F≥6) were hit to TADs, and at least 3 chromatin fragments of a complex located in a TAD would be regarded as enriched in the TAD region. If an individual chromatin complex contained fragments overlapped with 2 or more TADs (at least 3 fragments in each TAD), it would be considered as crossing TADs. In the complexes (F≥6), 85% of them were enriched in 1 TAD, 11% of them were crossed 2 TADs and 4% were crossed multiple TADs.

Chromatin Fragments in RNAPII ChIA-Drop Data Related to RAIDs

The chromatin complexes (GEMs) with 3 or more fragments (F≥3) detected by RNAPII ChIA-Drop were hit to RAIDs defined by RNAPII ChIA-PET data. Similar to TADs, two categories were identified for RAIDs: GEMs contained fragments are all inside in one RAID (single), or overlap ≥2 RAIDs (crossed).

Loop Correlation in RAIDs

After ChIA-Drop chromatin complexes were identified using ChIA-Dropbox, the interactions were converted to pairwise contacts (BEDPE) for subsequent loop correlation analyses. These pairwise contacts are then input to the ChIA-PET pipeline "ChIA-PIPE", which clusters the pairwise contacts into loops and generated three major output files: loops (BEDPE), coverage (BEDGRAPH), and enriched peaks (BED; called by MACS v2.1.0). Next, the anchors of each loop are refined as follows. First, the "anchor point" is defined as the genomic location within the anchor that has the highest coverage. Second, each anchor of the loops is extended by 2.5 Kb both directions centered on the anchor point, resulting in a "refined anchor". Then, loops were filtered to include those inside the 476 RAIDs. Finally, two loops were considered to "overlap" if both pairs of "refined anchors" overlap (pairToPair function of BEDtools v2.27.0) and Venn diagrams are generated to visualize the results. To calculate the correlation between RAIDs for different data sets, the normalized loop count (FPM) was used as input for Spearman correlation by the cor.test function in R (v3.5.1).

Peak Correlation in RAIDs

To find the peak correlation between two libraries inside 476 RAIDs, the peak regions are extended by x kilobase (Kb) pairs in both directions, and the union of the two sets of extended peak regions is used as a reference set of "union peaks". Within these union peaks, the normalized pileup values are computed (FPM) for each library, and then the correlation between these values is determined. For comparing the RNAPII ChIA-Drop combined data versus ChIA-PET, x=3 Kb was used, and for comparing RNAPII ChIA-Drop replicate 1 versus replicate 2, x=0.5 Kb was used. These analyses were performed using BEDtools (v2.27.0) and the R (v3.5.1) package ggplot2 (v3.1.0).

Comparison of ChIA-Drop and RNAPII ChIA-Drop Data by Domains

The chromatin fragments in ChIA-Drop and RNAPII ChIA-Drop data were hit to TADs and RAIDs, respectively. Total fragment numbers hit in the two types of domains were used to calculate the normalized density for FPKM in boxplots. Similarly, the chromatin fragments were also hit to transcriptionally active and inactive domains, respectively, and FPKM are shown in boxplot.

Complexity of GEM

The ChIA-Drop complexes in TADs and RNAPII ChIA-Drop complexes in RAIDs are analyzed separately using the identical method. Each domain is partitioned into 5 Kb bins, and each complex in the domain is converted into a binary vector as follows: 1 if a midpoint of a fragment is contained in the bin, and 0 otherwise. The complexes covering only one bin are filtered out. Counting the number of 1's (i.e., number of bins covered) for every complex in a domain results in a probability vector named "observed distribution". For a given domain with $n$ bins, the "expected distribution". For a given domain with n bins, the "expected distribution $X_{exp}$~Binomial $$\left(n, \frac{1}{n}\right)$$

and is expressed as the vector $$\begin{bmatrix} \frac{P(X_{exp} = 2)}{1 - P(X_{exp} = 0) - P(X_{exp} = 1)}, \\ \frac{P(X_{exp} = 3)}{1 - P(X_{exp} = 0) - P(X_{exp} = 1)}, \cdots, \\ \frac{P(X_{exp} = n)}{1 - P(X_{exp} = 0) - P(X_{exp} = 1)} \end{bmatrix}.$$

These two sets of probability vectors of lengths n−1 are plotted with heights as the average and error bars as the standard deviation computed over domains. Examples are provided in the Example 3.

Quantification of Heterogeneity in ChIA-Drop and RNAPII ChIA-Drop Data

Using the 5 Kb-binned ChIA-Drop and RNAPII ChIA-Drop data in TADs and RAIDs, respectively, the heterogeneity was quantified to capture the dynamic nature of complexes. In each domain, unique combinations of bins observed (in the binary vectors) were identified and the number of complexes in each combination were counted. These counts were normalized by the total number of complexes in the domain and the resulting probability vector is used to calculate the normalized Shannon entropy (43). All 583 entropies from TADs and 476 entropies from RAIDs are plotted as histograms, with each set normalized by the maximum height. Detailed methods and examples are in Example 3.

Enhancers and Promoters in RNAPII ChIA-Drop Data

The RNAPII ChIA-Drop chromatin complexes are separated into 476 RAIDs. If a complex spans two RAIDs, they are two sub-complexes, and total 5,206,343 sub-complexes are extracted and their fragments are annotated as 'promoter' or 'enhancer'. If a fragment overlaps with a promoter region (TSS±250 bp) of any isoforms of a gene, it will be marked as a promoter fragment ('P'); otherwise, it is a non-promoter fragment ('NP'). With an additional requirement that a sub-complex includes at least 2 fragments in a RAID and at least one promoter, 175,294 sub-complexes are categorized by the number of promoters and the counts are plotted. Of note, 64% belong to 1 enhancer with 1 promoter, 14% was involved in 2 promoters, and 22% belonging to multiple fragments (F≥3).

Active Gene Annotation and Promoter Fragments Assignment in RNAPII ChIA-Drop Data In order to annotate genes of *Drosophila* into 'active' and 'inactive' categories by RNA-Seq expression signal, 'union exon'-based (UE) method is applied 44. First, exons of all isoforms of a gene were merged to 'union exons', which are used to align reads, and the RPKM is defined as the number of reads aligned to UE divide by the UE length. A gene is labeled as 'active' if its RPKM ≥1 and 'inactive' if its RPKM <1. There are 6,614 inactive genes (43%) and 8,726 active genes (57%) in UCSC dm3 ref-gene, which in RAIDs include 3,210 inactive genes (30%) and 7,334 active genes (70%).

Figure 13A:
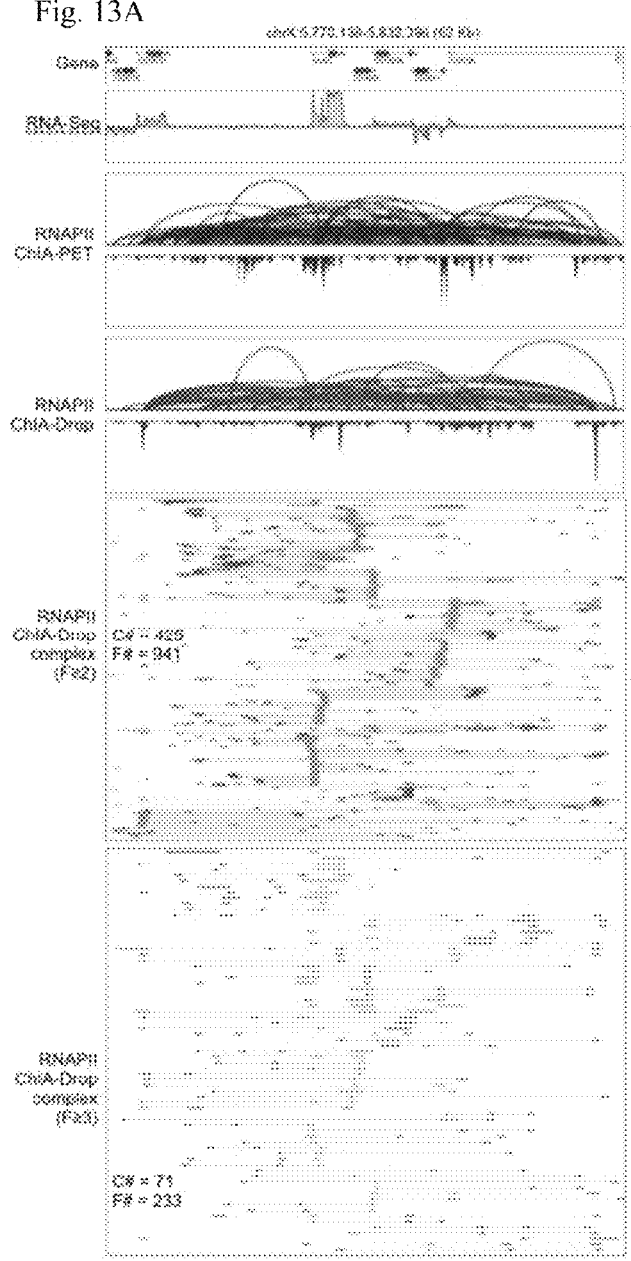
FIG. 13A-E provides data from embodiments of RNAPII ChIA-Drop characterization.
Figure 13B:
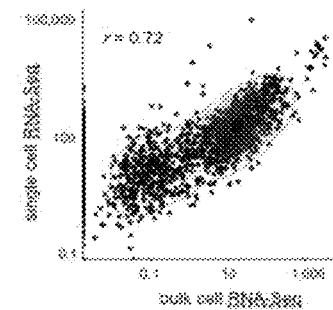
Figure 13C:
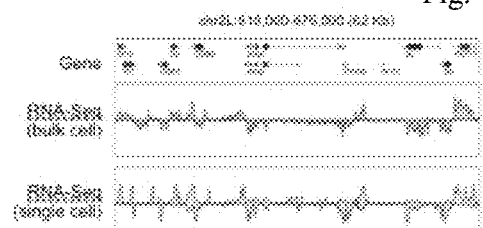
Figure 13D:
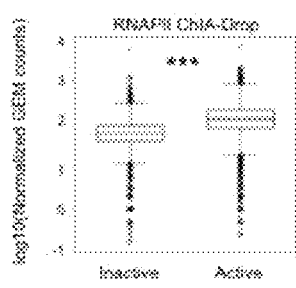
Figure 13E:
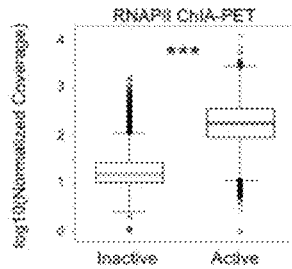
Figure 15A:
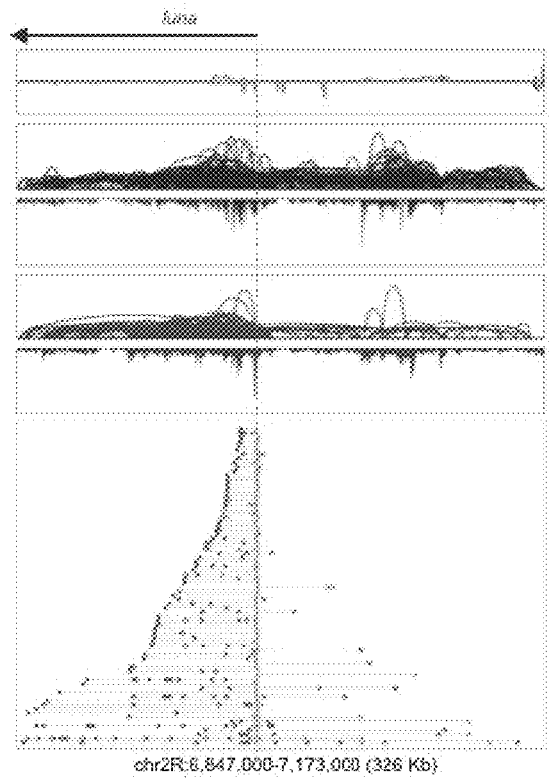
FIG. 15A-D provides data from embodiments of examples of intra-genic RNAPII ChIA-Drop data.
Figure 15C:
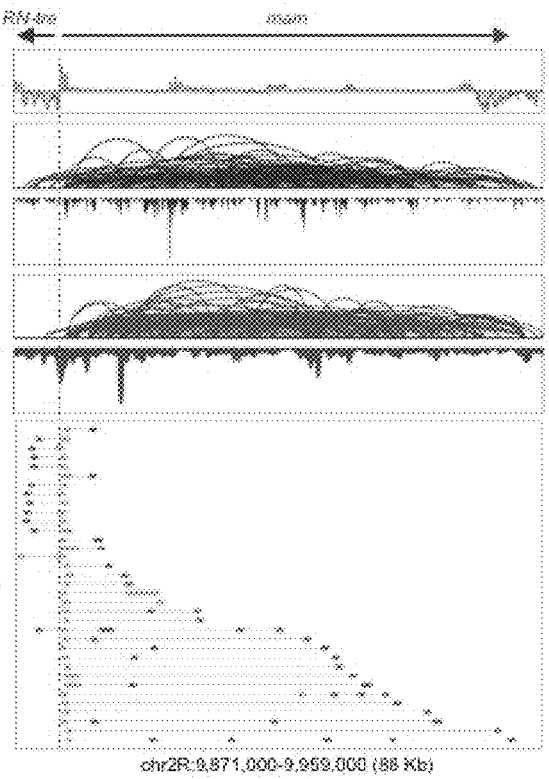
Figure 15B:
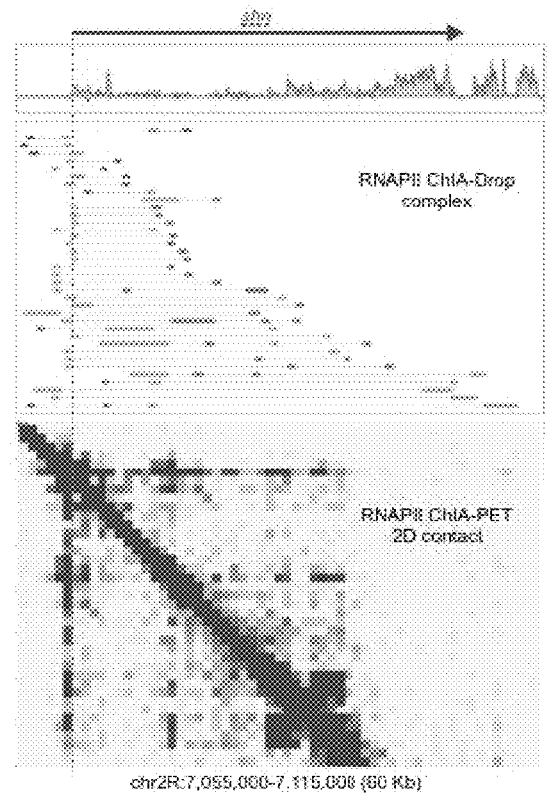
Figure 15D:
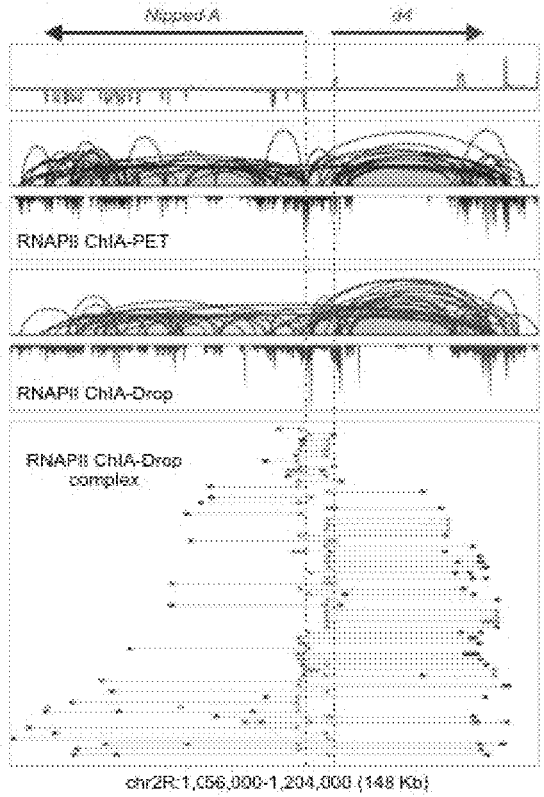

For each of these 10,544 (=3,210+7,334) genes, the number of GEMs covering gene promoters are normalized by the number of unique isoforms (i.e., only the isoforms with unique TSS). Note that due to the high density of the *drosophila* genome, two or more gene promoters may overlap. In the event that RNAPII ChIA-Drop GEM fragment is in such overlapping regions, all overlapping gene promoters are enumerated and a GEM is counted multiple times. Similarly, the RNAPII ChIA-PET mean coverage of each gene promoters in RAIDs are also normalized. Two populations of active and inactive genes are shown in boxplots (FIG. 13D-E).

Single-Cell RNA-Seq Data Processing

The single-cell RNA-Seq (scRNA-seq) raw FASTQ files were mapped to *Drosophila* genome (dm3) by using 10X Genomics cellranger count (v2.1.1, https://support.10xgenomics.com/single-cell-gene-expression/software/pipelines/latest/using/count) with a key parameter (recovered_cells=6000). The scRNA-Seq dataset generated contained data for 10,374 individual cells. First the data was pre-processed with quality-control (QC) filtering as follows. Any cells that expressed <5% of the total genes were excluded, and any genes that were expressed in <5% of cells were excluded. Each gene that passed QC has a separate text file with sparse representation of data: the first column is the cell index and the second column is the expression level, and only cell indices expressing that gene are present in that file. The approach for determining the number of individual cells that co-express a particular combination of genes is as follows. First, the median gene expression level across all genes and all cells was computed. Then, for each gene, its expression in each cell was converted to binary "on" (expression level greater than the median) or "off" (expression level less than the median). The number of cells that co-express a gene combination is the number of cell indices than have an "on" value for each of the genes.

Heterogeneity of RNAPII ChIA-Drop and scRNA-Seq Data by Active Genes in RAIDs

Of 476 RAIDs, 427 contained at least 10 complexes and at least 2 active genes. In each RAID, the unique combinations of active gene promoters captured by RNAPII ChIA-Drop are identified, and the counts for each combination are used for Shannon entropy calculation. Then, the heterogeneity of active genes in scRNA-Seq data was analyzed as follows. Of the 476 RAIDs from above, there were 403 RAIDs that contained at least 2 genes that passed scRNA-Seq QC filtering (expressed in >5% of cells). In each RAID, the unique combinations of co-expressed genes were tallied across individual cells from scRNA-Seq and then the entropy was calculated.

3-Promoter Clustering and t-SNE Visualization

The RNAPII ChIA-Drop chromatin complexes inside RAIDs are further extracted if their fragments connect exactly 3 gene promoters, which are defined as above. For these complexes, the expression level of each of the 3 genes were defined as the RPKM of union exons of all isoforms from the RNA-Seq data (GSM SRR1957059). Next, the chromatin fragments overlapping with gene promoters are renamed by their gene names and are sorted by their expression level in an ascending order. The resulting 3-promoter gene sets are deduplicated and their expression values are normalized for each set. All sets were embedded in two dimensions via t-distributed Stochastic Neighbor Embedding (t-SNE)45 using Rtsne (v0.13) package in R (v3.5.1); its output matrix was clustered by using dbscan (v1.1-3) package (with k=20) and fpc (v2.1-11.1) package (with eps=0.14).

Enrichment of 3-Promoter Gene Sets

For each of the 877 gene sets above, their expression levels of RNA-Seq (GSM SRR1957059) was plotted in pileup reads RPKM. The maximum coverage values within the gene promoter regions were recorded by ChIP-Seq data of RNAPII (GSM1017403), H3K4me1 (GSM1017407), and H3K4me3 (GSM1017409). In addition, the scRNA-Seq data set generated in this study was used to count the number of individual cells expressing each gene, and "H3K4me1/H3K4me3" plot is the ratio of H3K4me1 to H3K4me3. Aggregate values for each dataset were plotted by the categories classified above.

Aggregation Plot

Aggregation plots have been used extensively in epigenomics to visualize the average profile of a signal (e.g., ChIP-seq binding) over a set of genes. Here, the concept of aggregation plots was extended to chromatin interaction loops to visualize the average looping profile over a set of genes. First, the RNAPII ChIA-drop was converted to pairwise contacts, which were then processed by the ChIA-PET pipeline to merge individual pairwise contacts into loops (see Example 2, which describes methods of ChIA-DropBox). Next, the set of genes to be included was defined as genes that are (a) active (based on RNA-Seq data) and (b) located inside RAIDs (identified from RNAPII ChIA-PET data). The genes were then aligned by using twenty 5-percentile bins from the TSS to the TES along each gene, and extending upstream and downstream proportionally. For each gene, the interaction frequency from the TSS bin to all other bins was determined and then normalized by the gene length. These percentile-binned and normalized interaction frequencies were then averaged across all genes.

PacBio Data Processing

PacBio subreads were aligned to the reference genome (dm3) using bwa mem (v0.7.12) 46 with the "-x pacbio" flag. samtools (v1.8)47 was then used to converted the SAM file to BAM format and to filter to retain only uniquely mapped subreads. Then, the pysam module (v0.7.5) in python (v2.7.13) was used to group together subreads that originated from the same polymerase read and to identify the number non-overlapping chromatin fragments in each polymerase read, thus identifying potential chromatin interactions.

3D DNA FISH Images Analysis

Imaris software (Bitplane Inc) was used to analyze the 4-color-probe 3D FISH data. The positions (3D coordinates: x, y, z) of the probes in each cell were identified by applying the Imaris "Spot" function sequentially to the fluorescent channels corresponding to each of the four colors. In each DNA-FISH probe color, 100-400 cells were measured. Probes of different colors belonging to the same nucleus were identified computationally by hierarchical clustering, where the nuclei number in each image was used for expected cluster number. The nuclei with spots for each of the 4 colors were retained for further analysis. Within each nucleus, the pairwise distances between the probes were computed as the 3-dimensional Euclidean distances. For example, between two spots a and b:

$$d(a,b) = \sqrt{(x_a - x_b)^2 + (y_a - y_b)^2 = (z_a - z_b)^2},$$

where two given point 3D coordinates are $a = (x_a, y_a, z_a)$ and $b = (x_b, y_b, z_b)$. Finally, all data that belong to the same DNA-FISH validation locus was combined, and the density of spot-spot 3D distance was plotted using R packages ggplot2.

Data Availability

The ChIA-Drop and RNAPII ChIA-Drop data (raw sequencing files FASTQ, processed data files of read-ID with GEMcode, and files of chromatin interaction complexes), ChIA-PET and in situ ChIA-PET data (raw sequencing files FASTQ and BAM, files of reads pileup coverage, files of interaction clusters), and Single-cell RNA-Seq data (raw sequencing files FASTQ, processed data files of genes.tsv, barcodes.tsv, and matrix.mtx) are available at Gene Expression Omnibus under SuperSeries accession number: GSE109355.

Results and Discussion

The ChIA-Drop Methodology

To develop the ChIA-Drop protocol, Drosophila Schneider 2 (S2) cells were used, which is a well-characterized model for epigenomic and 3D genome-mapping studies (5, 18). The Chromium microfluidics system (10X Genomics) that was adopted for ChIA-Drop was established for high-molecular-weight genomic DNA analysis (17). First, the microfluidics systems was tested for its ability to handle chromatin-DNA barcoding and amplification followed by short-tag sequencing. Crosslinked chromatin DNA was prepared from S2 cells fragmented by restriction digestion, and as a control, the pure DNA templates that were de-crosslinked and purified from the same chromatin DNA sample. The fragmented chromatin DNA sample and the de-crosslinked purified DNA control were then separately loaded onto microfluidic chips for sample compartmentalization, GEM-specific barcoding, and amplification. Next, the DNA amplicons were analyzed by Illumina sequencing with a read length of 150 bp, and the reads from the chromatin DNA sample were compared to the pure DNA control.

It was verified that the majority of the sequencing reads from pure DNA templates were of high quality, i.e., most reads had the maximum read length (130 bp genomic plus 20 bp linker sequences), and 95.99% of the reads were uniquely mapped to Drosophila reference genome (dm3). In comparison, for tethered chromatin DNA sample, 58.65% of the sequencing reads were of high quality and mapped to the reference genome (FIG. 6A). Most of the unmapped short reads (19-20 bp) from the chromatin DNA sample contained only linker sequences, indicating that either these GEMs lacked chromatin material in the droplets, or that the chromatin DNA templates in those GEMs were not accessible for priming. Nonetheless, the large numbers of barcoded sequencing reads generated directly from crosslinked chromatin material suggests that this microfluidics system is suitable for chromatin interaction analysis (FIG. 6B-C). Next experiments were performed that tested whether short chromatin fragments (~300 bp) generated by restriction digestion with a 4-bp cutter (MboI), or long chromatin fragments (~3000 bp) generated by a 6-bp cutter (HindIII), are more suitable for ChIA-Drop experiments. The analysis shows that the longer chromatin fragments as templates yield more mappable data than shorter fragments. Similarly, chromatin sonicated to fragments (~6000 bp) were also suitable for ChIA-Drop analysis (FIG. 6C-E), indicating that longer chromatin fragments may have more opportunity for annealing to barcoded primers at possible open stretches of DNA templates for amplification. Studies were also performed to test various amounts of chromatin input, and it was determined that 0.5 ng was an optimal loading concentration for the system. When chromatin was diluted to 0.5 pg, nearly all sequencing reads were the linker sequence only (FIG. 6F), indicating most of the droplets were empty of chromatin material. Finally, the proportion of GEMs that might contain mixed independent chromatin complexes was estimated by conducting an inter-species experiment using fly and human chromatin samples that were mixed in equal amounts. If a GEM contained a mix of chromatin fragments from fly and human, then the DNA reads derived from that GEM would be mapped to both human and fly genomes (FIG. 6G). This library was sampled with 4.6 million sequencing reads, and only 5% of the GEMs contained reads from both species, indicating most GEMs that possess any chromatin material contain only one complex. Therefore, this microfluidic-based system can produce reliable data directly from crosslinked sample for chromatin interaction analysis.

Figure 7A:
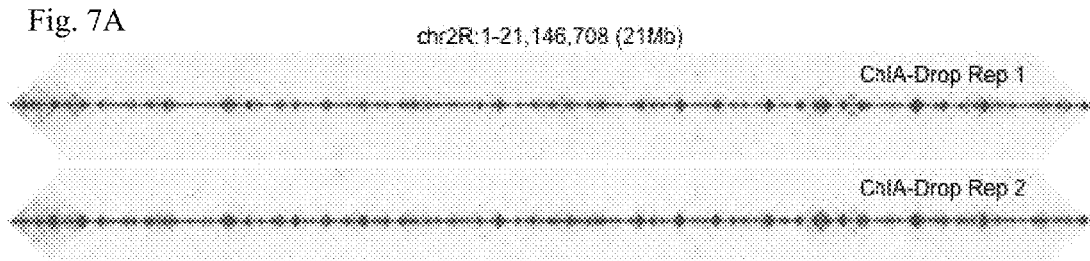
FIG. 7A-G provides data from embodiments of ChIA-Drop data reproducibility and characterization.
Figure 7B:
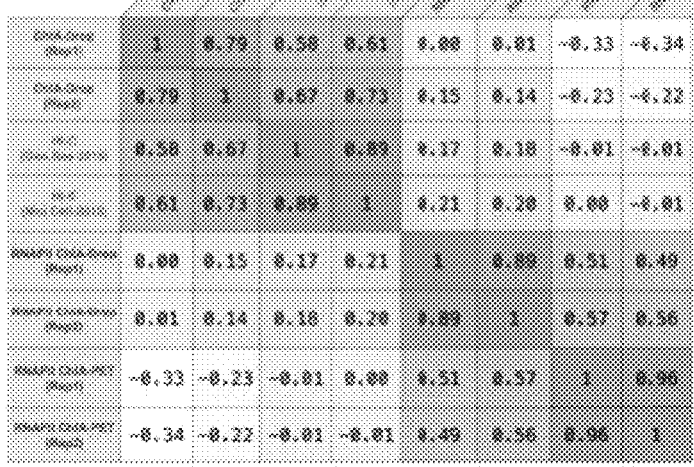
Figure 7C:
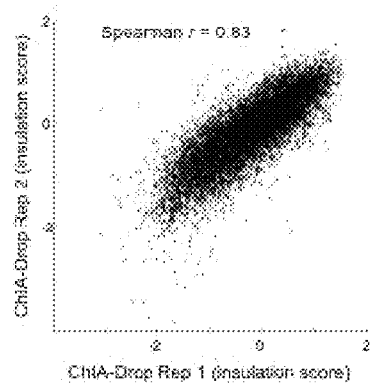
Figure 7D:
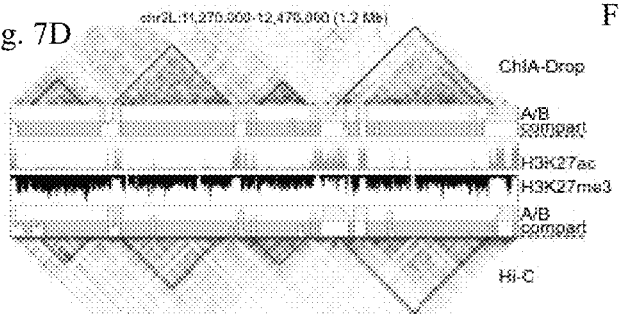
Figure 7E:
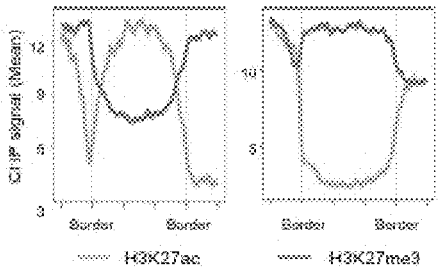
Figure 7F:
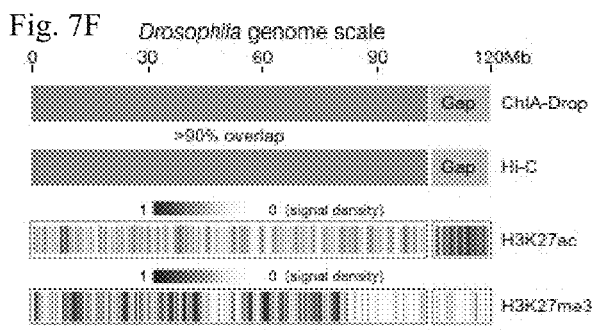
Figure 7G:
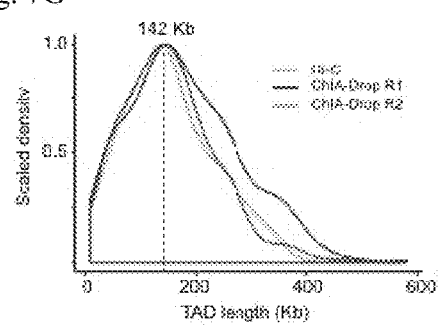

Using the ChIA-Drop protocol (Methods), multiple replicates of ChIA-Drop sequencing datasets were generated from S2 cells. Using the ChIA-Drop data-processing pipeline ChIA-DropBox (see methods) the droplet barcodes and the linked chromatin DNA reads were identified. After mapping the reads to the reference genome, only high-quality reads (MAPQ ≥30; length ≥50 bp) were retained, and extended in the 3' direction by 500 bp to reflect the length of DNA templates subjected to sequencing analysis. DNA reads with the same barcode were merged into one fragment if the aligned reads overlapped, and for further downstream analysis, the fragment genomic coordinates were extended by 3 Kb to represent chromatin fragment length (see Examples 1 and 2). The chromatin DNA fragments tagged with the same GEM barcode were assumed to originate from the same microfluidic droplet, ideally from a single chromatin complex tethering multiple DNA fragments from different genomic loci. However, due to the randomness in the microfluidics system, unrelated chromatin complexes could be partitioned into the same droplet, resulting in technical artifacts. To address this problem, a data processing scheme was devised to refine the GEMs based on the number of fragments and chromosome origins. From the statistics, it was recognized that a major source of noise was the singleton chromatin fragments, which are readily identified and removed. Also, chromatin complexes of different chromosomal origins could be mixed into the same GEM. Therefore, data processing refines the GEMs by separating them into purely intra-chromosomal sub-GEMs, which are considered putative chromatin complexes. This is consistent with previous findings that most known chromatin-folding features are found within (intra-) chromosomal territories (20). Finally, a "domain-based distance test" algorithm was developed based on polymer physics (19) and information theory to further identify and filter out possible intra-chromosomal noise, and obtain a refined set of complexes (see Example 2). Additionally, the reproducibility assessment using replicates demonstrated that a large portion of the ChIA-Drop data were reproducible (FIG. 7A-C). In total, around 3 million chromatin complexes with two or more fragments (F≥2) were identified. The ChIA-DropBox pipeline also includes visualization tools to view the ChIA-Drop data in 2D contact maps and linear browser profiles.

With the exception of its unique ability to resolve the multiplex nature of chromatin complexes, ChIA-Drop should essentially detect the same spectrum of chromatin contacts as Hi-C does. Thus the ChIA-Drop data was compared with the Hi-C data of the same cells (21, 22) to validate the new method. The chromatin complexes with multiple DNA fragments in ChIA-Drop data should reflect multiple, simultaneous chromatin contacts. However, because Hi-C relies on proximity ligation between two DNA fragments, each fragment in a Hi-C experiment can only be associated with one other fragment. Thus, the ligation-based pairwise contacts in a Hi-C experiment are an aggregate of random sampling of all possible proximity ligation products among millions of chromosome copies. To directly compare ChIA-Drop with Hi-C data, a random-sampling algorithm with multiple iterations was devised to best mimic the pairwise Hi-C-like output from the ChIA-Drop data and visualized the adjusted ChIA-Drop data in 2D contact maps (see Example 2). As shown, ChIA-Drop captured chromatin structural features that largely resemble those of Hi-C (FIG. 1B-C, FIG. 7). Hi-C computational program (23) was applied to ChIA-Drop data for TAD calling and it was verified that most of the distinctive chromatin structures were comparable between ChIA-Drop and Hi-C data (FIG. 1B-C, FIG. 7D-G).

Multiplex Chromatin Interactions

Figure 8A:
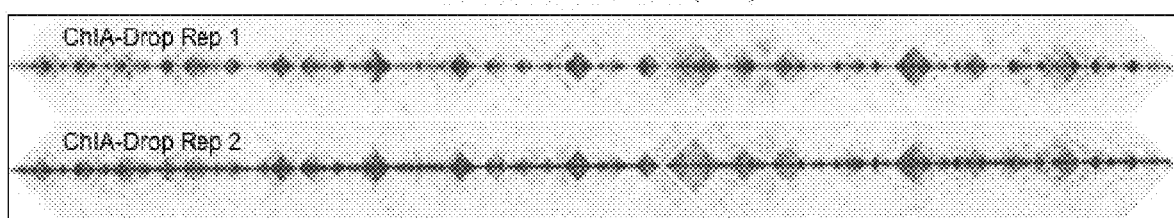
FIG. 8A-C provides data from embodiments of decomposition analysis of ChIA-Drop data.
Figure 8B:
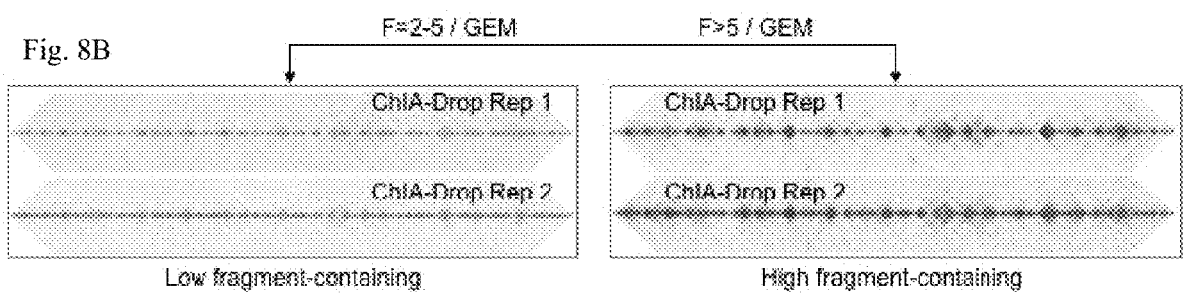
Figure 8C:
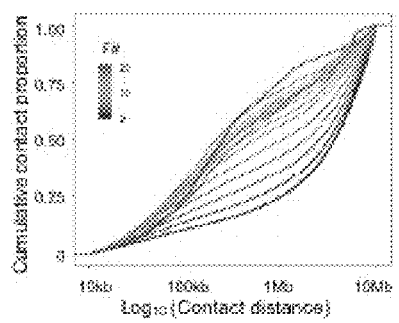
Figure 10A:
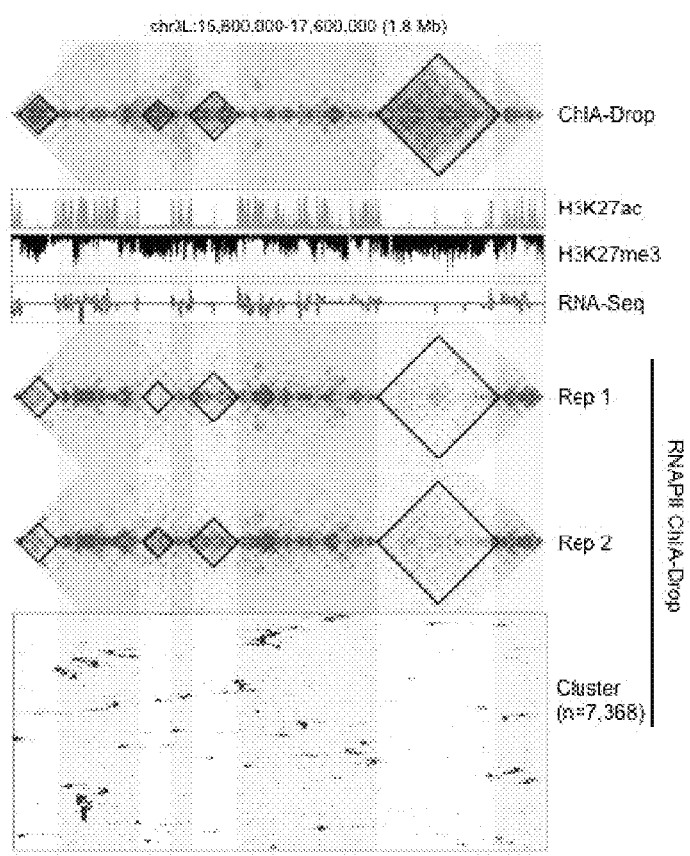
FIG. 10A-E provides data from embodiments of characterization of RNAPII ChIA-Drop data.
Figure 10B:
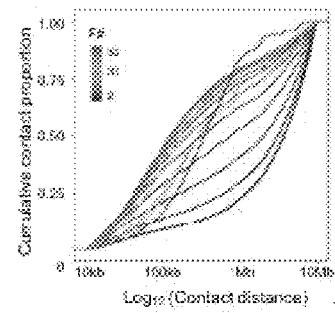
Figure 10C:
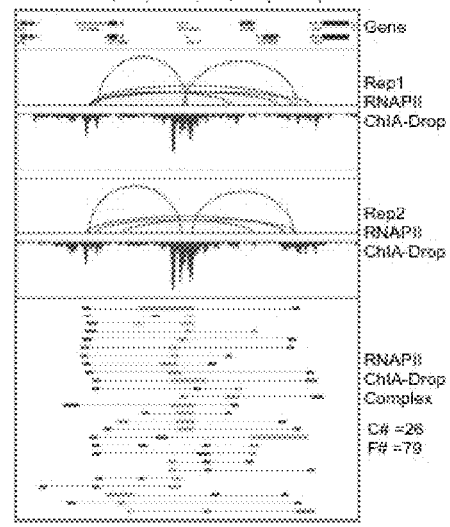
Figure 10D:
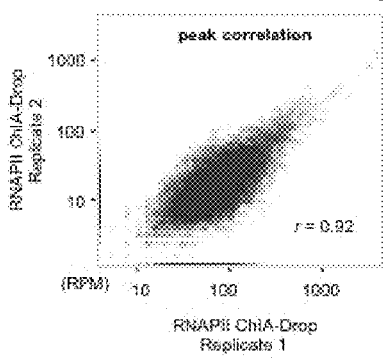
Figure 10E:
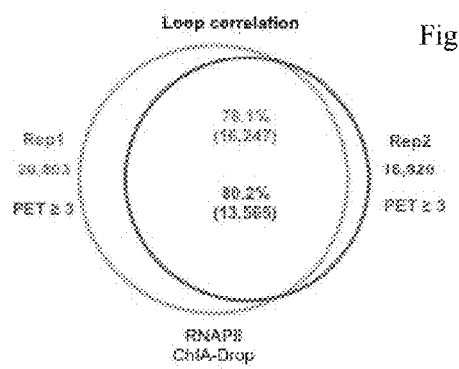

Unlike the Hi-C data, ChIA-Drop allows characterization of the contribution of chromatin complexes to TADs by the number of interacting chromatin fragments in the complex. Indeed, about half (n=1,493,818) of chromatin complexes in the ChIA-Drop data contained three or more fragments (F≥3), thus generating a large repertoire of putative multiplex chromatin interactions involving multiplex chromatin contacting loci simultaneously. Surprisingly, some of the ChIA-Drop complexes (n=19,778) had tens—and up to hundreds—of fragments, indicating significant multiplexity of some chromatin interactions. Accordingly, the ChIA-Drop data was decomposed arbitrarily based on fragment (complexes with 2 fragments, F=2; with 3 fragments, F=3; and so forth), and the data plotted of each class for 2D contact analysis. Intriguingly, most of the contacts from low-fragment-containing complexes (F=2-5) were randomly scattered away from the 2D contact axis, whereas complexes with a higher number of fragments tended to cluster and provided distinctive chromatin topological structures (FIG. 2A, FIG. 8A-B). Statistical analysis via the empirical cumulative distribution function (ECDF) of pairwise distances showed that the contacts of the low-fragment-containing complexes were mostly at extremely long distance and deviated more from the reference ECDF curve of Hi-C data (FIG. 2B, FIG. 8C), further suggesting that the high-fragment-containing complex data were of sufficiently high quality for multiplex chromatin interaction analysis.

Figure 2C:
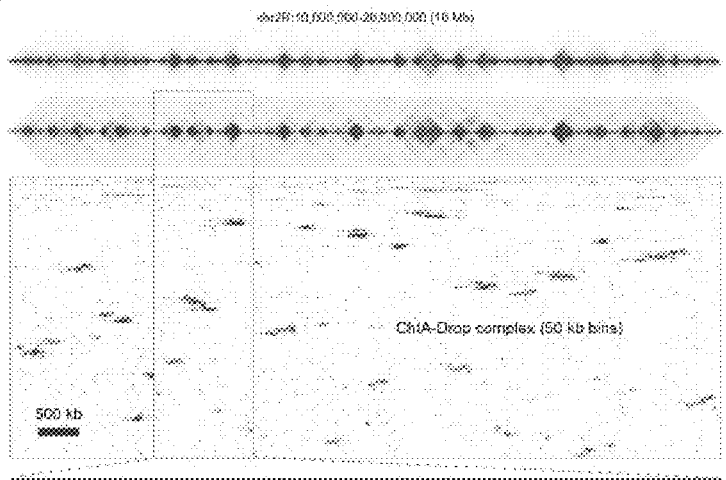
Figure 2B:
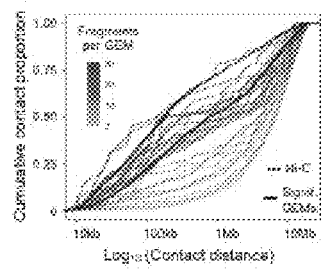
Figure 2D:
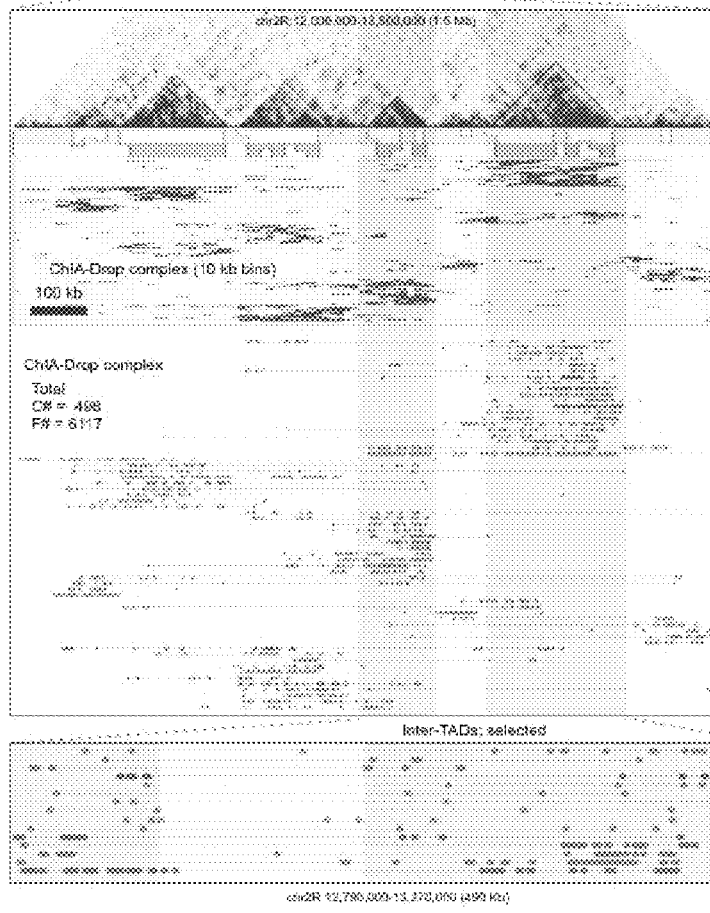
Figure 2E:
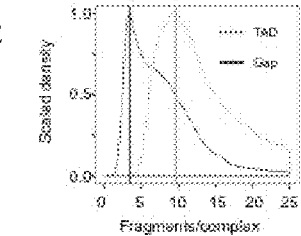
Figure 2F:
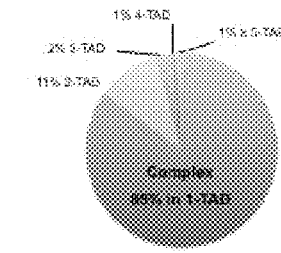

Studies were then focused on ChIA-Drop complexes (n=170,752) with a high number of interacting fragments (F≥6) for further analysis. By binning contact data at various resolutions (50 Kb, 10 Kb and 5 Kb) and performing hierarchical clustering to order the complexes by similarity, it was possible to directly view multi-fragment chromatin complex data in linear alignment across the genome (see Example 2). For example, in a 10 Mb segment of chromosome 2R (chr2R), there were 2,088 chromatin complexes identified by ChIA-Drop. At a 50 Kb bin size resolution, many chromatin complexes were clustered with distinctive patters (FIG. 2C). Zoom-in at a 1.5 Mb region with 10 Kb bin resolution showed more detailed patterns of complex clusters and individual fragments within chromatin complexes (FIG. 2D). These complex clusters were highly associated with chromatin topological structures of TADs and gap regions, uncovering a high level of multiplexity and heterogeneity of chromatin contacts at the single molecule level. The ChIA-Drop complexes associated with TADs usually contained more fragments per complex than complexes associated with gap regions (FIG. 2E). Overall, most of the ChIA-Drop complexes associated with TADs fall within a single TAD (82,506; 85%), while many complexes (14,630; 15%) cover two or more TADs (FIG. 2F). In particular, the inter-TAD complexes suggested potential higher-order multiplexity in chromatin contacts, and a "frequency-based binomial test" was performed to assess their significance. Of 9,723 inter-TAD contacts established by 14,630 complexes, 1,168 contacts including 4,757 complexes were statistically significant (see Example 2). Together, the ChIA-Drop data demonstrated extensive multiplexity of chromatin interactions inside TADs as well as between TADs with single molecule resolution. Furthermore, each chromatin complex identified by ChIA-Drop represents the multiplex chromatin interactions derived from a single copy of chromosome or a single cell. Therefore, the overlapping ChIA-Drop chromatin complexes at a given genomic region would reflect cell-to-cell commonality as well as heterogeneity.

To validate the single molecule and single cell property of multiplex complexes captured in ChIA-Drop data, studies were performed that applied PacBio long-read DNA sequencing to directly analyze the proximity ligation products prepared from the chromatin sample of S2 cells. Although most of the PacBio long-read sequences included only one chromatin fragment, thousands of long-reads were identified that include multiple chromatin fragments and show high heterogeneity within TADs, similar to the intra-TAD ChIA-Drop data (FIG. 9A-B). 3D FISH was also applied to validate the inter-TAD multiplexity of the ChIA-Drop complex data. Within a 1.1 Mb segment in chr2L encompassing 4 TADs (labeled "T1", "T2", "T3", and "T4") (FIG. 3A), the ChIA-Drop inter-TAD data showed inter-TAD contacts among T1, T3 and T4, whereas T2 showed minimal contacts with the other TADs. Accordingly, fluorescent DNA probes were designed for each of the 4 TAD regions (FIG. 3B), of which probe T2* was expected to work as a de facto internal control point for no contacts, and two T4 probes (T4a and T4b) served as intra-TAD references. Two separate sets of 4-color FISH experiments were performed with the test combination probes (T1, T3, T4a, T4b), and with a control combination including the control probe (T1, T2*, T3, T4b), respectively. For each combination, 100-400 nuclei were examined, and the spatial distance (μm) between the centers of signal foci (FIG. 3C) was determined. As expected, the distance between T4a and T4b was very small (0.22 μm), indicating that the two probes within the T4

TAD were in close contact. Notably, the T3 probe was much further away spatially from T4a (0.50 µm), even though the linear genomic distance between the pairs T3-T4a and T4a-T4b are roughly the same. The spatial distances between T3-T4a and T3-T4b were almost exactly the same, further indicating that T4a and T4b were in the same spatial domain and away from T3. Furthermore, using T4b as a reference point and comparing the spatial position of T1 and T2*, it is noteworthy that the nuclear distance of T1-T4b was substantially shorter than the distance of T2*-T4b, even though the linear genomic distance between T1 and T4b is much larger than that between T2* and T4b. These patterns are consistent with the ChIA-Drop data (FIG. 3A). In addition, after applying a given distance cutoff (0.28 µm) that was enough for separation of intra-TAD and inter-TAD spatial distance, the percentage of colocalization was calculated for two and three probes in the FISH data, and this was compared with the ChIA-Drop complexes mapped over multiple TADs (FIG. 3D). Additional FISH validation results (FIG. 9C-J) at a Hox gene cluster (24), and the use of available 3-color super-resolution DNA FISH data published previously (25), all supported the multiplexity of chromatin interactions in ChIA-Drop mapping data.

Interestingly, as annotated by epigenomic and transcriptomic data, most TADs in S2 cells as identified by ChIA-Drop and Hi-C were closely associated with repressed chromatin domains, whereas transcriptionally active domains largely reside in the boundary gap regions between TADs (FIG. 3E, FIG. 7D-F). This chromatin feature also matched with the AB compartments called by ChIA-Drop data, where the A compartment is for active and the B compartment is for repressive features. The observation is also consistent with the properties of genome architecture in another Drosophila cell line Kc167 recently reported using Hi-C, HiChIP and ChIA-PET data (26). In addition, DNA-binding protein factors are known to be important in defining chromatin architecture (18, 27), and many of them were found highly associated with the chromatin complexes in ChIA-Drop data. For instance, within a 160 Kb TAD domain on chr2R, 29 chromatin complexes containing 328 fragments were identified. Here, the protein factor BEAF-32 (boundary element-associated factor of 32kD) (28) possibly defines the TAD boundaries, whereas Su(Hw) (suppressor of hairy wing) (29) potentially enforces chromatin contacts inside TADs (FIG. 3E-F).

Together, ChIA-Drop data are validated by single molecule long-read sequencing for multiplex chromatin interactions and by 4-color 3D FISH for imaging chromatin conformation in single cells. It is now possible to map and visualize single-copy chromatin folding structures of complex genomic loci in all combinations represented individually in many cells, instead of the aggregated topological approximation based on pairwise contacts from bulk cells with no distinction of individual ones (FIG. 3G).

RNAPII-Associated Multiplex Chromatin Interactions

To investigate chromatin interactions involved in transcriptional regulation with single molecule resolution, a RNAPII chromatin immunoprecipitation (ChIP) step was added to the ChIA-Drop protocol (FIG. 1A; Example 1). These experiments were performed in S2 cells and generated eight libraries in two biological replicates of RNAPII ChIA-Drop sequencing data, and confirmed its reproducibility (FIG. 7B, FIG. 10). Using the same ChIA-DropBox data-processing pipeline (see Example 2), around 2 million chromatin complexes with two or more chromatin fragments were identified. In general, RNAPII ChIA-Drop data showed similar 2D contact patterns (FIG. 4a) as the ChIA-Drop data (without RNAPII enrichment). Strikingly, however, the RNAPII ChIA-Drop data exhibited considerable reductions of chromatin contact signals in repressed domains (TADs), but substantial signal enrichment in active regions (TAD boundary gaps) as demarcated by histone markers and transcription profiles (FIG. 4A-B), reflecting the ChIP enrichment effect. This effect is more pronounced for statistically significant complexes identified by the 'frequency-based enrichment test', which retains complexes with enriched chromatin fragments (see Example 2). Together, the observation validated that the ChIA-Drop experimental system successfully reflects the properties of input chromatin samples (enriched or not), and that ChIA-Drop can be applied to investigate multiplex interactions among regulatory elements associated with transcriptional activity and mediated by a given protein factor.

To specifically compare the RNAPII ChIA-Drop to ChIA-PET in Drosophila S2 cells, studies were performed that mapped chromatin interaction loops mediated by RNAPII (FIG. 11) using ChIA-PET30 (See methods). Many RNAPII loops are interconnected in daisy-chain structures in transcriptionally active regions, and are defined as RNAPII-associated interaction domains (RAIDs) (FIG. 4B-D). From the RNAPII ChIA-PET, results identified 476 RAIDs in S2 cells, most of which are composed of multiple interacting loci of transcriptional elements such as promoters and enhancers and overlap with the active domains (FIG. 4B). In addition, there are detectable long-range chromatin contacts between RAIDs (FIG. 4C-D, FIG. 11E), hinting at further complexity of higher order chromatin organization involved in transcriptional regulation, similar to previous observations in Kc167 cells (26). However, it is not clear whether the multiplexity of chromatin interactions identified by ChIA-PET occurs in the same copy of a chromosome, or whether it represents a composite view of pairwise chromatin contacts derived from bulk cells. The RNAPII ChIA-Drop and ChIA-PET data were highly comparable based on the pairwise contact loop views (FIG. 7B, FIG. 12). Specifically, most of the RNAPII ChIA-Drop complexes were enriched in RAIDs (FIG. 4B-D). In addition, RNAPII ChIA Drop data also showed inter-RAID contacts across the intervening TAD (FIG. 4D-E), recapitulating the patterns observed in the RNAPII ChIA-PET data, and suggesting higher order chromatin organizations that involve active domain-to-domain interactions.

Because ChIA-Drop provides single-molecule resolution, the multiplex chromatin interactions identified by RNAPII ChIA-Drop should represent the true multiplexity of chromatin folding on the same copy of a chromosome of a nucleus in a cell. To validate this multiplexity of transcriptional chromatin interactions, studies were performed that applied 3D FISH with Leica STED 3X/DLS confocal microscopy. In a chromatin segment of ~1 Mb in size (chr2L: 65,000-1,065,000), RNAPII ChIA-Drop and ChIA-PET identified several RAIDs located in between ChIA-Drop-defined TADs (FIG. 4E). In addition to extensive chromatin contacts inside each RAID, many long-distance contacts between different RAIDs were also observed, and 16 multiplex chromatin complexes involving at least 3 RAIDs were identified (FIG. 4E). To validate these observations by FISH, 4 fluorescent DNA probes were designed, two (labeled "R1" and "R2") for the left RAID in this chromatin segment (FIG. 4E), one (labeled "R3") for the middle RAID, and one (labeled "R4") for the right RAID. In genomic distance, using R1 as the starting and R3 as the middle reference point, R1-R2 is the shortest and R1-R4 is the longest. Since it is known that chromatin architectures mediated by RNAPII in *Drosophila* cells are sensitive to heat shock (31), the 4-color FISH experiments (FIG. 4F) were preformed using HS-treated cells as a control and compared this to untreated cells. As expected, it was observed that in many normal temperature cells the 4-color probes were colocalized in the nuclear space, whereas in many HS-treated cells the probes were spread apart (FIG. 4F). More specifically, the FISH-measured spatial nuclear distances of R1-R2 and R1-R4 in HS-treated cells were notably larger than in untreated cells (FIG. 4G). This is further supported by the detection of R1-R2 probe and R1-R4 probe colocalization in a greater proportion of individual normal temperature cells than HS cells (FIG. 4H). Thus, the RNAPII ChIA-Drop data, including the 16 chromatin complexes spanning 3 RAIDs, are highly likely to reflect multiplex chromatin interactions in single molecules in single cells.

Next, studies were performed that analyzed the multiplexity of chromatin complexes in RNAPII ChIA-Drop data in RAIDs and chromatin complexes in ChIA-Drop data in TADs by comparing to a reference binomial model of expected interaction complexity (see Example 1). Interestingly, the chromatin interactions detected in RAIDs had lower complexity than the expected reference, whereas those in TADs exceeded the expected probability (FIG. 4I), highlighting the inherent difference in these two datasets. In addition, the heterogeneity of multiplex chromatin interactions was evaluated, which may reflect cell-to-cell variation since each ChIA-Drop complex represents a single molecule unit of multiplex interactions originated from a single cell. From the fragment views of chromatin complex mapping, extensive complex-to-complex variations were observed in both RAIDs in the region (FIG. 4D) and TADs (FIG. 2D, FIG. 3F). To quantify the overall heterogeneity, the occurrences of each unique pattern in a domain were counted, and the normalized Shannon entropy of the proportions were computed, (see Example 3). Repeating the process for all domains revealed that the chromatin interactions within RAIDs and TADs are both extensively heterogeneous, with higher degree in TADs than in RAIDs (FIG. 4J). Studies were performed to further investigate the potential complexity of interactions among active gene promoters in RAIDs (See methods; FIG. 13). Interestingly, the promoter-centric complex interactions are more homogeneous (FIG. 4J, bottom) than non-specific interactions in RAIDs (FIG. 4J top), possibly implying deterministic behavior of promoter-driven interactions. Moreover, approximately similar level of heterogeneity is observed in single cell gene expression, suggesting an underlying coordination between promoter interactions and gene expression. Together, the analysis demonstrated that RNAPII ChIA-Drop data were of high quality, exhibited expected chromatin properties as identified from ChIA-PET data, and more importantly, provided single molecule specificity of multiplexity in RNAPII-mediated transcriptional chromatin interactions.

Topological Mechanism of Gene Transcription

Figure 5A:
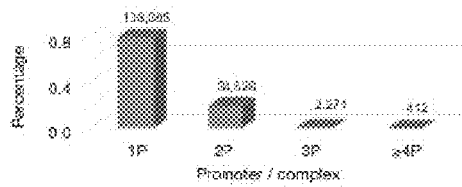
FIG. 5A-F provides data from embodiments of promoter-centered multiplex chromatin interactions reveal a topological mechanism for gene transcription.
Figure 5B:
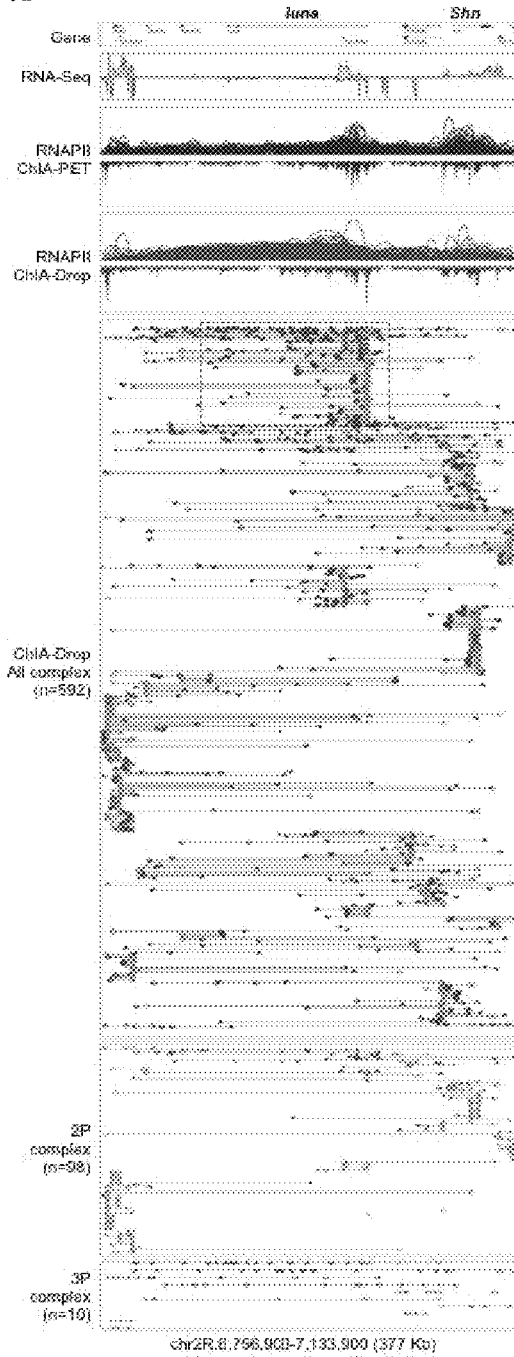

The RNAPII ChIA-Drop data for multiplex chromatin interactions with single molecule precision represents an unprecedented opportunity to investigate mechanistic insights of gene transcription. Focusing on RNAPII ChIA-Drop data in RAID regions, studies were performed that investigated the detailed nature of multiplex chromatin interactions involved in transcription. Specifically, many chromatin interaction complexes (n=175,294, F≥2) were detected that simultaneously connected multiple transcriptional elements such as gene promoters and potential enhancers. Surprisingly, among all the chromatin complexes including promoters, the majority include only one gene promoter, and only 20% include multiple promoters (FIG. 5A-B). This is in sharp contrast with ChIA-PET data, where most gene promoters in a RAID were shown as interconnected in daisy-chain loops of putative multi-gene clusters (FIG. 4D; FIG. 13A). It was reasoned that the discordance is due to the pairwise and aggregated nature of ChIA-PET data, whereas ChIA-Drop reveals single molecule specificity of each chromatin complex. Among the chromatin complexes from ChIA-Drop with multiple promoters, more than 2,700 that simultaneously connected at least three promoters were captured (see methods, FIG. 5A), supporting the notion that multiplex promoter interactions indeed take place in individual cells, but not as extensive as previously suggested (9).

For instance, in an active domain in chr2R with several genes including luna and Shn that 336 were all interconnected as shown by ChIA-PET (FIG. 5B), RNAPII ChIA-Drop detected total 592 ChIA-Drop complexes: 484 of them included one promoter (1P), 98 with two promoters (2P) and 10 with three promoter (3P). In another example, at the locus of Act5C (encoding actin-5C protein for cytoskeletal structure) (32) with other genes (FIG. 13A), 71 chromatin complexes with multiple fragments (F≥3) were identified, all simultaneously connected to multiple transcriptional elements including promoters and enhancers. Notably, Act5C is the most actively expressed gene in the block, and the Act5C promoter was the mostly covered by individual complexes, with some also displaying direct connectivity with other gene promoters.

Figure 5C:
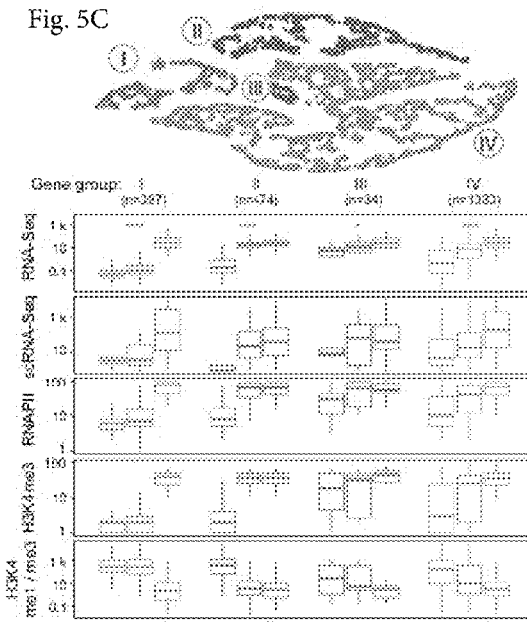

It was previously suggested that the topological basis of multiplex promoter interactions could provide a means for co-transcriptional regulation (9). However, pairwise-based ChIA-PET data could not alone determine whether multiple gene promoters and enhancers on the same chromosome were indeed in simultaneous contact at the single molecule level in individual cells, or whether what was captured were independent, transient pairwise contacts averaged across millions of chromosomes in a proximity ligation experiment. The chromatin complexes from ChIA-Drop with multiple gene promoters thus provide a new opportunity to explore transcriptional multiplexity with single-molecule resolution. To simplify the analysis, only the chromatin complexes that contained 3 promoters were selected, and then the expression data (RNA-Seq) of the associated 3 genes in each of the complexes was used as input for clustering analysis (Example 1 and Example 3). The clustering analysis identified four groups of gene expression patterns (FIG. 5C). Further visualization of RNAPII occupancy and H3K4me3 intensity revealed group-specific characteristics. Group I and group II are highly imbalanced (group I: one dominant gene; group II: two dominant genes), while group III is balanced (three equally expressed genes). Genes clustered in group IV were similar to those in group III but with more variance. This result suggests that chromatin interactions involving multiple genes utilize at least two different mechanisms for transcription regulation: the co-transcription (group III and group IV), where the promoters for different genes are equally active, and the imbalanced-transcription (group I and II), where the weak promoters behave more like enhancers to support the expression of the master genes as previously suggested (9). Indeed, the weak promoters in this relationship exhibited more enhancer-like property as measured by the ratio of H3K4me/me3 ChIP-Seq signals (FIG. 5C; FIG. 14).

Figure 5D:
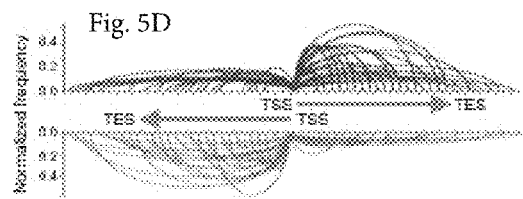
Figure 5E:
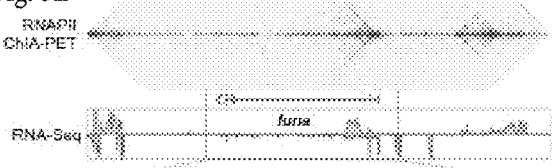
Figure 5F:
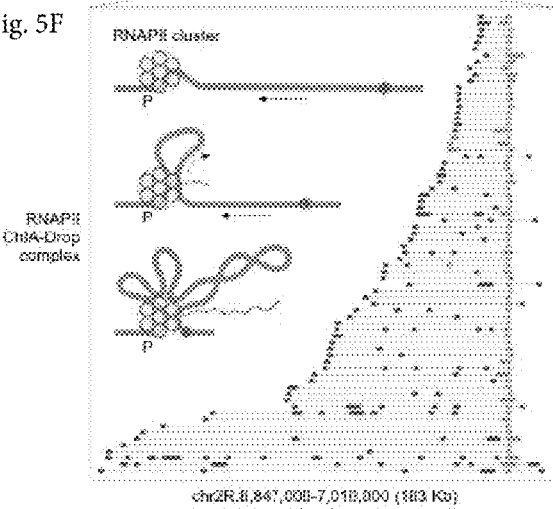

In addition, abundant intragenic contacts were observed in both RNAPII ChIA-PET and ChIA-Drop data with an intriguing orientation-specificity in the direction of gene transcription (FIG. 5B), particularly for large genes over 100 Kb length such as luna (33). Taking all promoter-linked ChIA-Drop complex data (Example 1 and Example 3) in active genes starting from transcription start site (TSS) and plotting them along a normalized gene body model demonstrated that promoter-linked chromatin contacts are preferentially directional toward the transcriptional end site (17), whereas the relative signals of chromatin contacts in the upstream direction were at basal level, indicating that this is a general chromatin feature to most active genes (FIG. 5D). Strikingly, at the luna gene locus (FIG. 5E) the pairwise-contacts of RNAPII ChIA-PET data displayed remarkable chromatin contact "stripe" starting from luna promoter, suggesting a likely promoter-oriented processivity of chromatin looping in concordance with transcription based on aggregation plot. More specifically, RNAPII ChIA-Drop identified 87 luna promoter-linked single-molecule chromatin complexes, and the majority (72, 83%) extended downstream from luna TSS towards TES (FIG. 5F; FIG. 15). Thus, these 72 RNAPII ChIA-Drop complexes with single molecule specificity present a glimpse into the topological details of chromatin folding during transcription for 72 copies of chr2R at the luna locus in possibly 72 individual cells.

Potentially, promoter-linked chromatin contacts in the direction of transcription may suggest a one-sided extrusion model for gene template during transcription, which is different from a conventional tracking model (34). In this extrusion model, it was envisioned that the RNAPII protein cluster with co-factors is assembled at the gene promoter site, or that gene promoters are attracted to RNAPII clusters. When transcription starts, the promoter site is in steady position, while the DNA template is reeled through the transcriptional apparatus for RNA synthesis. Interestingly, in small chromatin complexes with fewer fragments (F=2, F=3, etc.), the chromatin contacts were in close distance to the luna promoter, reflecting the starting phase of DNA extrusion and the formation of small loops. In the larger complexes, there were more chromatin contacts far away from the promoter and closer to TES of the gene, indicating more complicated chromatin looping structures (inset of FIG. 5F).

Discussion

In summary, it has now been demonstrated that ChIA-Drop is an effective method for investigating multiplex chromatin interactions at the single-molecule level, an advance over the previous pairwise, composite methods like Hi-C and ChIA-PET. Through the analyses described herein, in Drosophila cells, it has now been shown that TADs are composed of simultaneous multiplex chromatin interactions on the same chromatin string, and that the chromatin complexes within the same topological domains are highly heterogeneous, suggesting a high level of variation in chromatin contacts at the single molecule level in single cells, consistent with a recent study that also revealed dynamic nature of TAD heterogeneity using a super-resolution imaging approach (35). More importantly, evidence has now been provided that complex chromatin interactions simultaneously involve multiple regulatory elements including gene promoters and enhancers on single chromosomes, using RNAPII-enriched ChIA-Drop data. Contrary to previous chromatin mapping data—based on pairwise ligation and bulk cell analysis—that suggested extensive multiplexity of promoter-promoter interactions (9), ChIA-Drop data revealed that 80% of transcriptionally-active chromatin complexes involved only one promoter interacting with various numbers of non-promoter distal elements. This finding is in agreement with recent studies using super-resolution microscopy for single molecule RNAPII in fixed and live cells, where the authors found that 70-80% of the RNAPII foci contained only one RNAPII molecule (36-38). The 20% of chromatin complexes that involved multiple gene promoters supported the idea of transcriptional factories (39), where multiplex gene promoters were clustered into a transcriptional hub, but not to the extent previously suggested (9). For multi-promoter interaction complexes, the analysis provided two possible mechanisms: co-transcription where genes in the same complex share the transcription machinery and are expressed equally; and imbalanced-transcription, where weak promoters function as enhancers for the dominant genes. Moreover, experiments detected processive multiplex chromatin contacts connected to active gene promoters in the direction of transcriptional orientation in RNAPII ChIA-Drop data, and accordingly support a promoter-centered extrusion model driven by RNAPII apparatus to explain the dynamic property of chromatin looping structures involved in gene transcription.

Finally, the ChIA-Drop protocol is exceptionally simple and robust. Fragmented chromatin samples prepared as for Hi-C or ChIA-PET, but without the need for proximity ligation and without DNA purification, can proceed directly to an automated microfluidics device for gel bead emulsion and droplet-specific chromatin DNA barcoding and amplification, followed by standard sequencing, a non-limiting example of which is Illumina sequencing. The current protocol requires only $5 \times 10^3$ cells for a ChIA-Drop experiment or approximately $6 \times 10^4$ cells for a ChIP-enriched ChIA-Drop experiment under optimized conditions. It is expected that ChIA-Drop will be used for a wide range of biomedical questions and applications.

Example 2

Figure 16A:
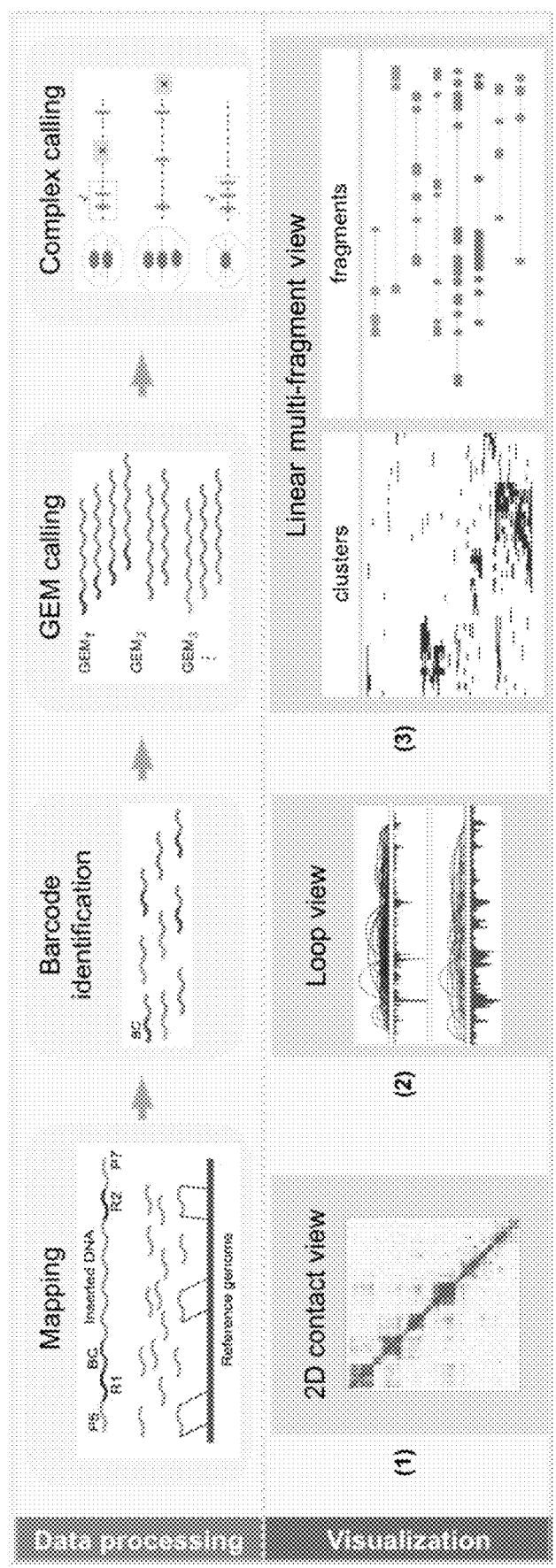
FIG. 16A-C provides flowcharts of an embodiment of the ChIP-DropBox process.

ChIA-DropBox is a pipeline for mapping, analyzing, and visualizing ChIA-Drop data. It includes the following main steps: (1) read mapping, (2) barcode identification, (3) calling of GEMs based on the barcodes, (4) identification of significant chromatin complexes, and (5) data visualization. These steps are illustrated in FIG. 16A.

After the sequencing of ChIA-Drop data with an Illumina Miseq, NextSeq or HiSeq instrument, the ChIA-DropBox workflow was performed as follows. First, the Chromium software suite (10X Genomics) is applied to align reads to the reference genome and to identify the GEM barcode (GEMcode) of each read. ChIA-DropBox then groups uniquely mapped reads with the same GEMcode into "GEMs". Next, GEMs containing reads from different chromosomes are refined by splitting them into purely intra-chromosomal GEMs. For each GEM, reads with overlapping genomic coordinates (following an extension) are merged into "chromatin fragments". Thus, the "fragment number" that is reported for each GEM is the number of non-overlapping genomic segments. Further, a resampling-based significance assessment of genomic distance intervals is applied to refine the set of GEMs into significant "chromatin complexes".

Finally, the resulting chromatin complexes can be visualized at high-resolution using several approaches. First, the data can be converted to pairwise format and visualized using existing tools: 2D heatmap visualization using Juicebox (//github.com/theaidenlab/juicebox/wiki) and loop visualization using genome browsers. In addition, ChIA-DropBox includes its own custom visualization tool for viewing multiplex chromatin complexes, called the "Linear Multi-Fragment Viewer". The steps of ChIA-DropBox are described in more detail below.

Figure 16B:
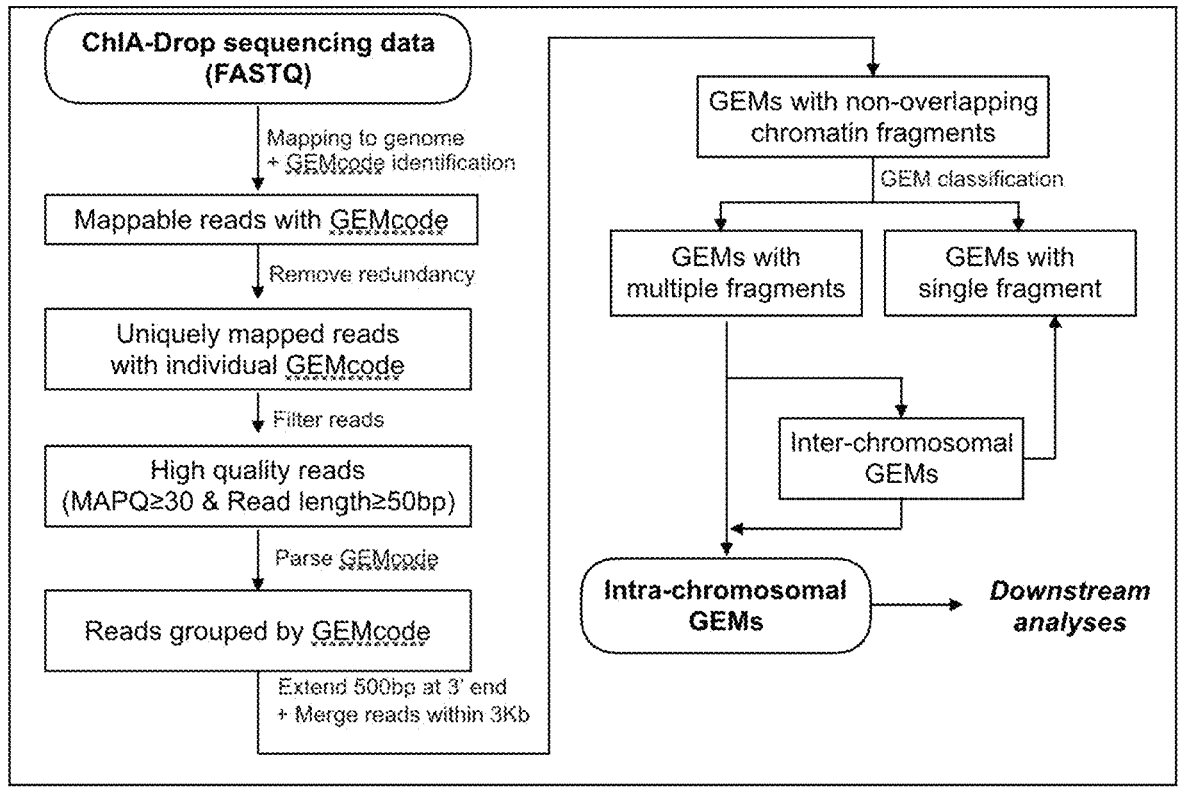

FIG. 16B provides a detailed flowchart of the read alignment, GEM code identification, and GEM calling steps in ChIA-DropBox. FASTQ files are generated and aligned to the reference genome (e.g., *Drosophila* dm3) using the 10X longranger wgs pipeline (v2.1.5, //support.10xgenomics.com/genome-exome/software/pipelines/latest/using/wgs) with default parameters. This generates a BAM file of aligned reads with GEM codes.

GEMcode Identification and Read-Quality Filtering

In this step, GEMcodes were extracted from the BAM file and appended to read ID by accessing the tag field "BX" in the BAM files using the pysam module (v0.7.5) in python (v2.7.9). This re-naming allows the GEMcode to be propagated forward when the BAM files are converted to BED files for downstream analysis.

The new read ID was then comprised of: the library ID, the GEMcode ID, the GEMcode sequence, and the original read ID, each separated by a dash symbol ("-"). An example of a new read ID is: SHG0021N-101294002-TACTTGTTCTTGTATC (SEQ ID NO: 1)-NS500460: 311: HGK53BGX3: 4: 21605: 26065: 15070. In this example, the library ID is "SHG0021N", the GEMcode ID is "101294002", the sequence corresponding to the GEMcode ID is "TACTTGTTCTTGTATC" (SEQ ID NO: 1), and the original read ID is "NS500460:311:HGK53BGX3:4:21605: 26065:15070". For simplicity, only R1 reads, which contain genomic sequences and GEMcodes, were used for analysis in this study. The R2 reads, which come from the other end of the DNA templates and do not contain GEMcodes, are included in the future analysis to improve mapping efficiency. To get high confidence data, only uniquely mapped R1 reads with MAPQ ≥30 and read length ≥50 bp were retained for downstream analyses. These reads were converted to BED format using bedtools (v2.17.0).

Calling Significant Chromatin Complexes (Overview)

Figure 16C:
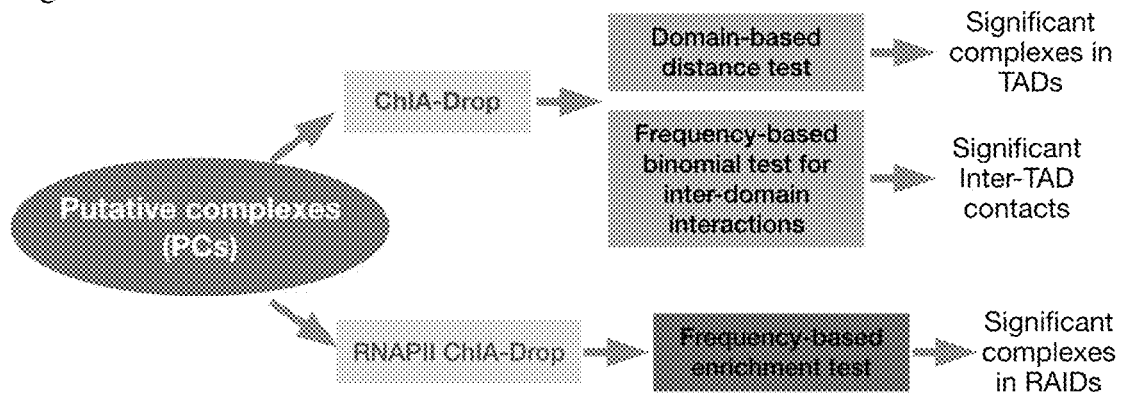

As with any genomic data, the resulting ChIA-Drop putative complexes (PCs) in the previous section are mixtures of true signal and experimental noise. The goal of this section and the next section is to assess the statistical significance of the PCs and retain only confident PCs as significant complexes (SCs). There are distinct methods for ChIA-Drop and RNAPII ChIA-Drop, due to the inherent difference in the nature of the data. ChIA-Drop complexes were first tested for contributions to the domains, with significant complexes in Topologically Associating Domains (TADs); potential noise filtering is included in this step. Using TADs as interaction units, inter-domain interactions were assigned significance based on the frequency of appearance. By contrast, RNAPII ChIA-Drop complexes were tested for enrichment to obtain significant complexes in RNAPII associated interaction domains (RAIDs), resulting in frequent loops. A flowchart of an embodiment of the process is illustrated in FIG. 16C.

Calling Significant Chromatin Complexes (ChIA-Drop)

Figure 17A:
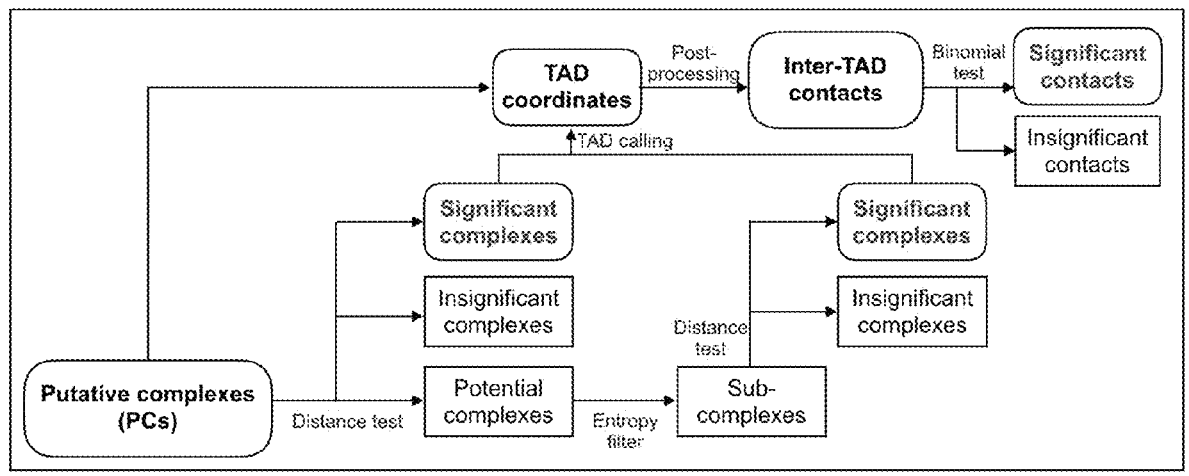
FIG. 17A-C provides a flowchart and diagrams relating to the ChIP-Drop process.

The strategy for ChIA-Drop consists of two levels: i) domain-based distance test to identify significant complexes contributing to the intra-TAD (domain) interactions; ii) frequency-based binomial test to assess inter-TAD contacts by using TAD as a unit and observing frequent interactions among TADs. A flowchart of an embodiment of the process is shown in FIG. 17a.

Figure 25A:
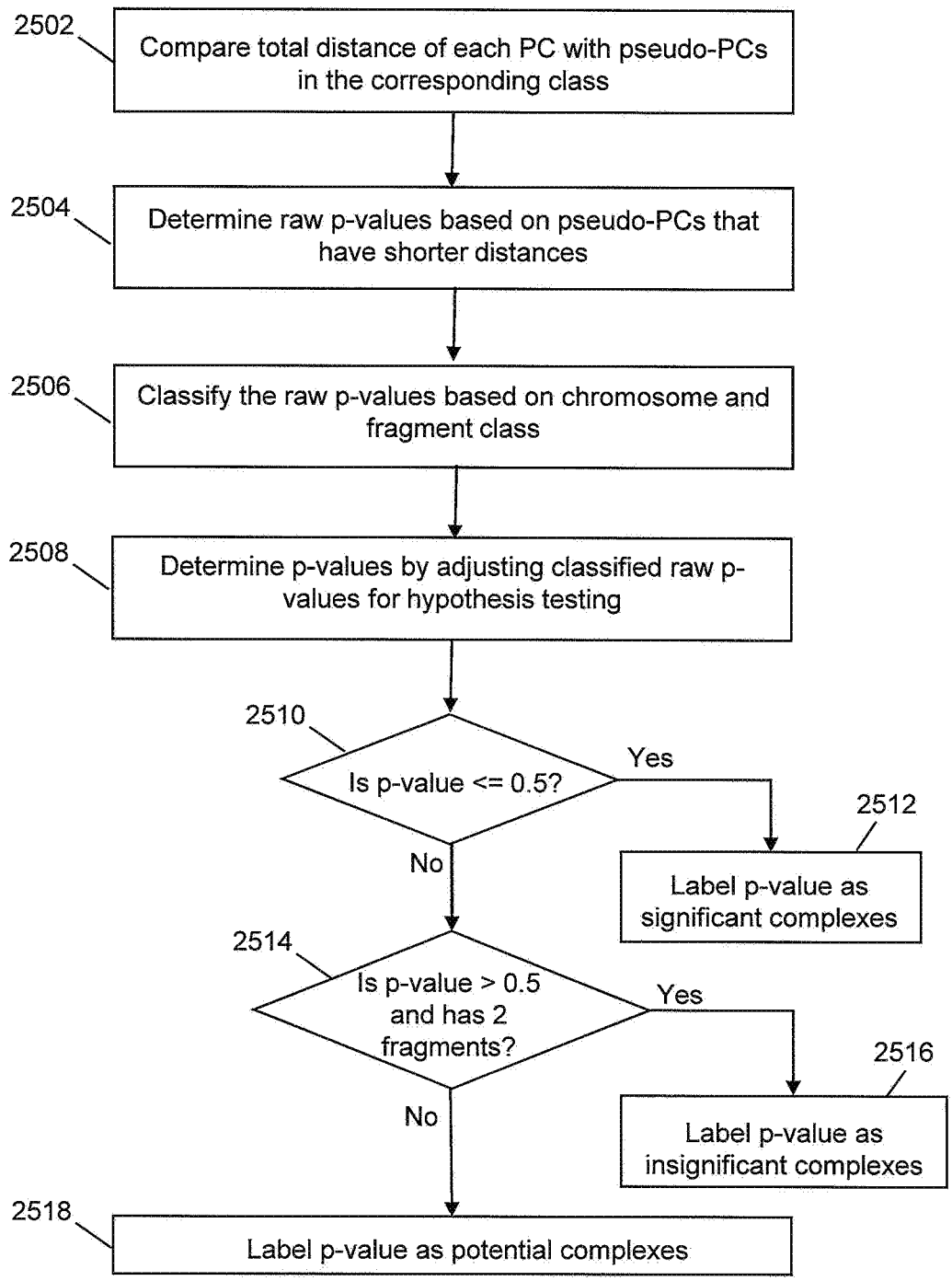
FIG. 25A-B provides flowcharts.

Domain-Based Distance Test i) The first goal was to identify potential technical noise of the system reflected in the ChIA-Drop data. Due to the nature of the droplet approach to partition chromatin complexes, in which the number of complexes in a droplet was assumed to follow the Poisson distribution, a droplet could potentially contain multiple units of chromatin complexes including chromatin singleton fragments. Therefore, it was important to develop an algorithm to distinguish the bona fide complex data from the background noise. Because it is well established that the chromosomes are folded into different topological domains within sub-megabase range (<1 Mb), a domain-based algorithm was developed (see FIG. 25A) to consider the genomic distances among the fragments within a given putative complex (PC). For example, in the following cases, a PC may contain a) a single complex with multiple fragments, b) a complex with a singleton fragment, c) 2 complexes, d) 2 complexes with a singleton, e) 3 complexes, f) 3 complexes with a singleton, etc.

Figure 17B:
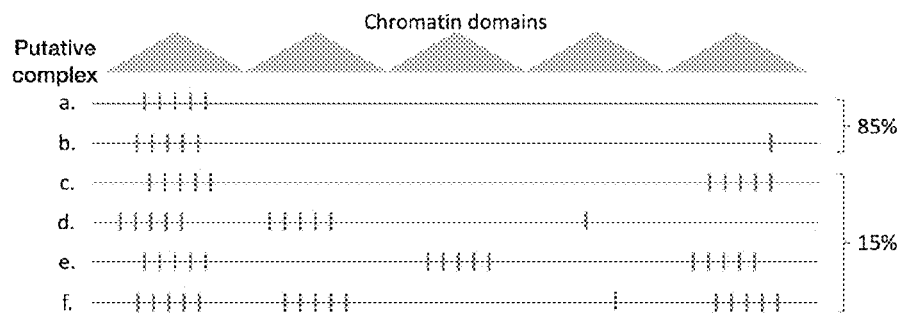

The domain-based distance test aims to distinguish domain-based complex from singleton fragment noise (which was major type of noise in the data) and to identify multiplex complexes potentially included in one droplet. Using this approach, it was possible to assign significance (p-values) to each PC, and further separate PCs to sub-PCs to accommodate cases as exemplified in FIG. 17B.

Figure 25B:
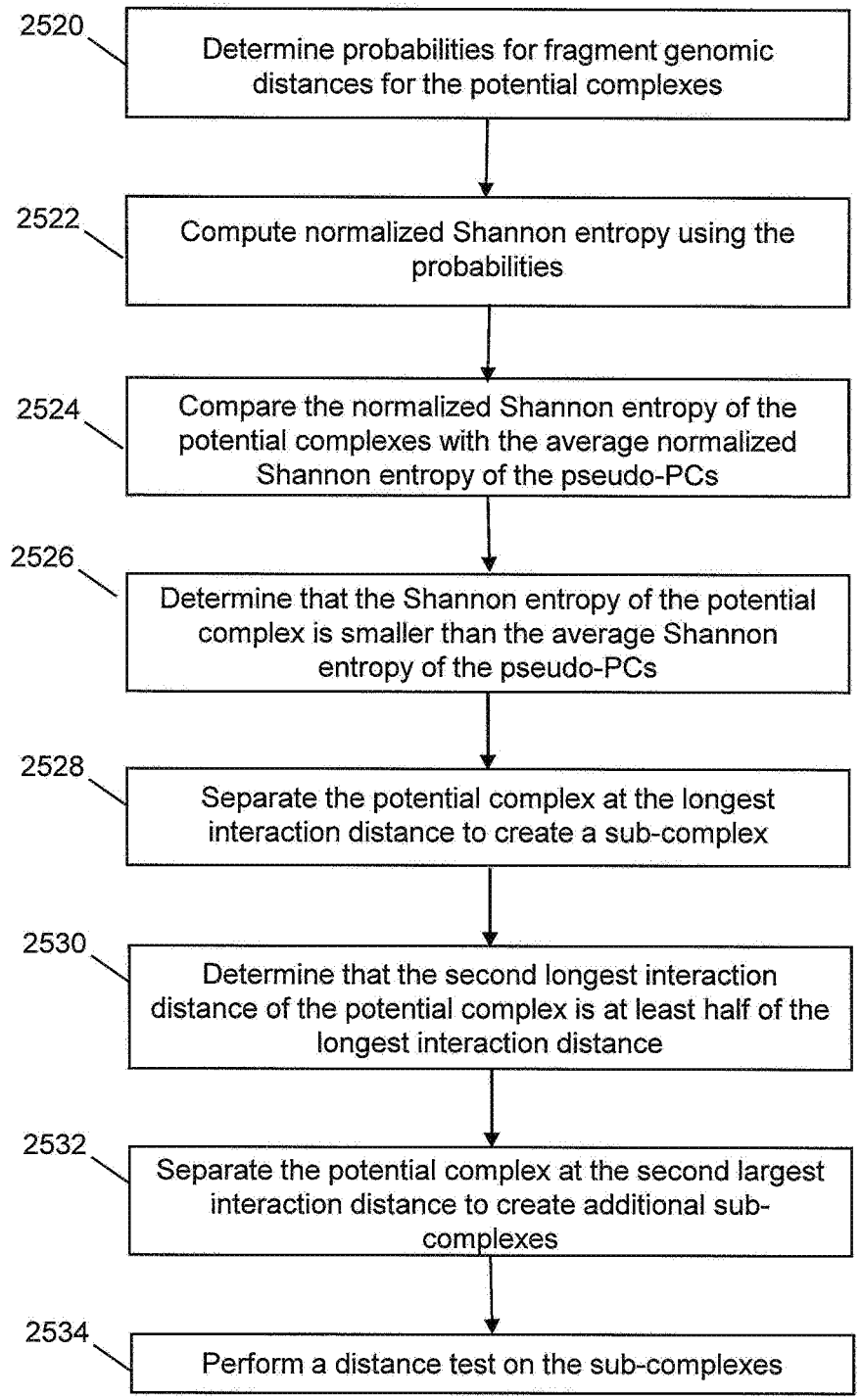

Following the notion that most meaningful interactions occur in certain genomic range, a distance test (see FIG. 25A) was developed. The intuition is that short to mid-range interactions are likely to be signal and unreasonably long-range interactions are likely to be technical noise. To address the latter case, possible experimental artifacts in droplet-based sequencing platform were considered and a noise filtering algorithm to recover true signal was proposed. These two main components, distance tests (see FIG. 25A) and entropy filter (see FIG. 25B), are described in detail below.

The distance test compares the fragment distances of observed PCs with those of the background (null). This null distribution can be derived from the pure DNA experiments; however, pure DNA samples lack high-fragment complexes (F≥10), preventing comparisons in those categories. Thus, theoretical null distributions were simulated by randomly rewiring observed PCs to construct 'pseudo-PCs'. All observed neighboring distances are placed in a bucket, from which $n-1$ distances were randomly drawn with replacement for each fragment class with $n$ fragments. 10000 such pseudo-PCs were simulated in each class. The total distance of each PC was compared to those of pseudo-PCs in the corresponding class (2502), and the proportion of pseudo-PCs that have shorter distances is recorded as the 'raw p-value' (2504). Subsequently the raw p-values were separated by chromosome and fragment class (2506), and adjusted for multiple hypothesis testing (2506) using Benjamini-Hochberg method with false discovery rate (FDR) of 0.05. PCs with adjusted p-value ≤0.05 (2510) were considered 'significant complexes' (2512). From PCs with p-value >0.05, those with 2 fragments (2514) were classified as 'insignificant complexes' (2516) and the rest of 'potential complexes' (2518) were passed onto the entropy filter, which is described next.

The entropy filter (see FIG. 25B) aims to computationally correct for the droplet contamination, where an undesired phenomenon was observed of a droplet containing more than one chromatin complex. It was reasoned that in such an event, sub-fragments in separated by a large distance and should be partitioned into sub-complexes. Specifically, the fragment genomic distances (in bp) are converted to probabilities by dividing each distance by the total distance (2520). Using these probabilities $p_i$ for $i \in \{1,2,\ldots,n-1\}$ for a complex with $n$ fragments, the normalized Shannon entropy $H_{norm}([p_1, \ldots, p_{n-1}])$ was computed as $$\frac{\sum_{i=1}^{n-1} p_i \log_2\left(\frac{1}{p_i}\right)}{\log_2(n-1)},$$

forcing it to range between 0 and 1, inclusively (2522). Generally, $H_{norm}$ will be small when one or two of $p_i$ is large, in which case it is presumed that there are multiple true complexes in a putative complex. For each complex in the 'potential complexes' category, its normalized Shannon entropy was compared to the average normalized Shannon entropy of the pseudo-PCs in the corresponding class (2524); if the former was smaller (2526), then the action was to separate the potential complex at the longest distance interaction (2528). Furthermore, if the second largest distance is at least half of the largest distance (2530), the action was to also separate at the second longest distance interaction (2532). The resulting sub-complexes after necessary separations are now subject to the second distance test (note that statistical testing was not performed in this step; only filtering was performed) (2534).

As a final step, the second distance test was performed on sub-complexes from the noise filtering step. The approach is similar to the first distance test, and sub-complexes are categorized as 'significant complexes' or 'insignificant complexes' depending on the adjusted p-value (with FDR of 0.05). Those PCs and sub-complexes in the 'significant complexes' categories from both distance tests are used for downstream analyses, including TAD calling.

ii) Frequency-Based Binomial Test (for Inter-TAD Interactions)

The previous section identifies significant complexes inside TADs, thereby defining TADs. However, it is also possible for multiple TADs to interact simultaneously (inter-TAD contacts) and studies were undertaken to investigate this larger-scale contact via frequency-based binomial test.

Studies first were performed to process the input PCs by retaining those with at least 5 fragments, with at least 3 fragments in a single TAD, involving 2 or more TADs. The resulting data consist of a pair ['TAD combination', 'PC count'] where 'TAD combination' lists TAD IDs and 'PC count' is an integer denoting the number of PCs in a given TAD combination exclusively. For example, ['a,b', 5], ['a, d', 1], ['a,b,c', 2] indicate that TADs 'a' and 'b' are frequently connected whereas 'a' and 'd' are not. Furthermore, TAD combinations are separated into classes according to the number of TADs in a combination. In the aforementioned example, 'a,b' and 'a,d' are in the same class of 2 TADs and 'a,b,c' is in a higher class of 3 TADs.

Figure 17C:
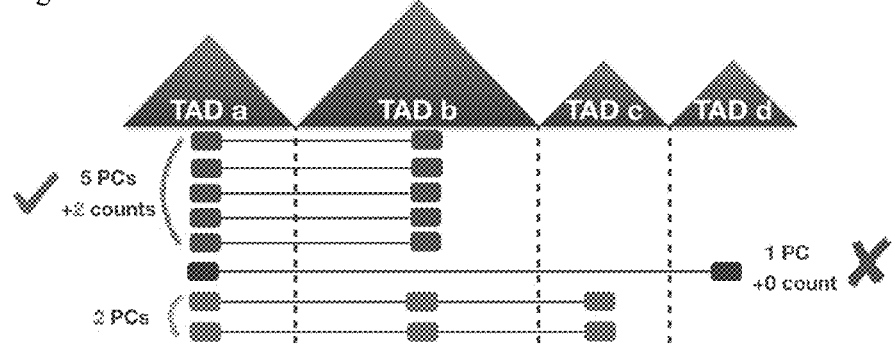

Based on this observation, for each TAD combination, it was quantified how frequent its components were in the same class, and how many times it appeared in higher classes. Using these frequency counts, a one-sided (alt="greater") binomial test was performed for each class, with the null assumption that each combination is equally likely (i.e., expected probability is 1/number of combinations). With p-value cutoff of 0.05, highly frequent inter-TAD contacts and PCs connecting those TADs were identified. FIG. 17C provides an illustrative example of an embodiment of the process.

This section utilizes pandas, numpy, randon, statsmodels, and itertools modules in python (v3.6.0)

Calling Significant Chromatin Complexes (RNAPII ChIA-Drop)

The RNAPII-enriched ChIA-Drop data show more homogeneity than its non-enriched counterpart, and thus a frequency-based enrichment test was developed. The idea is that if a fragment is covered by many other PC fragments, then it is likely a strong binding site and more likely to be a true interaction. This concept is analogous to the practice of selecting ChIA-PET loops with at least one anchor supported by a peak.

Specifically, PC fragments are piled up to generate fragment coverage track (via bedtools v2.27.1). For each observed PC, an enrichment score was computed as the mean coverage, averaged over the fragment. The expected enrichment score was computed for a pseudo-PC, which retains the same fragment lengths and distances but is randomly placed in the chromosome. By generating 10000 pseudo-PCs for each PC, a raw p-value was computed as the proportion of pseudo-PCs with higher score than the observed score. These raw p-values were subsequently adjusted for multiple hypothesis testing using Benjamini-Hochberg method with false discovery rate (FDR) of 0.1. Finally, PCs with adjusted p-value ≤0.1 were considered as 'significant' and others as 'insignificant'.

Data Visualization

File Formats for Data Visualization

ChIA-DropBox includes utilities for converting ChIA-Drop data files into file formats compatible with most visualization tools. The file formats generated by ChIA-DropBox are summarized below.

The file formats for pairwise visualization tools are:
 a) .bedpe file of the chromatin interactions converted to pairwise contacts
 b) .loops file is a BEDPE file of loops (i.e., after the pairwise contacts are extended and merged into loops)
 c) .hic files for 2D contact map visualization in Juicebox The file formats for multi-fragment visualization tools:
 a) .region files for ChIA-DropBox's Linear Multi-Fragment Viewer.
 b) .gff files for IGV view multi-fragment The file format for visualizing the fragment coverage is:
 a) .rcov and .fcov are bedgraph files for read coverage and fragment coverage.

Figure 26:
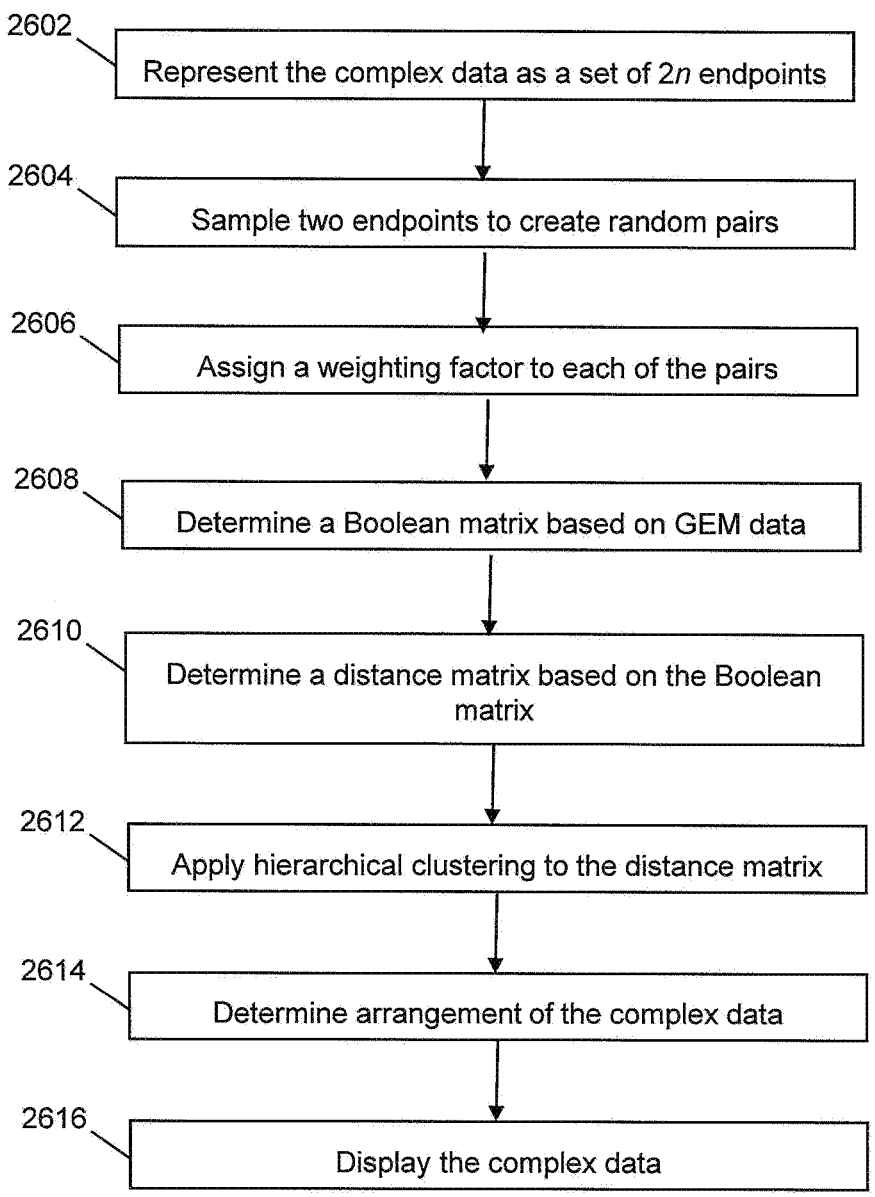
FIG. 26 provides a flowchart.

Juicebox 2D Contact Map Visualization (see FIG. 26)

ChIA-Drop data is converted to pairwise contacts, and then a .hic file is created using Juicer tools to visualize 2D contact map in Juicebox. Using 2D contact maps, comparing a new ChIA-Drop dataset to an existing ChIA-Drop dataset or Hi-C dataset provides quality-control assessment for the new dataset.

In theory, the ChIA-Drop and Hi-C protocols should capture comparable chromatin interactions. However, there are fundamental differences between the two datasets that needs to be considered. The output of a ChIA-Drop experiment is a collection of chromatin complexes, each with multiple fragments, whereas the Hi-C protocol generates only pairwise interactions detected by proximity ligation between two ends of the same (self-ligation) or different (inter-ligation) DNA fragments. For instance, a chromatin complex with 10 fragments identified by ChIA-Drop implies that these 10 loci were all in close contact. However, it would not be possible for a Hi-C experiment to capture all possible 45 pairwise interactions from this complex with 10 fragments within the same cell; by the nature of the experimental technique, the ligated DNA ends are no longer available to be ligated with other proximal DNA fragments. Considering that a Hi-C experiment is a random sampling process that produces a subset of all possible proximity ligation events from millions of cells, two down-weighting algorithms were conceived to best mimic the Hi-C pairwise output from the ChIA-Drop data, as detailed below.

ChIA-Drop complex data was converted into pairwise Hi-C-like data based on an algorithm that simulates Proximity Ligation In Silico by Random Sampling (PLISRS), a specific program developed for this purpose. In PLISRS, each chromatin complex was considered as a set of $n$ fragments and each fragment has two endpoints available to be ligated. Thus, a complex could be represented as a set of $2n$ endpoints (2602) and 2 endpoints from the set can be randomly sampled without replacement ('random' module in python v3.6.3) (2604). Note that it is possible to choose two endpoints from the same fragment (self-ligation). The process is iterated k times for all complexes, and the sampled pairs are de-duplicated.

To characterize the expected behavior of the above simulation when iterated infinite number of times without de-duplication, a program was developed to refer Proximity Ligation by Expected Convergence (PLEC), and convert the ChIA-Drop complex data into pairwise interactions with weighting factors (2606). This method is based on an assumption that all fragments will be ligated during an overnight proximity ligation in Hi-C experiments. Thus, there will be $n$ ligations for a chromtine complex with $2n$ endpoints when they are all ligated. The probability of self-ligations and inter-ligations was further calculated. Given $n$ possible self-ligations, each self-ligation has a probability $$\frac{2}{2n} \cdot \frac{1}{2n-1} = \frac{1}{n(2n-1)},$$

each inter-ligations has a probability $$2 \cdot \frac{2}{2n} \cdot \frac{1}{2n-1} = \frac{4}{n(2n-1)}.$$

Consequently the expected value of the interaction frequencies per the n fragment complex is $$\frac{1}{n(2n-1)} \cdot n = \frac{1}{2n-1}$$

for self-ligations and $$\frac{4}{n(2n-1)} \cdot n = \frac{4}{2n-1}$$

for inter-ligations. These expected values were then used as weighting factors to convert the ChIA-Drop complex data into pairwise Hi-C-like data for fair comparisons.

The following three BEDPE files were used to generate .hic files for the Juicebox visualization: 1) all pairwise interactions; 2) random sampling with PLISRS using 5 iterations (k=5) and de-duplication; 3) all pairwise interactions adjusted by PLEC weighting factor $$\frac{1}{2n-1}$$

for self-ligations and $$\frac{4}{2n-1}$$

for inter-ligations (where $n$ is the number of fragments in the complex). BEDPE files were converted into Juicer short format for the first two cases, and Juicer short with score format for PLEC. The weighting factor in PLEC is the score in the Juicer input format. Then, hic files were produced by Juicer tools (pre commend, version 1.7.5) using various resolutions from 2.5 Mb to 1 Kb with reference genome, and they were visualized by Juicebox either PC version (version 1.9.0) or web version (Juicebox.j s, version 1.1.2).

Loop Visualization

ChIA-DropBox identify the loop based on prior ChIA-PET protocol. Briefly, paired-end tags (PETs) were aligned to the reference genome and only uniquely-mapped, non-redundant PETs are retained. Then, each tag was extended by 500 bp in its 5' direction and PETs that have both ends (R1 and R2) overlapping were merged into loops. The interaction frequency of each loop was then the number of PETs that contributed in ChIA-PET.

To make the loop-based visualization of ChIA-Drop data (converted to pairwise contacts) directly comparable with loops from ChIA-PET data, ChIA-DropBox includes a utility for converting ChIA-Drop data into a format that can be processed with the existing ChIA-PET pipeline. Specifically, ChIA-Drop interactions are converted to pairwise contacts (a BEDPE file). Then, the BEDPE file and reference genome FASTA file are used to create "pseudo paired-end FASTQ files" by extracting the sequences of interacting fragments from the reference genome. These pseudo paired-end FASTQ files are then processed by the ChIA-PET pipeline, so that the loops visualized for ChIA-Drop data are directly comparable with the loops visualized for ChIA-PET data. The loops can then be visualized in genome browsers.

Multi-Fragment Visualization

To visualize multiplex chromatin interaction complexes in a genome browser-based view, a custom R tool, called Linear Multi-fragment Viewer (LMV) was developed, which displays the chromatin fragments in each GEM unit along a linear genome-browser view. Along the y-axis, GEMs are arranged by similarity, which is computed via clustering methods (e.g., hierarchical clustering based on a distance matrix).

Briefly, this clustering of the GEMs is performed as follows. A genomic region of interest is binned by either a certain number of bins (100 bins in default) or a manually defined size (e.g. 1 Mb/bin), and then a Boolean matrix is constructed from the GEM data: for every row (GEM), each column (bin) is assigned a value of 1 only if that GEM has a fragment in that bin (2608). The Boolean matrix is then used compute a distance matrix between the GEMs (n×n) (2610), and hierarchical clustering is applied to this distance matrix (2612). Data processing, clustering and matrix visualization are performed mainly using bedtools (v2.27.1), and the R (v3.5.1) package pheatmap (v1.0.10).

After performing the hierarchical clustering to determine the arrangement of the GEMs (2614), the GEMs were plotted with their un-binned, high-resolution fragment information (2616). In the Linear Multi-fragment Viewer (LMV), each row is a GEM complex. The entire GEM span is indicated with a thin line, and the individual fragments are displayed with thick segments. The visualization was performed using R (v3.5.1) package ggplot2 (v3.0.0).

Other R packages used in clustering heatmap view and linear multi-fragment visualization include: dplyr (v0.7.6), bedr (v1.0.4), ggforce (v0.1.3), cowplot (v0.9.3), gtable (v0.2.0), gridExtra (v2.3), reshape2 (v1.4.3), RColorBrewer (v1.1-2), ggrepel (v0.8.0), and ggpubr (v0.1.7).

Results

Figure 18A:
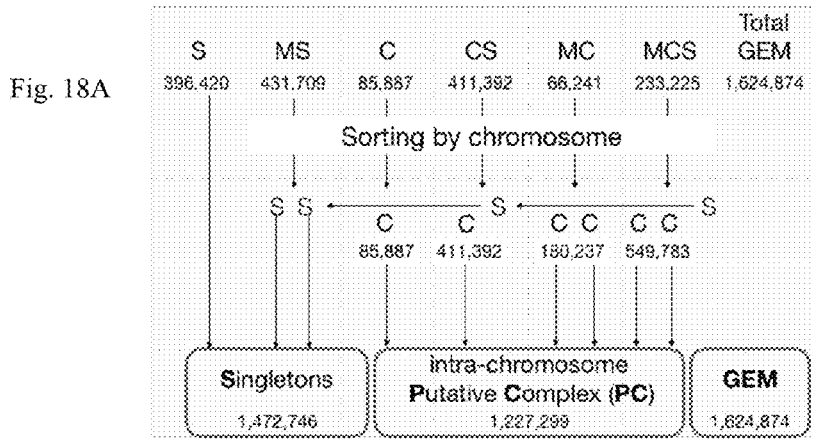
FIG. 18A-D provides a diagram, graph, contact maps, and histograms illustrating how ChIA-DropBox processes ChIA-Drop data.

To demonstrate how ChIA-DropBox processes ChIA-Drop data, detailed results are provided using one lane of sequencing data from ChIA-Drop Rep2. The ChIA-Drop sequencing reads have a maximum length of 130 bp (FIG. 6), and there were 285,954,653 paired-end reads. High quality sequencing reads (MAPQ ≥30, read length ≥50 bp) were extended for 500 bp from the 3' ends, and merged into chromatin fragments (as described in the previous method section). The average fragment length is 630 bp. Fragments sharing the same origin of GEMcode were grouped as a GEM unit, reflecting the chromatin composition. An example is shown in FIG. 18A. 51M unique non-redundant reads were obtained and assembled into 5.7M chromatin fragments (about 10 reads/fragment). Based on GEMcode, the fragments were assigned into 1.6M GEM droplets. The GEMs were then sorted based on the number of fragments and chromosome origins to classify them (see FIG. 19A). For example, 396,420 GEMs contained only one fragment per GEM (designated as singleton GEM, S). There were also many GEMs with multiple fragments but all from different chromosomes, therefore designated mixed singleton GEM, MS. It was possible to identify GEMs with multiple fragments all from the same chromosome, potentially representing a chromatin complex, designated C GEMs. There were also C GEMs including singletons, designated CS GEMs; mixed C GEMs, designated MC; and mixed C GEMs with singletons, designated MCS GEMs. Using this sorting logic, 1,227,299 potential intra-chromosome chromatin complexes were identified from the 1,624,874 GEMs. It also included 1,472,746 singletons. These putative complexes were then subjected to a significance test. From this these statistical breakdowns, it could been seen that singleton fragments are a major source of noise, but can be readily identified and removed. The "domain-based" distance test can further assess the significance of each of the intra-chromosomal complexes, and dissect the complexes to identify possible intra-chromosomal singletons (see below for significance tests).

Both replicates of ChIA-Drop data were combined in this study and process with the same pipeline. By extending and merging reads within 3 kb, 3,075,926 intra-chromosomal GEMs were obtained that contain multiple chromatin fragments (F≥2). Further details on the genomic coordinates of multiplex GEMs with 10 or more fragments (F≥10) were obtained. Without the 3 kb extension step, there were 3,144,087 intra-chromosomal GEMs with F≥2, collectively called 'putative complexes' (PCs), which are subject to the significant complex calling step.

Figure 18B:
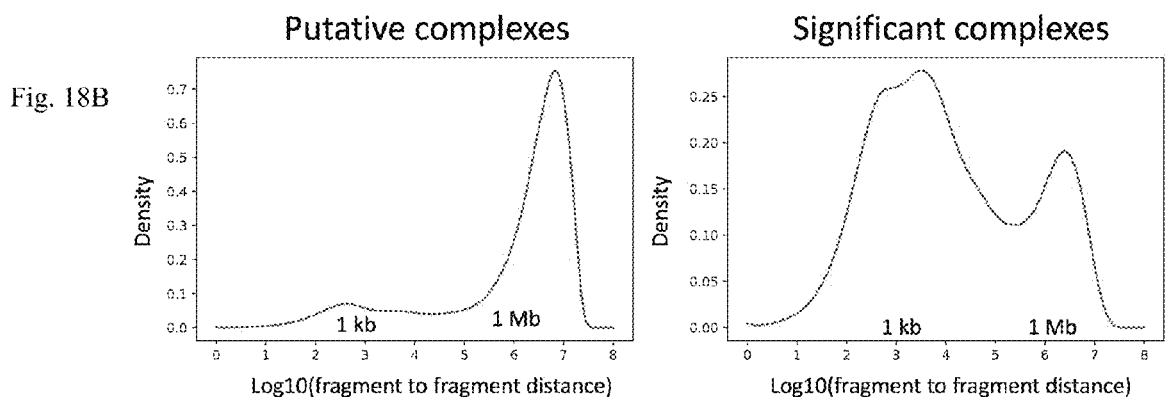

Using FDR of 0.05, 59,304 statistically significant chromatin complexes were identified. Moreover, the fragment to fragment distances are much shorter for significant complexes than that in the original putative complexes (PCs). This result is supportive of the shift in the density curve after significant calling, shown in FIG. 18B.

Figure 18C:
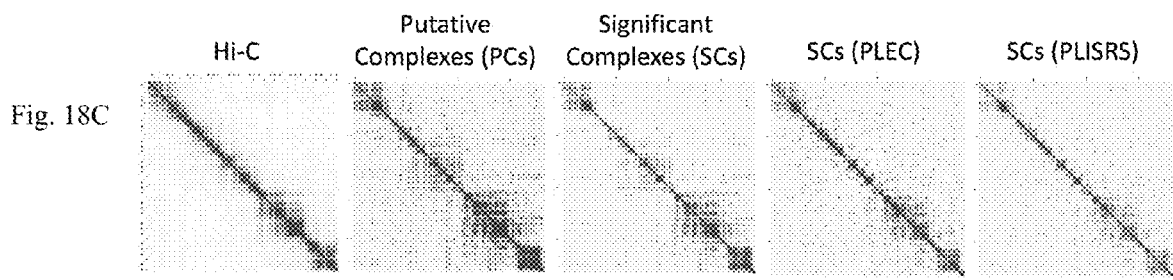

Before the 2D contact map generation, PLEC and PLISRS were applied. 2D contact maps of chr2R: 3 Mb-4.8 Mb with 5 kb resolution using balanced normalization present in FIG. 18C, as an example.

Figure 18D:
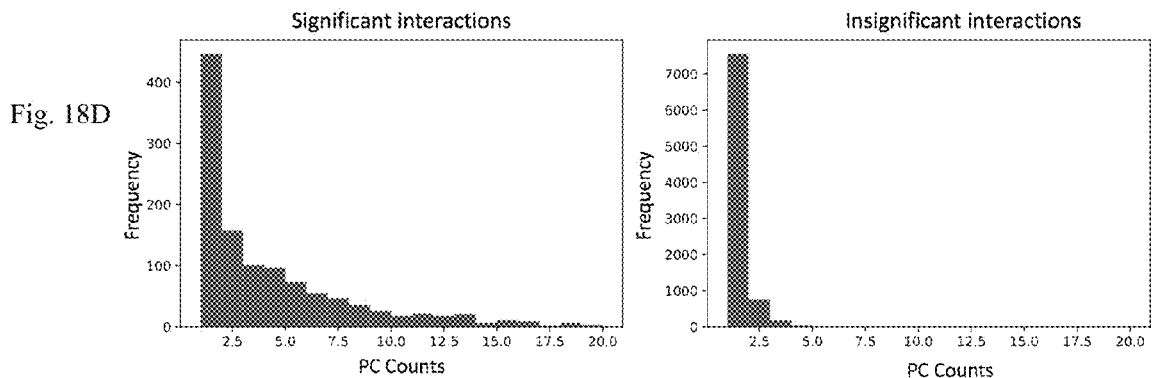

Using 583 TADs as an interaction unit and from filtering process outlined above, there were 9723 combinations of TAD interactions, of which 1168 (12%) were called as significant by the frequency-based binomial test. Similarly, 4757 out of 14630 PCs (32%) in these combinations passed the test. FIG. 18D shows histograms of PC in which counts in the 'significant' (left) and 'insignificant' (right) categories show that in general, frequent interactions (high PC counts) are called significant and infrequent interactions (low PC counts) are called insignificant. Note that it is possible for interactions with only 1 PC count to be significant due to its appearance in higher classes.

Figure 19A:
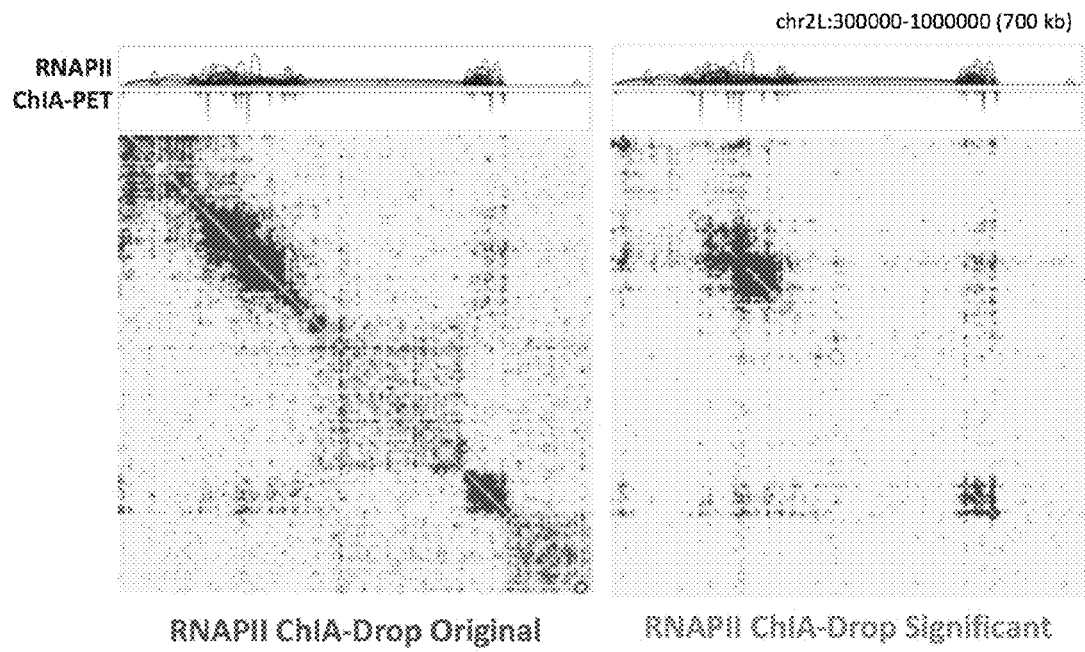
FIG. 19A-B provides a heatmap and loop views. The statistically significant RNAPII ChIA-Drop complexes are enriched in RAIDs, centered around strong peaks, and are depleted in between RAIDs. In addition, the significant complexes constitute highly frequent loops, corresponding to high PET counts in ChIA-PET loops.
Figure 19B:
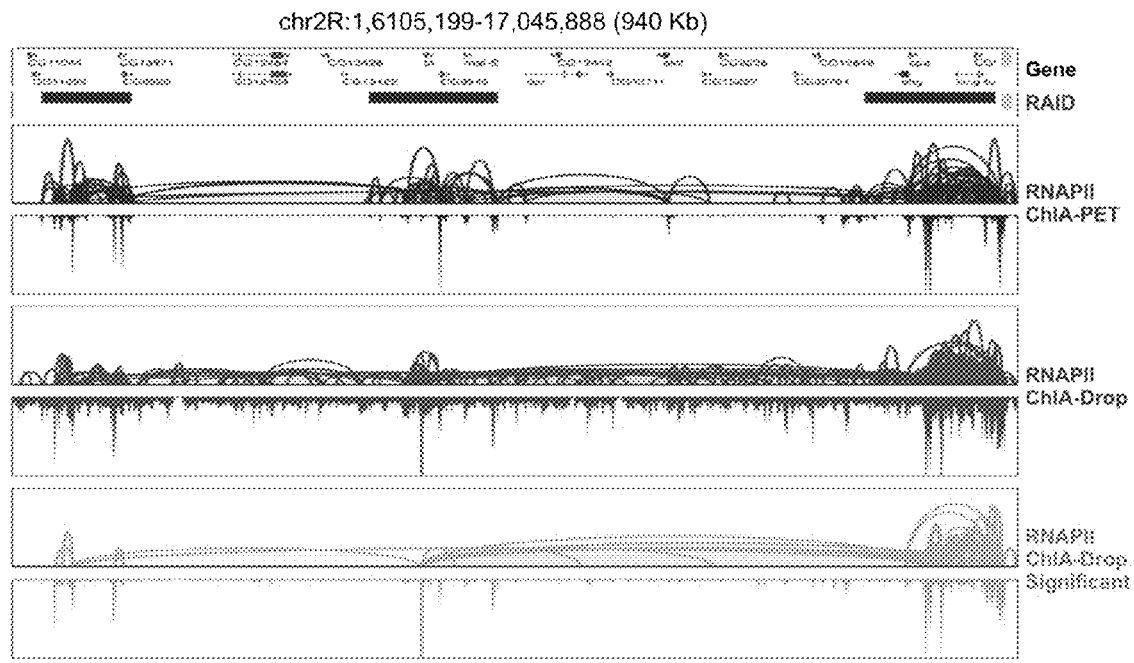
Figure 20A:
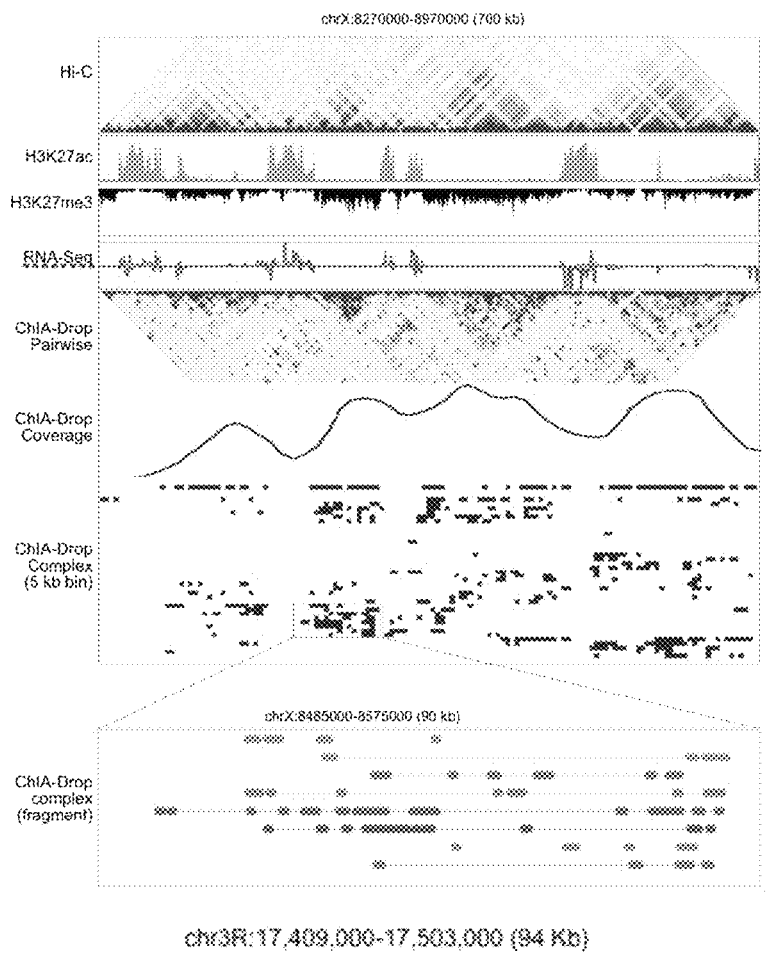
FIG. 20A-B provides a fragment-alignment diagram and a loop view. ChIA-Drop data can be visualized linearly as fragment alignment (FIG. 20A) and RNAPII ChIA-Drop data can be converted into pairwise loops (FIG. 20B).
Figure 20B:
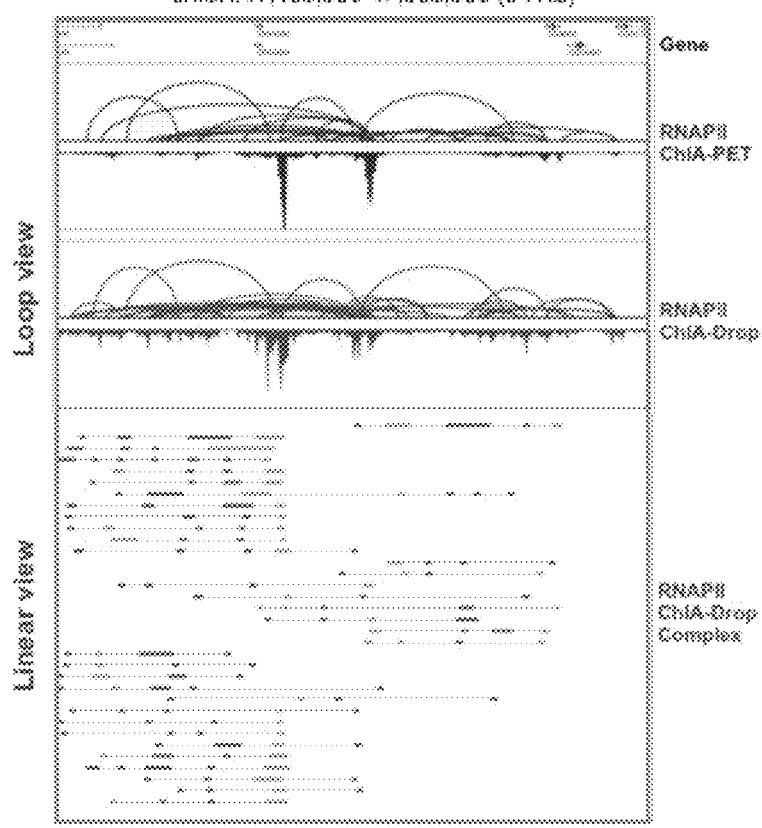

RNAPII ChIA-Drop have 3,921,637 PCs, and 1,802,845 (~46%) passed the frequency-based enrichment test using FDR of 0.1 and 10000 pseudo-PCs. As a result, the statistically significant RNAPII ChIA-Drop complexes are enriched in RAIDs, centered around strong peaks, and are depleted in between RAIDs. In addition, the significant complexes constitute highly frequent loops, corresponding to high PET counts in ChIA-PET loops. Examples of heatmap and loop views are shown in FIGS. 19A and 19B, respectively Furthermore, ChIA-Drop data can be visualized linearly as fragment alignment and RNAPII ChIA-Drop data can be converted into pairwise loops, as shown in FIG. 20A-B.

Example 3

RNAPII ChIA-PET Data Analysis

The raw reads from RNAPII ChIA-PET and in situ RNAPII ChIA-PET derived from *Drosophila* S2 cells were processed as follows. The linker sequences were trimmed off and paired-end tags (PETs) were aligned to the *Drosophila* reference genome (dm3). Uniquely mapped and non-redundant PET reads were classified as self-ligation PETs or inter-ligation PETs. Inter-ligation PETs were further clustered together if both tags (with a 500 bp extension) overlapped. Clusters with PET counts of 2 or more (PET≥2) were considered as candidates for further analysis of chromatin interaction loops. Chromatin loops with higher PET counts reflect frequent contacts, and are considered high confidence data.

Identification of RNAPII-Associated Interaction Domains (RAIDs)

Based on chromatin loop intensity and connectivity from the RNAPII ChIA-PET data, RAIDs were defined in *Drosophila* S2 cells in this study. Density plot of RNAPII-associated chromatin interaction loop span (genomic distance) and contact frequency (PET count) shows a bimodal distribution of 2 populations of chromatin contacts, the mid-range from 10 kb to 100 kb, and the long-range larger than 1 Mb (≥1 Mb). The PET count in each chromatin interaction loop reflects the contact frequency. The loops with more PET counts are high frequent and high confidence. Most of the high confidence loops showed high proportion in the mid-range and very low in long-range. On the contrary, most of the low confidence data (with low PET counts) are in long-range. Chromatin loop data with 4 and more PET counts (PET≥4) are considered as high quality for further RNAPII-associated interaction domain (RAID) analysis (FIG. 12B). When plotting log 10 loop-span distribution, the histogram shows a bimodal Gaussian distribution, which prompted work to fit a mixture of two Gaussian distributions by the Expectation-Maximization algorithm ('normalmixEM' function of the R package 'mixtools'). By observing that the majority of the population belonged to mid-range interactions with mixing coefficients greater than 0.65, 100 kb was subsequently taken as a threshold because it is close to the transition point of the mixture models (FIG. 12C). This threshold was then used to filter RNAPII loops to be including when demarcating RAIDs. Only those connected domains containing at least three loops were selected as RAIDs structures. Finally, 476 RAIDs were defined. Majority of loops with 4 and more PET counts (PET≥4) are located within RAID (intra-RAID loops) with stronger interactions (FIG. 12D). There is also a subset of loops that have longer span and connecting RAIDs (inter-RAID loops) and less frequent (FIG. 12E). Summary statistics of RAIDs are: minimum=13,349 bp, mean=13,2901 bp, median=98,319 bp, maximum=619,810 bp.

Summary Statistics of ChIA-Drop and RNAPII ChIA-Drop Data

The ChIA-Drop raw sequencing reads were processed as described in ChIA-DropBox (see Example 2), and resulted in 5,694,441 GEMs. Summary statistics and the genomic coordinates of multiplex GEMs with 10 or more fragments (F≥10) were obtained. Similarly, RNAPII ChIA-Drop data captured 13,218,812 GEMs, and the genomic coordinates of high multiplex GEMs (26,314) with six or more fragments (F≥6) were obtained.

Calculation of Insulation Scores to Identify Topologically Associating Domains (TADs)

Figure 21:
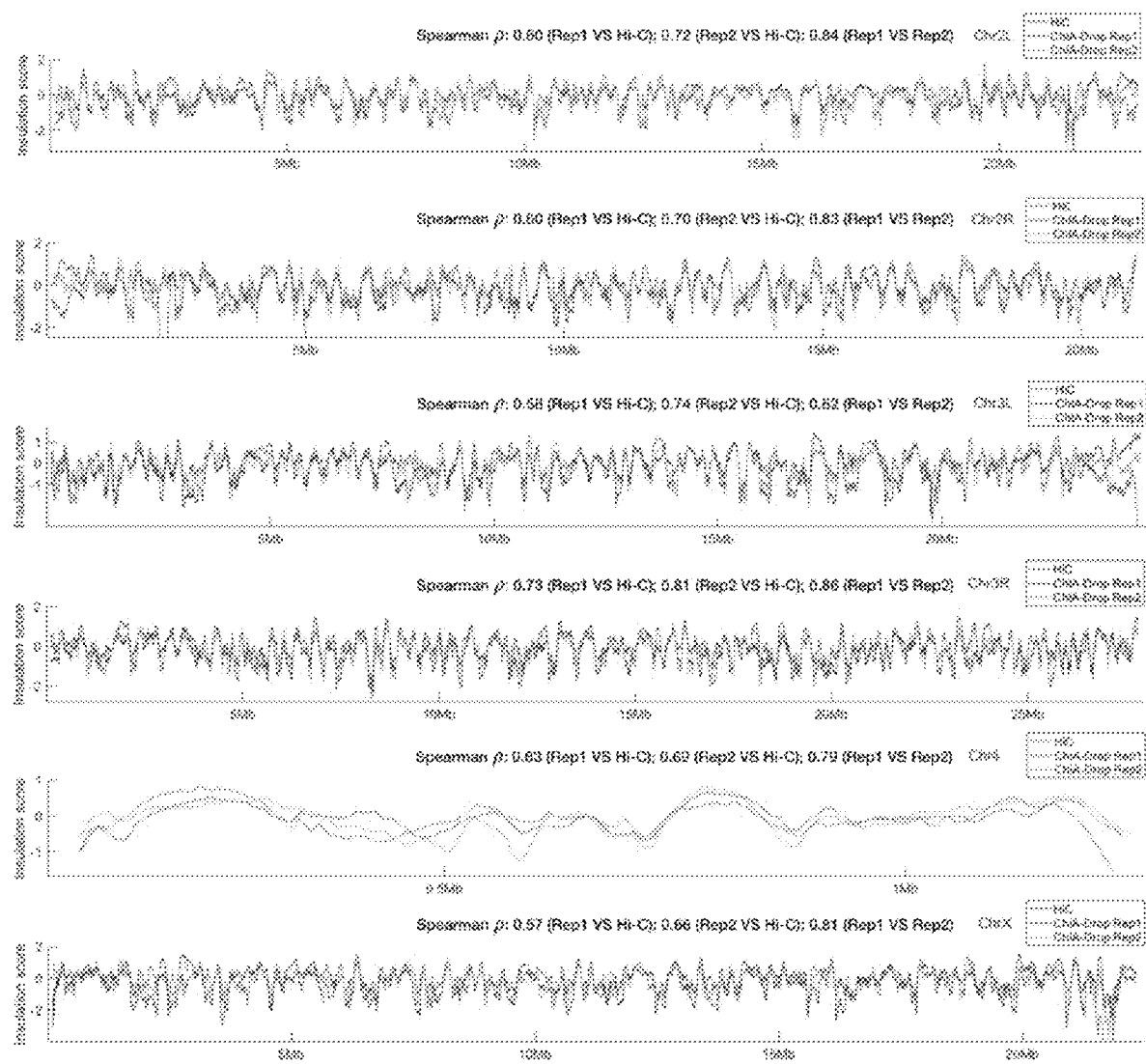
FIG. 21 provides insulation score curves for six chromosomes, including from top to bottom: Chr2L, Chr2R, Chr3L, Chr3R, Chr4, and ChrX.

Using both insulation scores and TADs, ChIA-Drop was compared with Hi-C. First, contact matrices were extracted from Juicebox contact map files (.hic) using Juicer 'dump' function with a dense matrix option (-d) in the Juicer tool (v1.7.5). Then, insulation scores were calculated using a 100 Kb insulation square size and a 100 Kb delta window size for 10 Kb resolution contact maps with balanced normalization. These values were chosen after various parameter values were tested. Overlapped insulation boundaries were merged, and then the genomic region in between two insulation boundaries was identified as TAD. Insulation scores were calculated for ChIA-Drop Rep1, Rep2, and Hi-C. FIGS. 1B and 1C show the calculated insulation score curves of three data sets for chr2L. Insulation score curves for all six chromosomes were prepared (see FIG. 21). In addition, Spearman correlation coefficient (r) of the insulation scores were calculated between ChIA-Drop Rep1 and Hi-C (0.62 for all six chromosomes); ChIA-Drop Rep2 and Hi-C (0.73 for all six chromosomes); ChIA-Drop Rep1 and ChIA-Drop Rep2 (0.83 for all six chromosomes). Overall, both ChIA-Drop Rep1 and Rep2 are correlated with Hi-C, based on the correlation coefficients and insulation score curves.

TAD statistics between ChIA-Drop and Hi-C were also calculated and compared. The total TAD count for Hi-C is 530, and the average TAD length is 153 Kb. The total TAD count for ChIA-Drop Rep2 is 522, and the average TAD length is 155 Kb. The overlapping TAD percentage of HiC to ChIA-Drop is 82% for ChIA-Drop Rep1 and 84% for ChIA-Drop Rep2. The following table (Table 2) summarizes the TAD statistics.

TABLE 2

| TAD | ChIA-Drop Rep1 | ChIA-Drop Rep2 | Hi-C |
|---|---|---|---|
| Total count | 471 | 522 | 530 |
| Average length | 180,703 bp | 155,270 bp | 153,077 bp |
| Total length | 85,111,081 bp | 81,051,030 bp | 81,131,022 bp |
| Min length | 10 Kb | 10 Kb | 10 Kb |

TABLE 2-continued

| TAD | ChIA-Drop Rep1 | ChIA-Drop Rep2 | Hi-C |
|---|---|---|---|
| Median length | 170 Kb | 140 Kb | 150 Kb |
| Max length | 580 Kb | 490 Kb | 490 Kb |

Reproducibility Analysis of ChIA-Drop Data Using HiCRep

ChIA-Drop reproducibility was assessed as follows. HiCRep (v1.2.0) was used to compute the stratum-adjusted correlation coefficient (scc) between all pairs of the following datasets, each with two replicates: ChIA-Drop, RNAPII ChIA-Drop, RNAPII ChIA-PET, and Hi-C (FIG. 7B). First, the 'dump' function in Juicer tools (v1.6.2) was used to convert each ".hic" file to a set of dense matrices at 100 Kb resolution, with one matrix per chromosome. For ChIA-Drop and Hi-C the normalization option used was 'KR' (matrix balancing), while for RNAPII ChIA-Drop and RNAPII ChIA-PET the option used was 'none' (the signal enrichment in these data types is not consistent with the assumptions of matrix balancing). For each pair of datasets being compared, the scc is computed for each chromosome using a smoothing size (h) of 3 and a maximum distance of 1 Mb, and then the scc is averaged across chromosomes (FIG. 7B).

Comparison of Pairwise Contact Spans in Various Chromatin Interaction Datasets

To characterize the loop span of ChIA-Drop and RNAPII ChIA-Drop data, 10,000 contacts were randomly subsampled from all pairwise interactions in each dataset. This set of contacts was further decomposed by the number of fragments in the GEM of its origin. The empirical cumulative distribution function (ECDF) of genomic spans were plotted for subgroup of GEMs with 2, 3, 4 fragments (F=2, F=3, F=4), etc. via stat ecdf function of the ggplot2 package in R.

A/B Compartment Calling by Eigenvector

Figures 22, 23A:
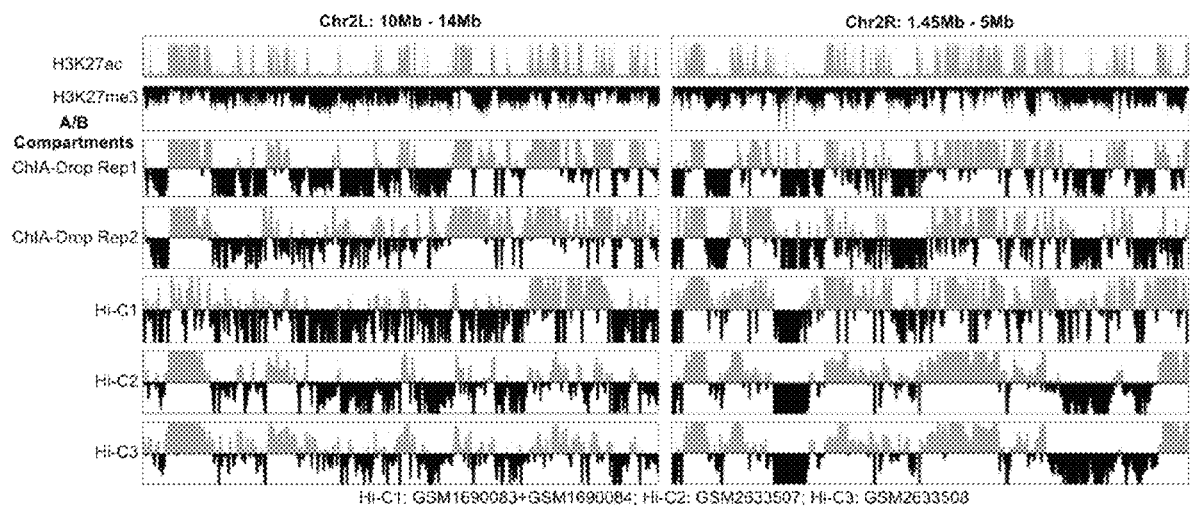
FIG. 22 provides a diagram presenting A and B compartments with epigenomic markers (H3K27ac for active marker; H3K27me3 for inactive marker) for two genomic regions (chr2L:10 Mb-14 Mb; ch2R: 1.45 Mb-5 Mb).
FIG. 23A-B provides tables showing result analysis of hypothetical examples of a TAD and a RAID, both binned at 5 Kb resolution.

The 'eigenvector' function in Juicer tools (v1.7.5) was used to generate the first component of PCA (Principal Component Analysis) for the contact map. To match with A compartment for positive value and B compartment for negative value, the active and inactive domain was used as the input signal to assign A and B compartment per each chromosome. The intersect of active domain and positive value in the first component value, and the intersect of inactive domain and negative value in the first component value, were calculated using bedtools (v2.26.0). Finally, the ratio of sum of two intersect domain length to sum of active and inactive domain per each chromosome were obtained. If the ratio was larger than or equal to 0.5, the same value was used to assign A and B compartments. Otherwise, the value was flipped over to assign A and B compartments per each chromosome. A and B compartments are presented with epigenomic markers (H3K27ac for active marker; H3K27me3 for inactive marker) for two genomic regions (chr2L:10 Mb-14 Mb; chr2R:1.45 Mb-5 Mb) in FIG. 22, as an example. Overall, A and B compartments in ChIA-Drop Rep1 and Rep2 match with two epigenomic markers as well as A and B compartments in Hi-C. 10 Kb resolution, balanced normalization contact map was used to generate these A and B compartments for both ChIA-Drop and Hi-C.

Identification of Transcriptional Active and Inactive Domains

To study the relationship between chromatin structure and transcription activity, transcriptionally active and inactive domains were defined. Three data sets in BEDGRAPH format were used as the input: RNA-seq, H3K27ac and H3K27me3 ChIP-seq. The signal of each data set smoothened using the by applying a rectangular moving averages filter, where the window size is the average gap length (filtfilf function of the 'signal' package in R). These smoothened signals were segmented with the Binary Segmentation algorithm ('cpt.meanvar' function with Q=100, minseglen=5000 of the 'changepoint' package in R). The segments with estimated mean greater than 5 were retained and recorded its chromosome name, start position, end position, and estimated mean. The three resulting bedGraph files were concatenated ('unionbedg' function with—empty of the bedtools), where each line has a set of unique estimated mean from RNA-seq, H3K27ac, and H3K27me3, along with its chromosome name, start position, and end position. Intuitively, a segment with high RNA-seq and H3K27ac signal coupled with low H3K27me3 signal implies a transcriptionally active region. Next, small nearby regions were iteratively merged to obtain 708 active regions across chromosomes 2L, 2R, 3L, 3R, 4, and X. Finally, the complements of active regions are defined as inactive regions ('complement' function of the bedtools). An example is shown in FIG. 4A.

Reproducibility of ChIA-Drop Libraries

In general, replicates of each dataset showed reasonably high correlation coefficient values (FIG. 7B and FIG. 8). When comparing different types of datasets, ChIA-Drop and Hi-C were considered more comparable for data for overall chromatin contacts; whereas RNAPII ChIA-Drop and RNAPII ChIA-PET are comparable for transcriptional chromatin interactions. For ChIA-Drop vs Hi-C, the pairwise (4-set comparisons) correlation coefficient values were from 0.58-0.73, indicating considerable similarity with certain difference. For RNAPII ChIA-Drop vs RNAPII ChIA-PET, the correlation coefficient values were from 0.51-0.57, similar as ChIA-Drop vs Hi-C. On the contrary, the cross-data-type comparison, say Hi-C vs ChIA-PET and ChIA-Drop vs RNAPII ChIA-Drop, the correlation coefficient values were in negatives (−0.01 to −0.34). Together, this comprehensive comparison demonstrated that both ChIA-Drop and RNAPII ChIA-Drop were highly reproducible, and were comparable with Hi-C and ChIA-PET, respectively.

Review of Shannon Entropy

Many phenomenon can be represented as a probability, indicating a likelihood of an event. A set of disjoint events can then be expressed as a probability vector, where each entry indicates a probability of the corresponding event. The Shannon entropy, a fundamental concept in information theory, quantifies the information content or the randomness of a probability vector. More formerly, given a probability vector $p= \ldots, [p_1, \ldots, p_n]$ of $n$ events, where $p_i$ denotes a probability of the ith event, the Shannon entropy H is defined as follows:

$$H([p_1, \ldots, p_n]) = \sum_{i=1}^{n} p_i \log_2\left(\frac{1}{p_i}\right)$$

Here, $0 \log_2 0$ is defined to be 0. The smallest value H can take is 0, when $p_i = 1$ for an ith event and 0 otherwise: $H([1,0, ,0])=1$ loge $1=0$. By contrast, the largest possible value of H is $\log_2 n$, which occurs when all events are equally likely. For example, given 4 equally likely events, $H([¼, ¼, ¼, ¼]) = ¼ \log_2 4 + ¼ \log_2 4 + ¼ \log_2 4 + ¼ \log_2 4 = 4 \cdot ¼ \log_2 4 = \log_2 4 = 2$. Thus, the Shannon entropy may be normalized by $\log_2 n$:

$$H_{norm}([p_1, \ldots, p_n]) = \frac{\sum_{i=1}^{n} p_i \log_2\left(\frac{1}{p_i}\right)}{\log_2 n}$$

As a result, $H_{norm}$ takes in values between 0 and 1 for any probability vector p.

The normalized Shannon entropy can be interpreted in several ways. In information theory, it is often a standard measure of information content, with 1 containing the most information and 0 indicating the least information. Alternatively, it can describe randomness or chaos of events, with 1 being most random and 0 being most deterministic. Similarly, in analyzing ChIA-Drop chromatin complexes, high entropy (close to 1) is treated as heterogeneous and low entropy (close to 0) as homogeneous.

Figures 23B, 24:
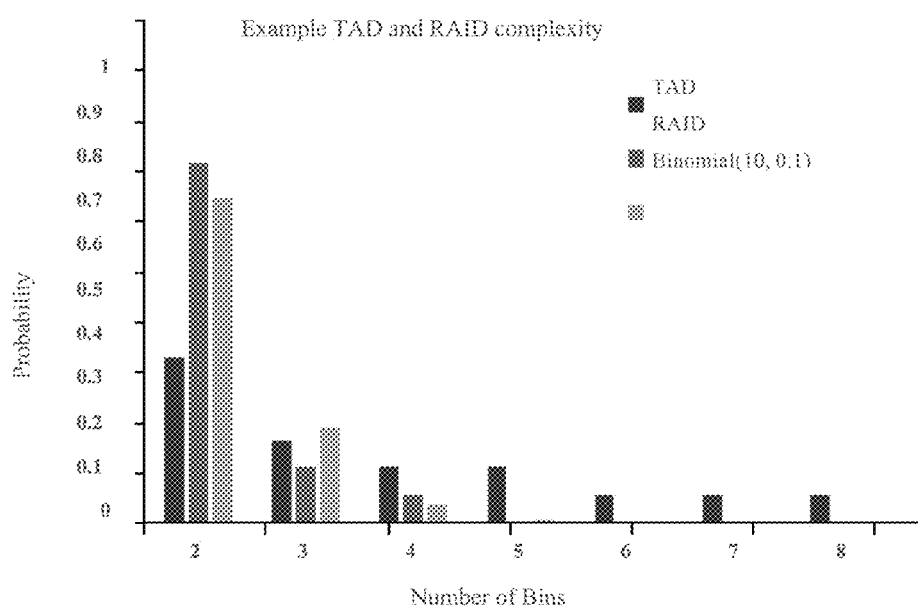
FIG. 24 is a histogram showing the observed probability in TAD and RAID along with the expected probability. In each set of bars (2-8) the first bar on left is TAD, the center bar is RAID, and the bar on right is binomial (10, 0.1). In sets 5-8, the most visible bar is TAD.

Example of complexity and heterogeneity in ChIA-Drop and RNAPII ChIA-Drop data Here are provided simple hypothetical examples of a TAD and a RAID, both binned at 5 Kb resolution, and demonstrate the analyses methods described above, see FIG. 23A-B.

There are 10 bins of lengths 5 Kb, and each of 16 GEMs are converted into binary vectors, with 1 if a fragment lands in a specific bin, and 0 otherwise. Counting the number of bins covered by each GEM separately for a TAD and a RAID, the following table (Table 3) can be constructed.

TABLE 3

| # of bins covered | 2 | 3 | 4 | 5 | 6 | 7 | 8 |
|---|---|---|---|---|---|---|---|
| TAD (GEM count) | 6 | 3 | 2 | 2 | 1 | 1 | 1 |
| TAD (probability) | 0.375 | 0.1875 | 0.125 | 0.125 | 0.0625 | 0.0625 | 0.0625 |
| RAID (GEM count) | 13 | 2 | 1 | 0 | 0 | 0 | 0 |
| RAID (probability) | 0.813 | 0.125 | 0.062 | 0 | 0 | 0 | 0 |
| Binomial(10, 0.1) | 0.734 | 0.217 | 0.042 | 0.006 | 0 | 0 | 0 |

A theoretical expected distribution is Binomial (10,0.1), based on the assumption that each bin is an independent Bernoulli trial with probability $\frac{1}{10}$ and the number of successes is recorded. Due to the fact that the focus was on GEMs that span at least 2 bins (for studying interactions), the Binomial probabilities were normalized by excluding the cases of 0 or 1 success. Finally, the observed probability in TAD and RAID is plotted, along with the expected probability, see FIG. 24.

Repeating the same process for all TADs and RAIDs, the summary distributions were plotted (FIG. 4I-J). The same TAD and RAID above can demonstrate the heterogeneity analyses. A first step is to identify the unique combinations captured in TAD (there were 15) and RAID (there were 8), and count the number of GEMs covering each combination.

These unique counts are divided by the total number of GEMs, 16 in both cases, and the probability vector is an input to the normalized Shannon entropy calculation as defined above. Specifically, for a TAD, $$H_{norm}([1/16,1/16,1/16,1/16,1/16,1/16,1/16,1/16,1/16,1/16,1/16,1/16,1/16,2/16,1/16,1/16])=0.99$$

and for a RAID $$H_{norm}([1/16,1/16,1/16,2/16,2/16,6/16,2/16,1/16])=0.89$$

Even though both are highly heterogeneous, RNAPII ChIA-Drop may exhibit slightly more homogeneity due to a possible promoter in bin 2.

REFERENCES

1. Cremer, T. & Cremer, M. Chromosome territories. Cold Spring Harbor perspectives in biology 2, a003889, doi: 10.1101/cshperspect.a003889 (2010).
2. Lieberman-Aiden, E. et al. Comprehensive mapping of long-range interactions reveals folding principles of the human genome. Science 326, 289-293, doi:10.1126/science.1181369 (2009).
3. Fullwood, M. J. et al. An oestrogen-receptor-alpha-bound human chromatin interactome. Nature 462, 58-64, doi: 10.1038/nature08497 (2009).
4. Dixon, J. R. et al. Topological domains in mammalian genomes identified by analysis of chromatin interactions. Nature 485, 376-380, doi:10.1038/nature11082 (2012).
5. Sexton, T. et al. Three-dimensional folding and functional organization principles of the *Drosophila* genome. Cell 148, 458-472, doi:10.1016/j.cell.2012.01.010 (2012).
6. Tang, Z. et al. CTCF-Mediated Human 3D Genome Architecture Reveals Chromatin Topology for Transcription. Cell 163, 1611-1627, doi:10.1016/j.cell.2015.11.024 (2015).
7. Ji, X. et al. 3D Chromosome Regulatory Landscape of Human Pluripotent Cells. Cell stem cell 18, 262-275, doi:10.1016/j.stem.2015.11.007 (2016).
8. Weintraub, A. S. et al. YY1 Is a Structural Regulator of Enhancer-Promoter Loops. Cell 171, 1573-1588 e1528, doi:10.1016/j.cell.2017.11.008 (2017).
9. Li, G. et al. Extensive promoter-centered chromatin interactions provide a topological basis for transcription regulation. Cell 148, 84-98, doi:10.1016/j.cell.2011.12.014 (2012).
10. Nagano, T. et al. Single-cell Hi-C reveals cell-to-cell variability in chromosome structure. Nature 502, 59-64, doi:10.1038/nature12593 (2013).
11. Ramani, V. et al. Massively multiplex single-cell Hi-C. Nature methods 14, 263-266, doi:10.1038/nmeth.4155 (2017).
12. Stevens, T. J. et al. 3D structures of individual mammalian genomes studied by single-cell Hi-C. Nature 544, 59-64, doi:10.1038/nature21429 (2017).
13. Beagrie, R. A. et al. Complex multi-enhancer contacts captured by genome architecture mapping. Nature 543, 519-524, doi:10.1038/nature21411 (2017).
14. Quinodoz, S. A. et al. Higher-Order Inter-chromosomal Hubs Shape 3D Genome Organization in the Nucleus. Cell 174, 744-757 e724, doi:10.1016/j.cell.2018.05.024 (2018).
15. Caen, O., Lu, H., Nizard, P. & Taly, V. Microfluidics as a Strategic Player to Decipher Single-Cell Omics? Trends in biotechnology 35, 713-727, doi:10.1016/j.tibtech.2017.05.004 (2017).
16. Kang, H. M. et al. Multiplexed droplet single-cell RNA-sequencing using natural genetic variation. Nature biotechnology 36, 89-94, doi:10.1038/nbt.4042 (2018).
17. Zheng, G. X. et al. Haplotyping germline and cancer genomes with high-throughput linked-read sequencing. Nature biotechnology 34, 303-311, doi:10.1038/nbt.3432 (2016).
18. Kharchenko, P. V. et al. Comprehensive analysis of the chromatin landscape in *Drosophila melanogaster*. Nature 471, 480-485, doi:10.1038/nature09725 (2011).
19. Lajoie, B. R., Dekker, J. & Kaplan, N. The Hitchhiker's guide to Hi-C analysis: practical guidelines. Methods 72, 65-75, doi:10.1016/j.ymeth.2014.10.031 (2015).
20. Meaburn, K. J. & Misteli, T. Cell biology: chromosome territories. Nature 445, 379-781, doi:10.1038/445379a (2007).
21. Ramirez, F. et al. High-Affinity Sites Form an Interaction Network to Facilitate Spreading of the MSL Complex across the X Chromosome in *Drosophila*. Molecular cell 60, 146-162, doi:10.1016/j.molcel.2015.08.024 (2015).
22. Ulianov, S. V. et al. Active chromatin and transcription play a key role in chromosome partitioning into topologically associating domains. Genome research 26, 70-84, doi:10.1101/gr.196006.115 (2016).
23. Crane, E. et al. Condensin-driven remodelling of X chromosome topology during dosage compensation. Nature 523, 240-244, doi:10.1038/nature14450 (2015).
24. Lanzuolo, C., Roure, V., Dekker, J., Bantignies, F. & Orlando, V. Polycomb response elements mediate the formation of chromosome higher-order structures in the bithorax complex. Nature cell biology 9, 1167-1174, doi:10.1038/ncb1637 (2007).
25. Szabo, Q. et al. TADs are 3D structural units of higher-order chromosome organization in *Drosophila*. Science advances 4, eaar8082, doi:10.1126/sciadv.aar8082 (2018).
26. Rowley, M. J. et al. Evolutionarily Conserved Principles Predict 3D Chromatin Organization. Molecular cell 67, 837-852 e837, doi:10.1016/j.molcel.2017.07.022 (2017).
27. Cubenas-Potts, C. & Corces, V. G. Architectural proteins, transcription, and the three-dimensional organization of the genome. FEBS letters 589, 2923-2930, doi: 10.1016/j.febslet.2015.05.025 (2015).
28. Yang, J., Ramos, E. & Corces, V. G. The BEAF-32 insulator coordinates genome organization and function during the evolution of *Drosophila* species. Genome research 22, 2199-2207, doi:10.1101/gr.142125.112 (2012).
29. van Bemmel, J. G. et al. The insulator protein SU(HW) fine-tunes nuclear lamina interactions of the *Drosophila* genome. PloS one 5, e15013, doi:10.1371/journal.pone.0015013 (2010).
30. Li, X. et al. Long-read ChIA-PET for base-pair-resolution mapping of haplotype-specific chromatin interactions. Nature protocols 12, 899-915, doi:10.1038/nprot.2017.012 (2017).
31. Teves, S. S. & Henikoff, S. Heat shock reduces stalled RNA polymerase II and nucleosome turnover genome-wide. Genes & development 25, 2387-2397, doi:10.1101/gad.178079.111 10.1101/gad.177675.111 (2011).
32. Bond-Matthews, B. & Davidson, N. Transcription from each of the *Drosophila* act5C leader exons is driven by a separate functional promoter. Gene 62, 289-300 (1988).
33. Duff, M. O. et al. Genome-wide identification of zero nucleotide recursive splicing in *Drosophila*. Nature 521, 376-379, doi:10.1038/nature14475 (2015).

34. Alberts, B., Johnson, A., Lewis, J., Raff, M., Roberts, K. and Walter, P. Molecular biology of the cell. 4 edn, (Garland Science, 2002).
35. Bintu, B. et al. Super-resolution chromatin tracing reveals domains and cooperative interactions in single cells. Science 362, doi:10.1126/science.aau1783 (2018).
36. Cisse, II et al. Real-time dynamics of RNA polymerase II clustering in live human cells. Science 341, 664-667, doi:10.1126/science.1239053 (2013).
37. Zhao, J., Favero, D. S., Peng, H. & Neff, M. M. Arabidopsis thaliana AHL family modulates hypocotyl growth redundantly by interacting with each other via the PPC/DUF296 domain. Proceedings of the National Academy of Sciences of the United States of America 110, E4688-4697, doi:10.1073/pnas.1219277110 (2013).
38. Cho, W. K. et al. RNA Polymerase II cluster dynamics predict mRNA output in living cells. eLife 5, doi:10.7554/eLife.13617 (2016).
39. Cook, P. R. A model for all genomes: the role of transcription factories. Journal of molecular biology 395, 1-10, doi:10.1016/j.jmb.2009.10.031 (2010).
40. Hendrix, D. A., Hong, J.-W., Zeitlinger, J., Rokhsar, D. S. & Levine, M. S. Promoter elements associated with RNA Pol II stalling in the *Drosophila* embryo. Proc. Natl. Acad. Sci. 105, 7762-7767 (2008).
41. Yang, T. et al. HiCRep: assessing the reproducibility of Hi-C data using a stratum-adjusted correlation coefficient. Genome research 27, 1939-1949, doi:10.1101/gr.220640.117 (2017).
42. Quinlan, A. R. & Hall, I. M. BEDTools: a flexible suite of utilities for comparing genomic features. Bioinformatics 26, 841-842 (2010).
43. Shannon, C. E. A mathematical theory of communication. ACM SIGMOBILE Mobile Computing and Communications Review 5, 3-55 (2001).
44. Zhao, S., Xi, L. & Zhang, B. Union Exon Based Approach for RNA-Seq Gene Quantification: To Be or Not to Be? PloS one 10, e0141910, doi:10.1371/journal.pone.0141910 (2015).
45. van der Maaten, L. J. P. H., G. E. Visualizing High-Dimensional Data Using t-SNE. Journal of Machine Learning Research 9, 2579-2605 (2008).
46. Li, H. & Durbin, R. Fast and accurate short read alignment with Burrows-Wheeler transform. Bioinformatics 25, 1754-1760, doi:10.1093/bioinformatics/btp324 (2009).
47. Li, H. et al. The Sequence Alignment/Map format and SAMtools. Bioinformatics 25, 2078-2079, doi:10.1093/bioinformatics/btp352 (2009).

Equivalents

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

What is claimed is:

1. A method of determining a physical interaction between nucleic acids in chromatin complexes at a single molecule level, said method comprising the steps of:
   a) obtaining a population of chromatin complexes by providing a crosslinked, permeabilized nucleus and digesting the crosslinked, permeabilized nucleus;
   b) forming a population of barcoded chromatin complexes comprising the chromatin complexes by contacting the population of chromatin complexes with a plurality of barcode substrates, each individual substrate of the plurality of barcode substrates comprising multiple copies of one of a plurality of unique DNA barcodes of nucleotides, and each of the chromatin complexes ligated to multiple copies of one of the unique DNA barcodes of nucleotides:
   c) partitioning the population of barcoded chromatin complexes into droplets such that each of the droplets contains not more than one of the barcoded chromatin complexes;
   d) amplifying the barcoded chromatin complexes in each of the droplets such that barcoded DNA amplicons are generated in each of the droplets;
   e) releasing the barcoded DNA amplicons from each of the droplets;
   f) generating a plurality of DNA sequence reads by sequencing the barcoded DNA amplicons; and
   g) generating a 3D genomic connectivity map by mapping the plurality of sequence reads to a referenced genome and producing a genomic location of the sequence reads on the chromatin complexes, thereby determining the physical interaction between nucleic acids in the chromatin complexes at the single molecule level.

2. The method of claim 1, wherein the unique DNA barcode of nucleotides comprises ten or more nucleotides.

3. The method of claim 1, wherein said crosslinked, permeabilized nucleus is prepared by forming a crosslinked cell comprising a crosslinked nucleus by crosslinking a cell with a crosslinking reagent, producing a lysed cell by lysing the crosslinked cell, isolating the crosslinked nucleus from the lysed cell, and permeabilizing the crosslinked nucleus isolated from the lysed cell with a permeabilizing reagent.

4. The method of claim 3, wherein the crosslinking reagent is formaldehyde.

5. The method of claim 3, wherein the permeabilizing reagent is sodium dodecyl sulfate.

6. The method of claim 1, wherein the cross-linked permeabilized nucleus is digested by generating chromatin fragments by sonication and incubating said chromatin fragments with one or more restriction enzymes.

7. The method of claim 1, wherein the population of chromatin complexes comprises DNA fragments of 300-6000 bp.

8. The method of claim 1, further comprising, prior to said contacting the population of chromatin complexes with the plurality of barcode substrates, producing a population of chromatin complexes enriched for a chromatin protein.

9. The method of claim 8, wherein said producing a population of chromatin complexes enriched for a chromatin protein comprises incubating the population of chromatin complexes with a monoclonal antibody specific for the chromatin protein, producing chromatin complexes bound to the monoclonal antibody, isolating the chromatin complexes bound to the monoclonal antibody, and forming the population of chromatin complexes enriched for the chromatin protein by removing the monoclonal antibody from the chromatin complexes bound to the monoclonal antibody.

10. The method of claim 8, wherein the chromatin protein is RNA polymerase II (RNAPII), retinoic acid receptor alpha (RARA), estrogen receptor (ER), or CCCTC-binding factor (CTCF).

11. The method of claim 1, wherein the plurality of barcode substrates is a plurality of gel beads in emulsion (GEMs).

12. The method of claim 11, wherein each of the GEMs comprises one of the barcode substrates and the unique DNA barcodes of nucleotides comprising a PCR priming site, a sequence reading site, a barcode, and a random priming nucleotide sequence.

13. The method of claim 12, wherein the barcode is a 15 to 25 nucleotide barcode or a 16 to 20 nucleotide barcode.

14. The method of claim 12, wherein the random priming nucleotide sequence is a random 8-mer.

15. The method of claim 11, wherein the barcoded DNA amplicons are analyzed by a sequencing device with a read length of 150 bp and each of the sequence reads contains the barcode.

16. The method of claim 1, further comprising, after the releasing step, the barcoded DNA amplicons are subjected to one or more of end repair, A-tailing, and adapter ligation prior to the sequencing step.

* * * * *

SEQUENCE LISTING

<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 1
tacttgttct tgtatc